US008242175B2

(12) United States Patent
Mai et al.

(10) Patent No.: US 8,242,175 B2
(45) Date of Patent: Aug. 14, 2012

(54) CLASS OF HISTONE DEACETYLASE INHIBITORS

(75) Inventors: Antonello Mai, Rome (IT); Saverio Minucci, Noverasco Opera (IT); Florian Thaler, Gerenzano (IT); Gilles Pain, Castelforte (IT); Andrea Colombo, Parabiago (IT); Stefania Gagliardi, Vimercate (IT); Pier Giuseppe Pelicci, Opera (IT); Marco Ballarini, Milan (IT); Gaetano Gargiulo, S. Agnello (IT); Silvio Massa, Rome (IT)

(73) Assignee: DAC S.R.L., Milan (IT)

( * ) Notice: Subject to any disclaimer, the term of this patent is extended or adjusted under 35 U.S.C. 154(b) by 48 days.

(21) Appl. No.: 12/962,209

(22) Filed: Dec. 7, 2010

(65) Prior Publication Data

US 2011/0077247 A1 Mar. 31, 2011

Related U.S. Application Data

(60) Continuation-in-part of application No. 12/791,465, filed on Jun. 1, 2010, now Pat. No. 8,058,273, which is a division of application No. 11/664,187, filed as application No. PCT/EP2005/054949 on Sep. 30, 2005, now Pat. No. 7,803,800, said application No. 12/962,209 is a continuation of application No. 12/295,498, filed as application No. PCT/EP2007/053097 on Mar. 30, 2007, now abandoned.

(30) Foreign Application Priority Data

Oct. 1, 2004 (IT) ............................... MI2004A1869
Mar. 31, 2006 (IT) ............................... MI2006A0621

(51) Int. Cl.
*A61K 31/19* (2006.01)
*A61K 31/5377* (2006.01)
*A61K 31/495* (2006.01)
*A61K 31/451* (2006.01)
*A61K 31/445* (2006.01)
*A61K 31/5375* (2006.01)
*A61K 31/496* (2006.01)
*A61P 35/00* (2006.01)
*C07D 295/155* (2006.01)
*C07D 211/58* (2006.01)
*C07D 401/10* (2006.01)
*C07D 413/10* (2006.01)
*C07C 259/06* (2006.01)

(52) U.S. Cl. .................. 514/575; 514/235.5; 514/238.2; 514/252.12; 514/253.01; 514/255.01; 514/255.03; 514/329; 544/131; 544/168; 544/360; 544/383; 544/389; 544/390; 544/393; 544/400; 546/223; 562/621

(58) Field of Classification Search ............. 514/252.12, 514/253.01, 255.01, 255.03, 329, 575; 544/131; 544/168, 360, 383, 389, 390, 393, 400; 546/223; 562/621

See application file for complete search history.

(56) References Cited

FOREIGN PATENT DOCUMENTS

| WO | 95/13264 A1 | 5/1995 |
|---|---|---|
| WO | 01/38322 A1 | 5/2001 |
| WO | 02/22577 A2 | 3/2002 |
| WO | 02/26696 A1 | 4/2002 |
| WO | 02/30879 A2 | 4/2002 |
| WO | 03/087066 A1 | 10/2003 |
| WO | 2004/063169 A1 | 7/2004 |
| WO | 2005/040101 A1 | 5/2005 |
| WO | 2005/040161 A1 | 5/2005 |
| WO | 2006/037761 A1 | 4/2006 |
| WO | 2007/113249 A2 | 10/2007 |

OTHER PUBLICATIONS

Mai et al. "Discovery of (Aryloxopropenyl)pyrrolyl Hydroxamides as Selective Inhibitors of Class IIa Histone Deacetylase Homologue HD1-A" J. Med. Chem. 2003, vol. 46, pp. 4826-4829.*
Robert P. Sheridan., "The Most Common Chemical Replacements in Drug-Like Compounds," J. Chem. Inf. Comput. Sci, Jan. 3, 2002, 103-108, vol. 42, American Chemical Society.
Antonello Mai et al., "Discovery of (Aryloxopropenyl)pyrrolyl Hydroxyamides as Selective Inhibitors of Class IIa Histone Deacetylase Homologue HDI-A," J. Med. Chem., Oct. 15, 2003, 4826-4829, vol. 46, American Chemical Society.
A. Mai, et al., "Synthesis and Biological Evaluation of 2-, 3-, and 4-Acylaminocinnamyl-N-hydroxyamides as Novel Synthetic HDAC Inhibitors," Medicinal Chemistry, 2005, 245-254, vol. 1, Bentham Science Publishers Ltd.
Paul W. Finn, et al., "Novel Sulfonamide Derivatives as Inhibitors of Histone Deacetylase," Helvetica Chimica Acta, 2005, 1630-1657, vol. 88, Verlag Helvetica Chimica Acta AG.

(Continued)

*Primary Examiner* — Joseph Kosack
(74) *Attorney, Agent, or Firm* — McCormick, Paulding & Huber LLP

(57) ABSTRACT

New histone deacetylase inhibitors according to the general formula (I)

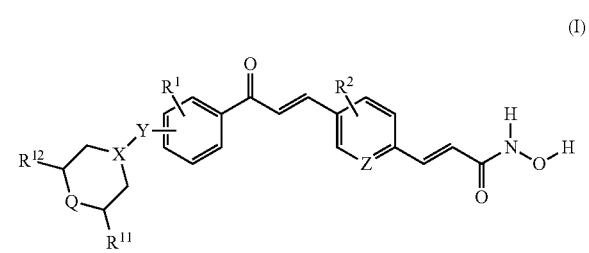

wherein: Q is a bond, $CH_2$, $CH-NR^3R^4$, $NR^5$ or oxygen, X is CH or nitrogen, Y is a bond, $CH_2$, oxygen or $NR^6$, Z is CH or nitrogen, $R^1$, $R^2$ are, independently, hydrogen, halogen, $C_1$-$C_6$ alkyl or $C_1$-$C_6$ haloalkyl, $R^{11}$, $R^{12}$ are, independently, hydrogen or $C_1$-$C_6$ alkyl, and $R^3$, $R^4$, $R^5$ and $R^6$ are as further defined in the specification.

15 Claims, No Drawings

OTHER PUBLICATIONS

Peeyush K. Lala et al., "Role of nitric oxide in tumor progression: Lessons from experimental tumors," Cancer and Metastasis Reviews, 1998, 91-106, vol. 17, Kluwer Academic Publishers.

T. R. Golub et al., "Molecular Classification of Cancer: Class Discovery and Class Prediction by Gene Expression Monitoring," Reports, Oct. 15, 1999, 531-536, vol. 286, Science.

Cancer [online], retrieved on Jul. 6, 2007 from the internet, URL http://www.nlm.nih.gov/medlineplus/print/cancer.html.

Cancer [online], retrieved on Jul. 6, 2007 from the internet, URL http://en.wikipedia.org/wiki/Cancer.

Milin R. Acharya et al., "Rational Development of Histone Deacetylase Inhibitors as Anticancer Agents: A Review," Mol Pharmacol, 2005, 917-932, vol. 68, No. 4.

Paul A. Marks et al., "Histone Deacetylase Inhibitors: Inducers of Differentiation or Apoptosis of Transformed Cells," Journal of the National Cancer Institute, Aug. 2, 2000, 1210-1216, vol. 92, No. 15, Oxford University Press.

International Search Report from PCT/EP2005/054949 dated Feb. 24, 2006 (4 pages).

International Search Report from PCT/EP2007/053097 dated Sep. 12, 2007 (2 pages).

International Search Report from PCT/EP2008/061140 dated Feb. 5, 2009 (2 pages).

Written Opinion of the International Searching Authority from PCT/EP2008/061140 (4 pages), 2010.

Silvio Massa, et al., "3-(4-Aroyl-1H-pyrrol-2-yl)-N-hydroxy-2-propenamides, a New Class of Synthetic Histone Deacetylase Inhibitors," J. Med. Chem., 2001, 2069-2072, vol. 44, American Chemical Society.

Antonello Mai, et al., "Binding Mode Analysis of 3-(4-Benzoyl-1-methyl-1H-2-pyrrolyl)-N-hydroxy-2-propenamide: A New Synthetic Histone Deacetylase Inhibitor Inducing Histone Hyperacetylation, Growth Inhibition, and Terminal Cell Differentiation," J. Med. Chem., 2002, 1778-1784, vol. 45, American Chemical Society.

Antonello Mai, et al., "3-(4-Aroyl-1-methyl-1H-2-pyrrolyl)-N-hydroxy-2-alkylamides as a New Class of Synthetic Histone Deacetylase Inhibitors. 1. Design, Synthesis, Biological Evaluation, and Binding Mode Studies Performed through Three Different Docking Procedures," J. Med. Chem., 2003, 512-524, vol. 46, American Chemical Society.

Antonello Mai, et al., "3-(4-Aroyl-1-methyl-1H-2-pyrrolyl)-N-hydroxy-2-propenamides as a New Class of Synthetic Histone Deacetylase Inhibitors. 2. Effect of Pyrrole-C2 and/or -C4 Substitutions on Biological Activity," J. Med. Chem., 2004, 1098-1109, vol. 47, American Chemical Society.

Rino Ragno, et al., "3-(4-Aroyl-1-methyl-1H-pyrrol-2-yl)-N-hydroxy-2-propenamides as a New Class of Synthetic Histone Deacetylase Inhibitors. 3. Discovery of Novel Lead Compounds through Structure-Based Drug Design and Docking Studies," J. Med. Chem., 2004, 1351-1359, vol. 47, American Chemical Society.

Antonello Mai, et al., "Class II (IIa)-Selective Histone Deacetylase Inhibitors. 1. Synthesis and Biological Evaluation of Novel (Aryloxopropenyl)pyrrolyl Hydroxyamides," J. Med. Chem., 2005, 3344-3353, vol. 48, American Chemical Society.

Simona Ronzoni, et al., "New Method to Detect Histone Acetylation Levels by Flow Cytometry," Cytometry Part A, 2005, 52-61, vol. 66A, Wiley-Liss, Inc.

James R Davie, "Covalent modifications of histones: expression from chromatin templates," Current Opinion in Genetics & Development, 1998, 173-178, vol. 8, Current Biology Ltd ISSN 0959-437X.

Jiansheng Wu et al., "25 years after the nucleosome model: chromatin modifications," TIBS 25, Dec. 2000, 619-623, Elsevier Science Ltd.

Richard J Lin et al., "Transcriptional regulation in acute promyelocytic leukemia," Oncogene, 2001, 7204-7215, vol. 20, Nature Publishing Group.

Arthur Zelent et al., "Translocations of the RARα gene in acute promyelocytic leukemia," Oncogene, 2001, 7186-7203, vol. 20, Nature Publishing Group.

Pier Paolo Pandolfi, "Transcription therapy for cancer," Oncogene, 2001, 3116-3127, vol. 20, Nature Publishing Group.

Francesco Grignani et al., "Fusion proteins of the retinoic acid receptor-α recruit histone deacetylase in promyelocytic leukaemia," Nature, Feb. 19, 1998, 815-818, vol. 391, MacMillan Publishers Ltd.

Bart Lutterbach et al., "ETO, a Target of t(8;21) in Acute Leukemia, Interacts with the N-CoR and mSin3 Corepressors," Molecular and Cellular Biology, Dec. 1998, 7176-7184, vol. 18, No. 12, American Society for Microbiology.

Robert J Ferrante et al., "Histone Deacetylase Inhibition by Sodium Butyrate Chemotherapy Ameliorates the Neurodegenerative Phenotype in Huntington's Disease Mice," The Journal of Neuroscience, Oct. 15, 2003, 9418-9427, vol. 23, No. 28, Society for Neuroscience.

Emma Hockly et al., "Suberoylanilide hydroxamic acid, a histone deacetylase inhibitor, ameliorates motor deficits in a mouse model of Huntington's disease," PNAS, Feb. 18, 2003, 2041-2046, vol. 100, No. 4.

Robin S B Williams et al., "A common mechanism of action for three mood-stabilizing drugs," Nature, May 16, 2002, 292-295, vol. 417, MacMillan Magazines Ltd.

Erminio Costa et al., "GABAergic Cortical Neuron Chromatin as a Putative Target to Treat Schizophrenia Vulnerability," Critical Reviews in Neurobiology, 2003, 121-142, vol. 15, No. 2.

Simon P Chandler et al., "Fragile X (CGG)n repeats induce a transcriptional repression in cis upon a linked promoter: Evidence for a chromatin mediated effect," BMC Molecular Biology, Mar. 21, 2003, vol. 4, No. 3, BMC Molecular Biology.

Pietro Chiurazzi et al., "Synergistic effect of histone hyperacetylation and DNA demethylation in the reactivation of the FMR1 gene," Human Molecular Genetics, 1999, 2317-2323, vol. 8, No. 12, Oxford University Press.

L Bodai et al., "Altered Protein Acetylation in Polyglutamine Diseases," Current Medicinal Chemistry, 2003, 2577-2587, vol. 10, Bentham Science Publishers Ltd.

Robert E Hughes, "Polyglutamine Disease: Acetyltransferases Awry," Current Biology, Feb. 19, 2002, R141-R143, vol. 12, Elsevier Science Ltd.

Mi Ra Jeong et al., "Valproic acid, a mood stabilizer and anticonvulsant, protects rat cerebral cortical neurons from spontaneous cell death: a role of histone deacetylase inhibition," FEBS Letters, 2003, 74-78, vol. 542, Elsevier Science B.V.

Ming Ren et al., "Valproic acid reduces brain damage induced by transient focal cerebral ischemia in rats: potential roles of histone deacetylase inhibition and heat shock protein induction," Journal of Neurochemistry, 2004, 1358-1367, vol. 89, International Society for Neurochemistry.

Hoon Ryu et al., "Histone deacetylase inhibitors prevent oxidative neuronal death independent of expanded polyglutamine repeats via an Sp1-dependent pathway," PNAS, Apr. 1, 2003, 4281-4286, vol. 100, No. 7.

Tiina Suuronen et al., "Regulation of microglial inflammatory response by histone deacetylase inhibitors," Journal of Neurochemistry, 2003, 407-416, vol. 87, International Society for Neurochemistry.

Sara Eyal et al., "The Activity of Antiepileptic Drugs as Histone Deacetylase Inhibitors," Epilepsia, 2004, 737-744, vol. 45, No. 7, Blackwell Publishing Inc, International League Against Epilepsy.

Yunfei Huang et al., "Altered Histone Acetylation at Glutamate Receptor 2 and Brain-Derived Neurotrophic Factor Genes is an Early Event Triggered by Status Epilepticus," The Journal of Neuroscience, Oct. 1, 2002, 8422-8428, vol. 22, No. 19, Society for Neuroscience.

Lisa J Corcoran et al., "A Novel Action of Histone Deacetylase Inhibitors in a Protein Aggresome Disease Model," Current Biology, Mar. 23, 2004, 488-492, vol. 14, Elsevier Ltd.

Emmanuelle Adam et al., "Potentiation of Tumor Necrosis Factor-Induced NF-kB Activation by Deacetylase Inhibitors is Associated with a Delayed Cytoplasmic Reappearance of IkBα," Molecular and Cellular Biology, Sep. 2003, 6200-6209, vol. 23, No. 17, American Society for Microbiology.

Carine Van Lint et al., "Transcriptional activation and chromatin remodeling of the HIV-1 promoter in response to histone acetylation," The EMBO Journal, 1996, 1112-1120, vol. 15, No. 5, Oxford University Press.

Dominique Demonte et al., "Administration of HDAC inhibitors to reactivate HIV-1 expression in latent cellular reservoirs: implications for the development of therapeutic strategies," Biochemical Pharmacology, 2004, 1231-1238, vol. 68, Elsevier Inc.

Loyda Ylisastigui et al., "Coaxing HIV-1 from resting CD4 T cells: histone deacetylase inhibition allows latent viral expression," AIDS, 2004, 1101-1108, vol. 18, Lippincott Williams & Wilkins.

Soren Skov et al., "Histone deacetylase inhibitors: a new class of immunosuppressors targeting a novel signal pathway essential for CD154 expression," Blood, Feb. 15, 2003, 1430-1438, vol. 101, No. 4, The American Society of Hematology.

Pavan Reddy et al., "Histone deacetylase inhibitor suberoylanilide hydroxamic acid reduces acute graft-versus-host disease and preserves graft-versus-leukemia effect," PNAS, Mar. 16, 2004, 3921-3926, vol. 101, No. 11, The National Academy of Sciences of the USA.

Hyun Kook et al., "Cardiac hypertrophy and histone deacetylase-dependent transcriptional repression mediated by the atypical homeodomain protein Hop," The Journal of Clinical Investigation, Sep. 2003, 863-871, vol. 112, No. 6.

Timothy A McKinsey et al., "Dual roles of histone deacetylases in the control of cardiac growth," Reversible protein acetylation, 2004, 132-145, 163-169, Novartis Foundation Symposium 259.

Yasuo Hamamori et al., "HATs off to Hop: recruitment of a class I histone deacetylase incriminates a novel transcriptional pathway that opposes cardiac hypertrophy," The Journal of Clinical Investigation, Sep. 2003, 824-826, vol. 112, No. 6.

Krista Rombouts et al., "Trichostatin A, a Histone Deacetylase Inhibitor, Suppresses Collagen Synthesis and Prevents TGF-β1-Induced Fibrogenesis in Skin Fibroblasts," Experimental Cell Research, 2002, 184-197, vol. 278, Elsevier Science.

Toshiro Niki et al., "A Histone Deacetylase Inhibitor, Trichostatin A, Suppresses Myofibroblastic Differentiation of Rat Hepatic Stellate Cells in Primary Culture," Hepatology, Mar. 1999, 858-867, vol. 29, No. 3, The American Association for the Study of Liver Diseases.

Makoto Minamiyama et al., "Sodium butyrate ameliorates phenotypic expression in a transgenic mouse model of spinal and bulbar muscular atrophy," Human Molecular Genetics, 2004, 1183-1192, vol. 13, No. 11, Oxford University Press.

Yih-Lin Chung et al., "A Therapeutic Strategy Uses Histone Deacetylase Inhibitors to Modulate the Expression of Genes Involved in the Pathogenesis of Rheumatoid Arthritis," Molecular Therapy, Nov. 2003, 707-717, vol. 8, No. 5, The American Society of Gene Therapy.

Nilamadhab Mishra et al., "Histone deacetylase inhibitors modulate renal disease in the MRL-lpr/lpr mouse," The Journal of Clinical Investigation, Feb. 2003, 539-552, vol. 111, No. 4.

Fiona McLaughlin et al., "Histone Deacetylase Inhibitors in Psoriasis Therapy," Current Drug Targets—Inflammation & Allergy, 2004, 213-219, vol. 3, Bentham Science Publishers Ltd.

Marcus D Saemann et al., "Short-chain fatty acids: bacterial mediators of a balanced host-microbial relationship in the human gut," Wien Klin Wochenschr, 2002, 289-300, vol. 114, No. 8-9.

Griffin P Rodgers et al., "Advances in experimental treatment of β-thalassaemia," Expert Opinion on Investigational Drugs, 2001, 925-934, vol. 10, No. 5, Ashley Publications Ltd.

Peter J Barnes, "Pulmonary Perspective—Theophylline—New Perspectives for an Old Drug," Am J Respir Crit Care Med, 2003, 813-818, vol. 167.

Juan M Alarcon et al., "Chromatin Acetylation, Memory, and LTP Are Impaired in CBP+/− Mice: A Model for the Cognitive Deficit in Rubinstein-Taybi Syndrome and its Amelioration," Neuron, Jun. 24, 2004, 947-959, vol. 42, Cell Press.

Paul A Marks, MD et al., "Histone deacetylase inhibitors as new cancer drugs," Current Opinion in Oncology, 2001, 477-483, vol. 13, Lippincott Williams & Wilkins, Inc.

Ricky W Johnstone, "Histone-Deacetylase Inhibitors: Novel Drugs for the Treatment of Cancer," Nature Reviews—Drug Discovery, Apr. 2002, 287-299, vol. 1, Nature Publishing Group.

Keith B Glaser, "HDAC inhibitors: Clinical update and mechanism-based potential," Biochemical Pharmacology, 2007, 659-671, vol. 74, Elsevier Inc.

David M Vigushin et al., "Histone deacetylase inhibitors in cancer treatment," Anti-Cancer Drugs, 2002, 1-13, vol. 13, Lippincott Williams & Wilkins.

Thomas A Miller, "Patent status of histone deacetylase inhibitors," Expert Opin. Ther. Patents, 2004, 791-804, vol. 14, No. 6, Ashley Publications Ltd.

Thomas A Miller et al., "Histone Deacetylase Inhibitors," Journal of Medicinal Chemistry, Nov. 20, 2003, 5097-5116, vol. 46, No. 24, The American Chemical Society.

Oscar Moradei et al., "Histone Deacetylase Inhibitors: Latest Developments, Trends and Prospects," Curr. Med. Chem.—Anti-Cancer Agents, 2005, 529-560, vol. 5, Bentham Science Publishers Ltd.

Saverio Minucci et al., "Histone deacetylase inhibitors and the promise of epigenetic (and more) treatments for cancer," Nature Reviews—Cancer, Jan. 2006, 38-51, vol. 6, Nature Publishing Group.

Michael Curtin et al., "Histone Deacetylase Inhibitors: The Abbott Experience," Current Medicinal Chemistry, 2003, 2373-2392, vol. 10, Bentham Science Publishers Ltd.

* cited by examiner

CLASS OF HISTONE DEACETYLASE INHIBITORS

PRIORITY CLAIM OR CROSS-REFERENCE TO RELATED PATENT DOCUMENTS

This application is a continuation-in-part of U.S. patent application Ser. No. 12/791,465 filed on Jun. 1, 2010 now U.S. Pat. No. 8,058,273, which is a divisional of application Ser. No. 11/664,187 now U.S. Pat. No. 7,803,800 filed on Mar. 28, 2007, which is a national stage application which claims the benefit of and incorporates by reference essential subject matter disclosed in International Patent Application No. PCT/EP2005/054949 filed on Sep. 30, 2005, which claims the benefit of Italian Patent Application No. MI2004A001869 filed on Oct. 1, 2004. This application is also a continuation of U.S. patent application Ser. No. 12/295,498 filed on Sep. 30, 2008 now abandoned which is a national stage application that claims the benefit of and incorporates by reference essential subject matter disclosed in International Patent Application No. PCT/EP2007/053097 filed on Mar. 30, 2007, which claims the benefit of Italian Patent Application No. MI2006A000621 filed on Mar. 31, 2006.

FIELD OF THE INVENTION

The present invention relates to the field of histone deacetylases (HDACs) inhibiting compounds and methods for using the compounds to treat diseases linked to the disregulation of histone deacetylases activity, in particular for the treatment of cancer.

BACKGROUND OF THE INVENTION

The reversible acetylation of the c-amino groups of several lysine residues in the N-terminal histone tails mediates important conformational modifications in nucleosomes. These modifications influence the access of transcription factor to DNA and regulate gene expression (Davie, J. R. *Curr. Opin. Genet. Dev.* 1998, 8, 173-178). Two enzyme classes are involved in the process of acetylation and deacetylation of histones: histone acetyltransferases (HAT), which catalyse histone acetylation by acting as transcriptional co-activators, and histone deacetylases (HDAC).

After their recruitment to the promoter regions induced by transcription repressors and co-repressors such as Sin3, SMRT and N-CoR, histone deacetylases induce the formation of hypoacetylated histones and ultimately lead to transcriptional silencing (Wu, J. et al. *Trends Biochem. Sci.* 2000, 25, 619-623). The aberrant recruitment of histone deacetylases by oncogene proteins, or the disruption of the equilibrium between the activities of histone acetyltransferases and histone deacetylases are implicated in a series of pathologies, including:

1. Primarily, cancer (Lin, R. J. et al. *Oncogene* 2001, 20, 7204-7215; Kastner, P. et al. *Oncogene* 2001, 20, 7186-7203; Pandolfi, P. et al. *Oncogene* 2001, 20, 3116-3127; Grignani, F. et al. *Nature* 1998, 391, 815-818; Lutterbach, B. et al. *Mol. Cell. Biol.* 1998, 18, 7176-7184).
2. Non-tumor diseases:
Nervous system: Huntington's disease (Ferrante, R. J. et al. *J. Neurosci.* 2003, 23, 9418-9427; Hockey, E. et al. *Proc. Natl. Acad. Sci. USA* 2003, 100, 2041-2046); diseases caused by triplet expansions (Bodai, L. et al. *Curr. Med. Chem.* 2003, 10, 2577-2587; Hughes, R. E. *Curr. Biol.* 2002, 12, R141-143);
neurodegenerative disorders (Jeong, M. R. et al. *FEBS Lett.* 2003, 542, 74-78);
ischemia (Ming, R. et al. *J. Neurochem.* 2004, 89, 1358-1367);
oxidative stress (Ryu, H. et al. *Proc. Natl. Acad. Sci. USA* 2003, 100, 4281-4286);
inflammatory responses of the nervous system (Suuronen, T. J. Neurochem. 2003, 87, 407-416);
epilepsy (Eyal, S. et al. *Epilepsia* 2004, 45, 737-744; Huang, Y. et al. *J. Neurosci.* 2002, 22, 8422-8428);
diseases caused by protein aggregates (Corcoran, L. J. et al. *Curr. Biol.* 2004, 14, 488-492);
Psychic diseases: bipolar disorders (Williams, R. S. B. et al. *Nature* 2002, 417, 292-295);
cognitive disorders (Levenson, J. M. US20060018921);
psychiatric disorders (Costa, E. et al. *Crit. Rev. Neurobiol.* 2003, 15, 121-142);
fragile X syndrome (Chandler, S. P. et al. *BMC Mol. Biol.* 2003, 4, 3; Chiurazzi, P. et al. *Hum. Mol. Genet.* 1999, 8, 2317-2323).
Infections: HIV (Adam, E. et al. *Mol. Cell. Biol.* 2003, 23, 6200-6209; Van Lint, C. et al. *Embo J.* 1996, 15, 1112-1120; Demonte, D. et al. *Biochem. Pharmacol.* 2004, 68, 1231-1238; Ylisastigui, L. et al. *Aids* 2004, 18, 1101-1108); malaria, leishmaniasis, infections by protozoa, fungi, phytotoxic agents, viruses and parasites.
Immune system: autoimmune diseases (Skov, S. et al. *Blood* 2003, 101, 1430-1438); chronic immune reactions against the host (Reddy, P. et al. *Proc. Natl. Acad. Sci. USA* 2004, 101, 3921-3926).
The heart: hypertrophy and cardiac decompensation (Kook, H. et al. *J. Clin. Invest.* 2003, 112, 863-871; McKinsey, T. A. et al. *Novartis Found. Symp.* 2004, 259, 132-141, discussion 141-145, 163-169; Hamamori, Y. et al. *J. Clin. Invest.* 2003, 112, 824-826).
Muscular system: fibrotic skin disease (Rombouts, K. et al. *Exp. Cell. Res.* 2002, 278, 184-197); fibrosis (Niki, T. et al. *Hepatology* 1999, 29, 858-867); spinal and bulbar muscular atrophy (Minamiyama, M. et al. *Hum. Mol. Genet.* 2004, 13, 1183-1192).
Others: arthritis (Chung, Y. L. et al. *Mol. Ther.* 2003, 8, 707-717); hyperlipidemia (Crestani, M. et al. WO05/105066); kidney diseases (Mishra, N. et al. *J. Clin. Invest.* 2003, 111, 539-552); psoriasis (McLaughlin, F. et al. *Curr. Drug Targets Inflamm. Allergy* 2004, 3, 213-219); intestinal and colitic diseases (Saemann, M. D. et al. *Wien. Klin. Wochenschr.* 2002, 114, 289-300); beta thalassemia (Rodgers, G. P. et al. *Expert Opin. Investig. Drugs* 2001, 10, 925-934); respiratory diseases (Barnes, P. J. *Am. J. Respir. Crit. Care Med.* 2003, 167, 813-818), Rubinstein-Taybi syndrome (Alarcon, J. M. et al. *Neuron* 2004, 42, 947-959).

A number of histone deacetylase inhibitors are known, including natural products (e.g. trichostatin A (TSA), trapoxin (TPX), depsipeptide FK-228), short chain fatty acids (sodium-butyrate, -phenylbutyrate and -valproate) hydroxamates (e.g. suberoylanilide (SAHA), pyroxamide, scriptaid, oxamflatin, NVP-LAQ824) cyclic peptides containing hydroxamic acid (CHAPs) and benzamides (e.g. MS-275). All of them potently induce growth arrest, differentiation and apoptosis in a variety of transformed cells in culture as well in animal models (Marks, P. A. et al. *Curr. Opin. Oncol.* 2001, 13, 477-483). Several HDAC inhibitors such as, sodium phenylbutyrate (alone or in combination), depsipeptide, SAHA, pyroxamide, NVP-LAQ824 and MS-275 are being evaluated in clinical studies for the treatment of various tumor diseases (Johnstone, R. W *Nat. Rev. Drug Discov.* 2002, 1, 287-299). Their clinical benefit, however, is limited by toxicity problems (TSA, CHAPs, MS-275), low stability (TSA), low solubility (TSA), poor potency and lack of selectivity (butyrates and analogues) (Vigushin, D. et al. *Anti-Cancer Drugs* 2002, 13, 1-13).

To overcome these liabilities many derivatives have been synthesised based on the structures of the aforesaid compounds, with some molecular sub-structures hypothesised by certain authors as being useful for the activity and penetration of cellular structures (Miller, T. A. *Expert Opin. Ther. Patents* 2004, 14, 791-804; Miller, T. A. *J. Med. Chem.* 2003, 46, 5098-5116; Moradei, O. et al. *Curr. Med. Chem.—Anticancer Agents* 2005, 5, 529-560; Minucci, S. et al. *Nature Reviews Cancer*, 2006 6, 38-51).

WO 06/020004 describes HDAC inhibitors with the following general formula

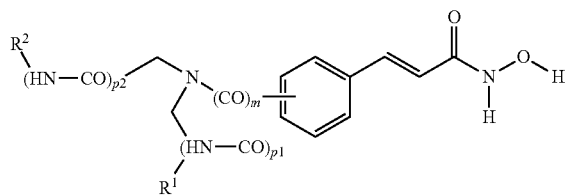

where m, $p^1$ and $p^2$ are 0 or 1, $R^1$ and $R^2$ are, among other groups, $C_1$-$C_{10}$ alkyl, aryl, heteroaryl, $C_1$-$C_{10}$ alkylaryl or $C_1$-$C_{10}$ alkylheteroaryl.

WO 04/063169 describes histone deacetylase inhibitors of general formula

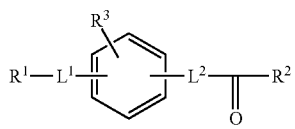

where $R^1$ is an optionally substituted heterocycle which contains a nitrogen, $R^2$ is hydroxylamine, $R^3$ is, among other substituents, hydrogen, $L^1$ is an optionally substituted —$(CH_2)_n$— group with n being between 0 and 6; $L^2$ is an alkenyl chain.

WO 03/087066 describes HDAC inhibitors of general formula:

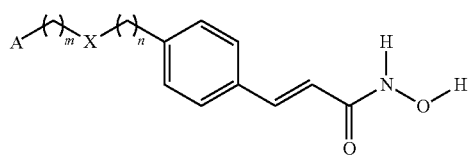

where A is phenyl or an optionally substituted heterocycle; m and n are from 0 to 4; and X can be the following group

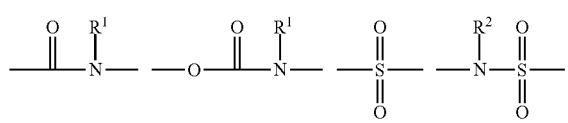

where $R^1$ and $R^2$ are independently hydrogen or an optionally substituted $C_1$-$C_4$ alkyl chain.

WO 95/13264 describes N-hydroxypropenamides of general formula

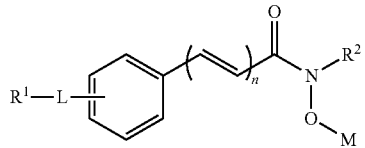

where $R^1$ is, among other groups, phenyl or aryloxyphenyl; L is a $C_1$-$C_8$ alkylene chain, —$(CH_2)_m$—O— (where m is a number from 0 to 4) or —CO—; n is 0 or 1; $R^2$ is hydrogen, $C_1$-$C_4$ alkyl or arylalkyl; M is, among other groups, hydrogen.

In *J. Med. Chem.* 2001, 44, 2069-2072, *J. Med. Chem.* 2002, 45, 1778-1784, *J. Med. Chem.* 2003, 46, 512-524, *J. Med. Chem.* 2003, 46, 4826-4829, *J. Med. Chem.* 2004, 47, 1098-1109, *J. Med. Chem.* 2004, 47, 1351-1359 and *J. Med. Chem.* 2005, 48, 3344-3353, Mai et al. describe a series of pyrrolyl hydroxyamides as selective histone deacetylase inhibitors.

HDAC inhibitors are also described in patent application PCT/EP2005/054949.

Several lines of research are currently ongoing in the field, focused both on the identification of new inhibitors having a broad-ranging action on all histone deacetylases, or inhibitors having a greater activity towards specific HDAC sub-classes.

In addition, based on the clinical and preclinical data of the first HDAC inhibitors and the great therapeutic potential of HDAC inhibition for various pathologies, the need for new inhibitors with improved pharmacological and chemico-physical properties is considerably high.

In particular, compounds endowed with increased inhibitory potency and metabolic stability could be extremely useful therapeutic agents with higher activity and longer duration of effect as compared to known inhibitors.

BRIEF SUMMARY OF THE INVENTION

New histone deacetylase inhibitors have now been identified, endowed with HDAC inhibitory activity and favourable pharmacological properties. Said inhibitors have the general formula (I)

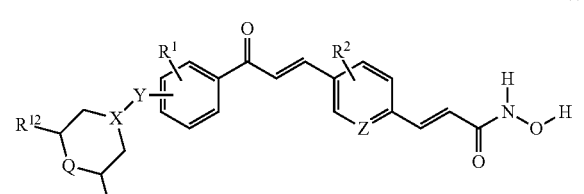

wherein:
Q is a bond, $CH_2$, CH—$NR^3R^4$, $NR^5$ or oxygen;
X is CH or nitrogen;
Y is a bond, $CH_2$, oxygen or $NR^6$;
Z is CH or nitrogen;
$R^1$, $R^2$ are, independently, hydrogen, halogen, $C_1$-$C_6$ alkyl or $C_1$-$C_6$ haloalkyl;
$R^3$, $R^4$ are, independently, hydrogen, $C_1$-$C_6$ alkyl, phenyl or benzyl;
$R^5$ is hydrogen, $C_1$-$C_6$ alkyl, (CO)$R^7$, $SO_2$—$C_1$-$C_6$ alkyl, phenyl or benzyl;

$R^6$ is hydrogen, $C_1$-$C_6$ alkyl or benzyl;
$R^7$ is hydrogen, $C_1$-$C_6$ alkyl, phenyl, benzyl, $OR^8$ or $NR^9R^{10}$;
$R^8$ is $C_1$-$C_6$ alkyl;
$R^9$ is hydrogen, $C_1$-$C_6$ alkyl, phenyl or benzyl;
$R^{10}$ is hydrogen, $C_1$-$C_6$ alkyl or benzyl;
$R^{11}$, $R^{12}$ are, independently, hydrogen or $C_1$-$C_6$ alkyl;
and the pharmaceutically acceptable salts thereof;
with the proviso that when X is nitrogen, Y cannot be oxygen or $NR^6$;
and with the exclusion of the following compounds:
(E)-N-Hydroxy-3-(4-{(E)-3-[4-(4-methyl-piperazin-1-yl)-phenyl]-3-oxo-propenyl}-phenyl)-acrylamide;
(E)-N-Hydroxy-3-{4-[(E)-3-(4-morpholin-4-yl-phenyl)-3-oxo-propenyl]-phenyl}-acrylamide;
(E)-3-{3-Fluoro-4-[(E)-3-(4-morpholin-4-yl-phenyl)-3-oxo-propenyl]-phenyl}-N-hydroxy-acrylamide.

DETAILED DESCRIPTION OF THE INVENTION

In the above described formula (I) as well as in the sub-formulas (Ia), (Ib), (Ic) herebelow disclosed, the following general definitions apply.

The phenyl or benzyl in $R^3$, $R^4$, $R^5$, $R^6$, $R^7$, $R^9$, $R^{10}$, may be optionally substituted with one or more substituents selected from halogen, $C_1$-$C_6$ alkyl, $C_1$-$C_6$ haloalkyl, $C_1$-$C_6$ alkoxy, or $C_1$-$C_6$ haloalkoxy.

"Acceptable pharmaceutical salts" comprise salts obtained by salification with inorganic acids (e.g. hydrochloric, hydrobromide, sulfuric or phosphoric acids), or with organic acids (e.g. acetic, propionic, benzoic, cinnamic, mandelic, salicylic, glycolic, lactic, oxalic, malic, maleic, malonic, fumaric, tartaric, citric, p-toluenesulfonic or methanesulfonic acids).

All the "alkyl" chains and alkyl-containing chains (e.g. haloalkyl) can be linear or branched.

"Halogens" are preferably fluorine, chlorine or bromine, being in particular fluorine or chlorine.

The "$C_1$-$C_6$ alkyl" group is preferably a linear or branched $C_1$-$C_4$ alkyl group, more preferably a $C_1$-$C_2$ alkyl group.

The "$C_1$-$C_6$ alkoxy" group is preferably a linear or branched $C_1$-$C_4$ alkoxy group, more preferably a $C_1$-$C_2$ alkoxy group.

The "$C_1$-$C_6$ haloalkoxy" group is preferably a linear or branched $C_1$-$C_4$ haloalkoxy group, more preferably a $C_1$-$C_2$ haloalkoxy group.

The "$C_1$-$C_6$ haloalkyl" group is preferably a linear or branched $C_1$-$C_4$ haloalkyl group, more preferably a $C_1$-$C_2$ haloalkyl group, being in particular $CF_3$.

The present invention comprises all possible isomers of said formulas (I), (Ia), (Ib) or (Ic) and mixtures thereof, and the metabolic precursors of formula (I) compounds. The term "metabolic precursors" means compounds having a different structure from that of the relevant formulas (I), (Ia), (Ib) or (Ic), which after administration to the patient are directly or indirectly transformed into a compound of said formula (I), (Ia), (Ib) or (Ic). Methods for selecting metabolic precursors and their relative preparation are described for example in the book by Bundgaard (Bundgaard, H. ed., "Design of Prodrugs", Elsevier, 1985).

All compounds of present formula (I) show useful HDAC inhibiting activity.

Furthermore, within the scope of the general formula (I), the present inventors have identified three sub-groups of compounds identified by formulas (Ia), (Ib) and (Ic) as herebelow defined. The compounds of these three sub-groups are characterised by a particularly high HDAC inhibiting activity, and a high resistance to metabolic inactivation; these three sub-groups represent particular embodiments of the invention.

A first embodiment is thus represented by the compounds of formula (Ia)

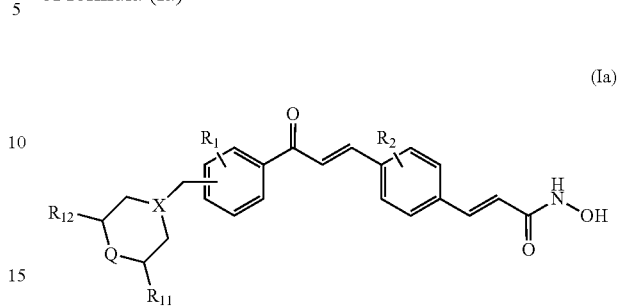

(Ia)

wherein:
Q is $CH_2$, CH—$NR^3R^4$, or $NR^5$;
X is CH or nitrogen;
$R^1$, $R^2$ are, independently, hydrogen, halogen, $C_1$-$C_4$ alkyl, or $C_1$-$C_4$ haloalkyl;
$R^3$, $R^4$ are, independently, hydrogen or $C_1$-$C_4$ alkyl;
$R^5$ is hydrogen, $C_1$-$C_4$ alkyl, (CO)$R^7$, phenyl or benzyl;
$R^7$ is hydrogen, $C_1$-$C_6$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_4$ alkyl;
$R^{11}$, $R^{12}$ are, independently, hydrogen or $C_1$-$C_4$ alkyl.

As evident from comparison with formula (I), in formula (Ia) Y is only $CH_2$ and Z is only CH; further limitations are present with respect to the remaining radicals.

Preferably, within said formula (Ia), the shown radicals have the following meanings:
Q is $CH_2$, CH—$NR^3R^4$, or $NR^5$;
X is CH or nitrogen;
$R^1$, $R^2$ are, independently, hydrogen, fluoro, chloro, or $CF_3$;
$R^3$, $R^4$ are, independently, hydrogen or $C_1$-$C_2$ alkyl;
$R^5$ is hydrogen, $C_1$-$C_4$ alkyl, (CO)$R^7$, phenyl or benzyl;
$R^7$ is hydrogen, $C_1$-$C_4$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_2$ alkyl;
$R^{11}$, $R^{12}$ are, independently, hydrogen or $C_1$-$C_2$ alkyl.

Even more preferably, within said formula (Ia), the shown radicals have the following meanings:
Q is $NR^5$;
X is nitrogen;
$R^1$, $R^2$ are, independently, hydrogen, fluoro, chloro or $CF_3$;
$R^5$ is hydrogen, $C_1$-$C_4$ alkyl, (CO)$R^7$, phenyl or benzyl;
$R^7$ is hydrogen, $C_1$-$C_4$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_2$ alkyl;
$R^{11}$, $R^{12}$ are, independently, hydrogen or $C_1$-$C_2$ alkyl.

According this last implementation mode, the X/Q containing ring of formula (I) is always a piperazine ring.

A second embodiment is represented by the compounds of formula (Ib)

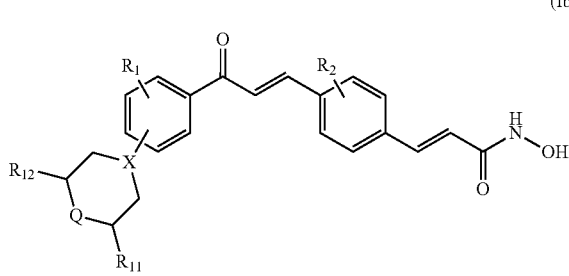

wherein:
Q is CH$_2$, CH—NR$^3$R$^4$, or NR$^5$;
X is CH or nitrogen;
R$^1$, R$^2$ are, independently, hydrogen, halogen, C$_1$-C$_4$ alkyl or C$_1$-C$_4$ haloalkyl;
R$^3$, R$^4$ are, independently, hydrogen or C$_1$-C$_4$ alkyl;
R$^5$ is hydrogen, C$_1$-C$_4$ alkyl, (CO)R$^7$, SO$_2$—C$_1$-C$_4$ alkyl, phenyl or benzyl;
R$^7$ is hydrogen, C$_1$-C$_6$ alkyl, phenyl, benzyl, OR$^8$ or NR$^9$R$^{10}$;
R$^8$ is C$_1$-C$_4$ alkyl;
R$^9$, R$^{10}$ are, independently, hydrogen or C$_1$-C$_4$ alkyl;
R$^{11}$, R$^{12}$ are, independently, hydrogen or C$_1$-C$_4$ alkyl;
with the exclusion of the following compound:
(E)-N-Hydroxy-3-(4-{(E)-3-[4-(4-methyl-piperazin-1-yl)-phenyl]-3-oxo-propenyl}-phenyl)-acrylamide.

As evident from comparison with formula (I), in formula (Ib) Y is only a bond and Z is only CH; further limitations are present with respect to the remaining radicals.

Preferably, within said formula (Ib), the group:

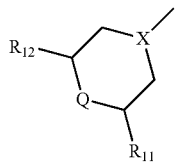

is in ortho or meta position with respect to the 3-oxo-propenyl moiety (i.e. the Y-radical and the 3-oxo-propenyl radical are attached on the R$_1$-containing ring in ortho or meta relation with each other), and the other radicals have the following meanings:
Q is CH$_2$ or NR$^5$;
X is CH or nitrogen;
R$^1$, R$^2$ are, independently, hydrogen, fluoro, chloro or CF$_3$;
R$^5$ is hydrogen, C$_1$-C$_4$ alkyl, (CO)R$^7$, phenyl or benzyl;
R$^7$ is hydrogen, C$_1$-C$_4$ alkyl, phenyl, benzyl, OR$^8$ or NR$^9$R$^{10}$;
R$^8$ is C$_1$-C$_4$ alkyl;
R$^9$, R$^{10}$ are, independently, hydrogen or C$_1$-C$_2$ alkyl;
R$^{11}$, R$^{12}$ are, independently, hydrogen or C$_1$-C$_2$ alkyl.

A third embodiment is represented by the compounds of formula (Ic)

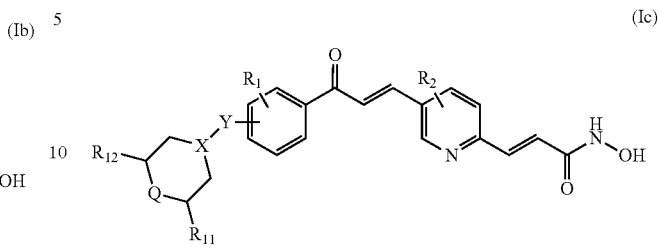

wherein:
Q is CH$_2$, CH—NR$^3$R$^4$, NR$^5$ or oxygen;
X is CH or nitrogen;
Y is a bond, CH$_2$, oxygen or NR$^6$;
R$^1$, R$^2$ are, independently, hydrogen, halogen, C$_1$-C$_4$ alkyl, or C$_1$-C$_4$ haloalkyl;
R$^3$, R$^4$ are, independently, hydrogen or C$_1$-C$_4$ alkyl;
R$^5$ is hydrogen, C$_1$-C$_4$ alkyl, (CO)R$^7$, phenyl or benzyl;
R$^6$ is hydrogen or C$_1$-C$_4$ alkyl;
R$^7$ is hydrogen, C$_1$-C$_6$ alkyl, phenyl, benzyl, OR$^8$ or NR$^9$R$^{10}$;
R$^8$ is C$_1$-C$_4$ alkyl;
R$^9$, R$^{10}$ are, independently, hydrogen or C$_1$-C$_4$ alkyl;
R$^{11}$, R$^{12}$ are, independently, hydrogen or C$_1$-C$_4$ alkyl;
provided that when X is nitrogen, Y cannot be oxygen or NR$^6$.

As evident from comparison with formula (I), in formula (Ic) Z is only nitrogen; further limitations are present with respect to the remaining radicals. Preferably, within said formula (Ic), the shown radicals have the following meanings:
Q is CH$_2$, NR$^5$ or oxygen;
X is CH or nitrogen;
Y is a bond or CH$_2$;
R$^1$, R$^2$ are, independently, hydrogen, fluoro, chloro or CF$_3$;
R$^5$ is hydrogen, C$_1$-C$_2$ alkyl, (CO)R$^7$, phenyl or benzyl;
R$^7$ is hydrogen, C$_1$-C$_4$ alkyl, phenyl, benzyl, OR$^8$ or NR$^9$R$^{10}$;
R$^8$ is C$_1$-C$_4$ alkyl;
R$^9$, R$^{10}$ are, independently, hydrogen or C$_1$-C$_2$ alkyl;
R$^{11}$, R$^{12}$ are, independently, hydrogen or C$_1$-C$_2$ alkyl.

All compounds of said formulas (I), (Ia), (Ib), (Ic), possess HDAC inhibitory activity. In particular, as shown in the experimental section, the compounds of formulas (Ia), (Ib), (Ic) show surprisingly a remarkable higher HDAC inhibitory activity, and a higher resistance to metabolic inactivation.

Preferred compounds belonging to both formulas (I) and (Ia) are the following:
(E)-N-Hydroxy-3-(4-{(E)-3-[4-(4-methyl-piperazin-1-ylmethyl)-phenyl]-3-oxo-propenyl}-phenyl)-acrylamide; (example 7)
(E)-3-(4-{(E)-3-[4-(4-Dimethylamino-piperidin-1-yl-methyl)-phenyl]-3-oxo-propenyl}-phenyl)-N-hydroxy-acrylamide; (example 9)
(E)-N-Hydroxy-3-(4-{(E)-3-[4-(1-methyl-piperidin-4-ylmethyl)-phenyl]-3-oxo-propenyl}-phenyl)-acrylamide; (example 23)
(E)-N-Hydroxy-3-{4-[(E)-3-oxo-3-(4-piperazin-1-ylmethyl-phenyl)-propenyl]-phenyl}-acrylamide; (example 26)
(E)-3-(4-{(E)-3-[4-(4-Benzyl-piperazin-1-ylmethyl)-phenyl]-3-oxo-propenyl}-phenyl)-N-hydroxy-acrylamide; (example 27)
(E)-3-(4-{(E)-3-[4-((3R,5S)-3,5-Dimethyl-piperazin-1-ylmethyl)-phenyl]-3-oxo-propenyl}-phenyl)-N-hydroxy-acrylamide; (example 29)
(E)-3-(4-{(E)-3-[4-(4-Acetyl-piperazin-1-ylmethyl)-phenyl]-3-oxo-propenyl}-phenyl)-N-hydroxy-acrylamide; (example 30)

(E)-3-(4-{(E)-3-[4-((3R,5S)-4-Acetyl-3,5-dimethyl-piperazin-1-ylmethyl)-phenyl]-3-oxo-propenyl}-phenyl)-N-hydroxy-acrylamide; (example 31)

(E)-3-(4-{(E)-3-[4-(4-Ethyl-piperazin-1-ylmethyl)-phenyl]-3-oxo-propenyl}-phenyl)-N-hydroxy-acrylamide; (example 32)

(E)-N-Hydroxy-3-(4-{(E)-3-[3-(4-methyl-piperazin-1-ylmethyl)-phenyl]-3-oxo-propenyl}-phenyl)-acrylamide; (example 34)

(E)-N-Hydroxy-3-(4-{(E)-3-[2-(4-methyl-piperazin-1-ylmethyl)-phenyl]-3-oxo-propenyl}-phenyl)-acrylamide; (example 35)

Preferred compounds belonging to both formulas (I) and (Ib) are the following:

(E)-N-Hydroxy-3-(4-{(E)-3-[2-(4-methyl-piperazin-1-yl)-phenyl]-3-oxo-propenyl}-phenyl)-acrylamide (example 1)

(E)-N-Hydroxy-3-(4-{(E)-3-[3-(4-methyl-piperazin-1-yl)-phenyl]-3-oxo-propenyl}-phenyl)-acrylamide; (example 2)

(E)-N-Hydroxy-3-(4-{(E)-3-[4-(4-methylamino-piperidin-1-yl)-phenyl]-3-oxo-propenyl}-phenyl)-acrylamide; (example 3)

(E)-3-(4-{(E)-3-[4-(4-Dimethylamino-piperidin-1-yl)-phenyl]-3-oxo-propenyl}-phenyl)-N-hydroxy-acrylamide; (example 4)

(E)-N-Hydroxy-3-(4-{(E)-3-[4-(1-methyl-piperidin-4-yl)-phenyl]-3-oxo-propenyl}-phenyl)-acrylamide; (example 10)

(E)-N-Hydroxy-3-(4-{(E)-3-[4-(4-isobutyl-piperazin-1-yl)-phenyl]-3-oxo-propenyl}-phenyl)-acrylamide; (example 12)

(E)-3-(4-{(E)-3-[4-(4-Ethyl-piperazin-1-yl)-phenyl]-3-oxo-propenyl}-phenyl)-N-hydroxy-acrylamide; (example 13)

(E)-3-(4-{(E)-3-[4-(4-Benzyl-piperazin-1-yl)-phenyl]-3-oxo-propenyl}-phenyl)-N-hydroxy-acrylamide; (example 14)

(E)-N-Hydroxy-3-{4-[(E)-3-(4-piperazin-1-yl-phenyl)-3-oxo-propenyl]-phenyl}-acrylamide; (example 15)

(E)-3-(4-{(E)-3-[4-(4-Benzoyl-piperazin-1-yl)-phenyl]-3-oxo-propenyl}-phenyl)-N-hydroxy-acrylamide; (example 16)

(E)-3-(4-{(E)-3-[4-(4-Acetyl-piperazin-1-yl)-phenyl]-3-oxo-propenyl}-phenyl)-N-hydroxy-acrylamide; (example 17)

(E)-N-Hydroxy-3-(4-{(E)-3-[4-(4-methanesulfonyl-piperazin-1-yl)-phenyl]-3-oxo-propenyl}-phenyl)-acrylamide; (example 18)

4-(4-{(E)-3-[4-((E)-2-Hydroxycarbamoyl-vinyl)-phenyl]-acryloyl}-phenyl)-piperazine-1-carboxylic acid dimethylamide; (example 19)

4-(4-{(E)-3-[4-((E)-2-Hydroxycarbamoyl-vinyl)-phenyl]-acryloyl}-phenyl)-piperazine-1-carboxylic acid amide; (example 20)

4-(4-{(E)-3-[4-((E)-2-Hydroxycarbamoyl-vinyl)-phenyl]-acryloyl}-phenyl)-piperazine carboxylic acid ethyl ester; (example 21)

(E)-N-Hydroxy-3-(4-{(E)-3-oxo-3-[4-((3R,5S)-3,4,5-trimethyl-piperazin-1-yl)-phenyl]-propenyl}-phenyl)-acrylamide; (example 24)

(E)-3-(4-{(E)-3-[3-Chloro-5-(4-methyl-piperazin-1-yl)-phenyl]-3-oxo-propenyl}-phenyl)-N-hydroxy-acrylamide; (example 25)

(E)-3-(4-{(E)-3-[5-Chloro-2-(4-methyl-piperazin-1-yl)-phenyl]-3-oxo-propenyl}-phenyl)-N-hydroxy-acrylamide; (example 46)

(E)-3-(4-{(E)-3-[2-Chloro-5-(4-methyl-piperazin-1-yl)-phenyl]-3-oxo-propenyl}-phenyl)-N-hydroxy-acrylamide (example 51)

Preferred compounds belonging to both formulas (I) and (Ic) are the following:

(E)-N-Hydroxy-3-(5-{(E)-3-[4-(4-methyl-piperazin-1-yl)-phenyl]-3-oxo-propenyl}-pyridin-2-yl)-acrylamide; (example 11)

(E)-N-Hydroxy-3-(5-{(E)-3-[2-(4-methyl-piperazin-1-yl)-phenyl]-3-oxo-propenyl}-pyridin-2-yl)-acrylamide; (example 36)

(E)-N-Hydroxy-3-(5-{(E)-3-[3-(4-methyl-piperazin-1-yl)-phenyl]-3-oxo-propenyl}-pyridin-2-yl)-acrylamide; (example 37)

(E)-3-(5-{(E)-3-[4-(4-Benzyl-piperazin-1-yl)-phenyl]-3-oxo-propenyl}-pyridin-2-yl)-N-hydroxy-acrylamide; (example 38)

(E)-N-Hydroxy-3-(5-{(E)-3-oxo-3-[4-((3R,5S)-3,4,5-trimethyl-piperazin-1-yl)-phenyl]-propenyl}-pyridin-2-yl)-acrylamide; (example 39)

(E)-N-Hydroxy-3-{5-[(E)-3-(4-morpholin-4-ylmethyl-phenyl)-3-oxo-propenyl]-pyridin-2-yl}-acrylamide; (example 40)

(E)-3-(5-{(E)-3-[4-(4-Ethyl-piperazin-1-yl)-phenyl]-3-oxo-propenyl}-pyridin-2-yl)-N-hydroxy-acrylamide; (example 41)

(E)-3-(5-{(E)-3-[4-(4-Acetyl-piperazin-1-yl)-phenyl]-3-oxo-propenyl}-pyridin-2-yl)-N-hydroxy-acrylamide; (example 42)

(E)-N-Hydroxy-3-(5-{(E)-3-oxo-3-[3-((3R,5S)-3,4,5-trimethyl-piperazin-1-yl)-phenyl]-propenyl}-pyridin-2-yl)-acrylamide; (example 43)

(E)-N-Hydroxy-3-(5-{(E)-3-[4-(1-methyl-piperidin-4-ylmethyl)-phenyl]-3-oxo-propenyl}-pyridin-2-yl)-acrylamide; (example 44)

(E)-N-Hydroxy-3-{5-[(E)-3-oxo-3-(4-piperazin-1-yl-phenyl)-propenyl]-pyridin-2-yl}-acrylamide; (example 45)

(E)-N-Hydroxy-3-(5-{(E)-3-[2-(4-methyl-piperazin-1-ylmethyl)-phenyl]-3-oxo-propenyl}-pyridin-2-yl)-acrylamide; (example 47)

(E)-N-Hydroxy-3-{5-[(E)-3-oxo-3-(4-piperazin-1-ylmethyl-phenyl)-propenyl]-pyridin-2-yl}-acrylamide; (example 48)

(E)-3-(5-{(E)-3-[4-(4-Acetyl-piperazin-1-ylmethyl)-phenyl]-3-oxo-propenyl}-pyridin-2-yl)-N-hydroxy-acrylamide; (example 49)

(E)-N-Hydroxy-3-(5-{(E)-3-[4-(4-methyl-piperazin-1-ylmethyl)-phenyl]-3-oxo-propenyl}-pyridin-2-yl)-acrylamide (example 50)

(E)-3-(5-{(E)-3-[3-Chloro-5-(4-methyl-piperazin-1-yl)-phenyl]-3-oxo-propenyl}-pyridin-2-yl)-N-hydroxy-acrylamide (example 52)

(E)-N-Hydroxy-3-(5-{(E)-3-[3-(4-methyl-piperazin-1-ylmethyl)-phenyl]-3-oxo-propenyl}-pyridin-2-yl)-acrylamide (example 53).

Further preferred compounds belonging to formula (I) are the following:

(E)-N-Hydroxy-3-(4-{(E)-3-[4-(1-methyl-piperidin-4-ylamino)-phenyl]-3-oxo-propenyl}-phenyl)-acrylamide (example 5)

(E)-N-Hydroxy-3-[4-(E)-3-{4-[N-methyl-(1-methyl-piperidin-4-yl)-amino]-phenyl}-3-oxo-propenyl)-phenyl]-acrylamide (example 6)

(E)-N-Hydroxy-3-(4-{(E)-3-[4-(1-methyl-piperidin-4-yloxy)-phenyl]-3-oxo-propenyl}-phenyl)-acrylamide (example 22).

The present invention also comprises the process for preparing the compounds of formula (I), (Ia), (Ib), (Ic). These compounds can be synthesized by treating a compound of formula (II):

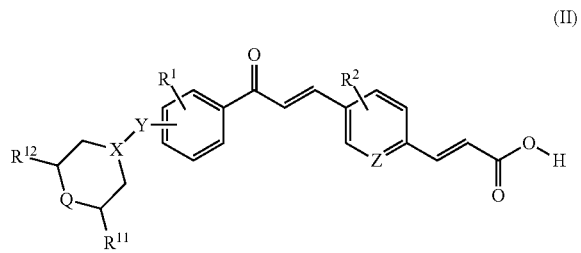

(II)

where Q, X, Y, Z, $R^1$, $R^2$, $R^{11}$, $R^{12}$ have the aforedescribed meanings, with a protected hydroxylamine such as O-(tetrahydro-2H-piran-2-yl)hydroxylamine ($NH_2OTHP$), followed by a deprotection step to give the corresponding hydroxylamine.

The reaction of the compound of formula (II) with the protected hydroxylamine can be carried out with condensation agents such as EDC (1-(3-dimethylaminopropyl)-3-ethylcarbodiimide), in the presence of a suitable base (e.g. triethylamine or di-isopropylethylamine) in a suitable solvent (e.g. tetrahydrofuran, dichloromethane or DMF). Generally an activator of the condensation reaction, such as HOBT (1-hydroxybenzotriazole) or HOAT (1-hydroxy-7-aza-benzotriazole), can be added to the reaction mixture. The reaction can be carried out at room temperature for a period lasting between about 2 and 12 hours. Deprotection of the hydroxylamine, in the case of tetrahydropyranyl, can be achieved by known methods, for example using HCl in aprotic solvents (such as THF, diethylether or dioxane).

The compounds of formula (II) can be synthesized by treating a compound of formula (III),

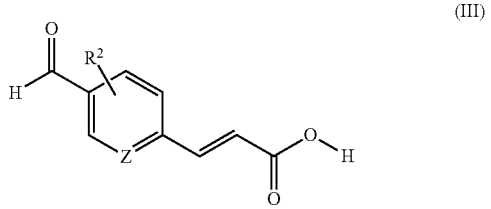

(III)

where $R^2$ and Z have the aforesaid meanings, with a compound of formula (IV),

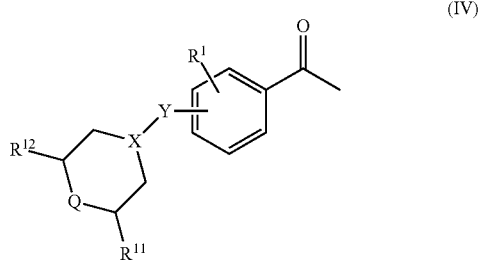

(IV)

where Q, X, Y, $R^1$, $R^{11}$, $R^{12}$ have the aforesaid meanings.

The compounds of formula (II) where Q is $NCOR^7$ (where $R^7$ is hydrogen, $C_1$-$C_6$ alkyl, phenyl, benzyl or $OR^8$, with $R^8$ as aforedefined) can also be synthesized by treating a compound of formula (V)

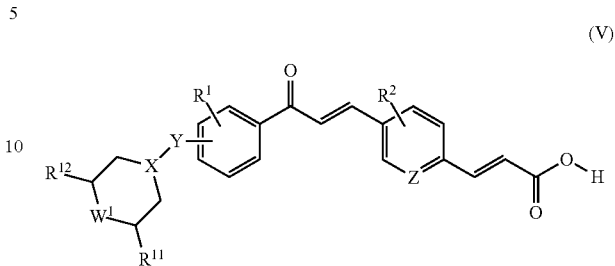

(V)

(where X, Y, $R^1$, $R^2$, $R^{11}$, $R^{12}$ and Z have the aforesaid meanings and $W^1$ is NH) with a compound of formula (VI) $R^7COA$, where $R^7$ is hydrogen, $C_1$-$C_6$ alkyl, phenyl, benzyl or $OR^8$ (with $R^8$ as aforedefined) and A is a halogen or a O-EWG group where EWG indicates an electron-attracting group, such as a p-toluenesulfonic or methanesulfonic group, or benzotriazole if $R^7CO$ is formyl. The compounds of formula (II), in which Q is equal to $NR^5$, with $R^5$ equal to $C_1$-$C_6$ alkyl or benzyl, can also be synthesized by treating a compound of formula (V) with a compound of formula (VII) $R^5A$ or with a compound of formula (VIII) $R^{13}CHO$, where $R^5$ is $C_1$-$C_6$ alkyl or benzyl, the benzyl being optionally substituted by one or more substituents chosen from halogen, $C_1$-$C_6$ alkyl, halo-$C_1$-$C_6$ alkyl, $C_1$-$C_6$ alkoxy or halo-$C_1$-$C_6$ alkoxy, A is a halogen or a O-EWG group, where EWG indicates an electron-attracting group, such as a p-toluenesulfonic or methanesulfonic group, and $R^{13}$ is a $C_1$-$C_5$ alkyl or phenyl, the phenyl being optionally substituted by one or more substituents chosen from halogen, $C_1$-$C_6$ alkyl, halo-$C_1$-$C_6$ alkyl, $C_1$-$C_6$ alkoxy or halo-$C_1$-$C_6$ alkoxy.

To obtain compounds of formula (II) with Q equal to $NCONR^9R^{10}$, where $R^9$ has the aforementioned meanings and $R^{10}$ is hydrogen, a compound of formula (V) is treated with a compound of formula (IX) $R^9N=C=O$, where $R^9$ has the aforelisted meanings; otherwise, to obtain compounds of formula (II) with Q equal to $NCONR^9R^{10}$, where $R^9$ has the aforesaid meanings and $R^{10}$ is different from hydrogen, a compound of formula (V) is first treated with a compound of formula (IX) and then with a compound of formula (X) $R^{10}A$, where $R^{10}$ has the aforelisted meanings and A is a halogen or a 0-EWG group, where EWG indicates an electron-attracting group, such as a p-toluenesulfonic or methanesulfonic group.

The compounds of formula (II) where Q is $CH-NR^3R^4$, where $R^3$ and $R^4$ have the aforesaid meanings, can also be synthesized by treating a compound of formula (XI)

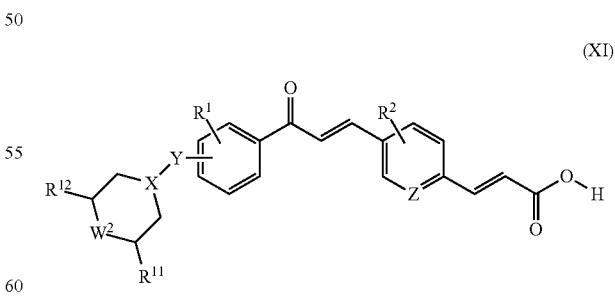

(XI)

where X, Y, $R^1$, $R^2$, $R^{11}$, $R^{12}$ and Z have the aforesaid meanings and $W^2$ is CO, with a compound $HNR^3R^4$, where $R^3$ and $R^4$ have the aforesaid meanings.

The reaction between a compound of formula (III) and one of formula (IV), with Q being different from $N(CO)R^7$, can be carried out in the presence of an inorganic base in a protic solvent, such as water, methanol or ethanol, at a temperature between 0° C. and 25° C. and for a reaction time between about 2 and 36 hours.

The reaction between a compound of formula (V) and one of formula (VI) can be carried out in the presence of a suitable base (such as triethylamine, di-isopropylethylamine) in a suitable solvent (e.g. tetrahydrofuran) at a temperature between about 0° C. and room temperature.

The reaction between a compound of formula (V) and one of formula (VII) is an alkylation process and can be carried out in a suitable organic solvent (e.g. tetrahydrofuran, dichloromethane or diethylether) in the presence of a suitable base (such as triethylamine, di-isopropylethylamine) at a temperature between about 0° C. and 50° C. The preferred halogen is bromine or iodine.

The reactions between the compound of formula (V) and the compound of formula (VIII) and between the compound of formula (XI) and $HNR^3R^4$ are reductive amination processes and can be carried out, preferably under nitrogen atmosphere, in a suitable organic solvent (e.g. methanol, ethanol or tetrahydrofuran) at a temperature between about 0 and 70° C. in the presence of a reducing agent such as $NaBH_4$, $Na(CH_3CO_2)_3BH$ or $NaBH_3CN$. If necessary titanium tetraisopropylate or molecular sieves can be added to facilitate the reaction.

The reaction between the compound of formula (V) and the compound of formula (IX) can be carried out in a suitable organic solvent (e.g. tetrahydrofuran, dichloromethane or diethylether) at a temperature between about 0° C. and room temperature.

The alkylation of the product of the reaction of a compound of formula (V) with a compound of formula (IX) and with a compound of formula (X) can be carried out in a suitable organic solvent (e.g. tetrahydrofuran, dichloromethane or diethylether) at a temperature between about 0° C. and 50° C. The preferred halogen is bromine or iodine.

The compounds of formula (V) and the compounds of formula (XI) can be prepared in a similar method to that previously described for the reaction between compounds of formula (III) and compounds of formula (IV), starting from compounds of formula (III) and from compounds of formula (XII) or formula (XIII).

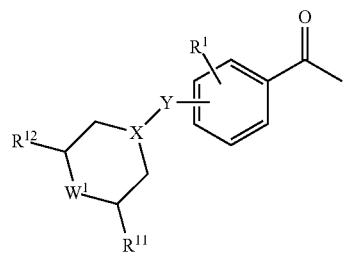

(XII)

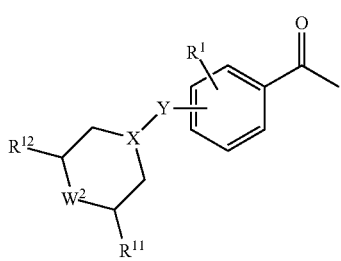

(XIII)

where $W^1$, $W^2$, X, Y, $R^1$, $R^{11}$, $R^{12}$ have the aforesaid meanings.

The compounds of formula (III) are commercial products or can be synthesized by treating a compound of formula (XIV),

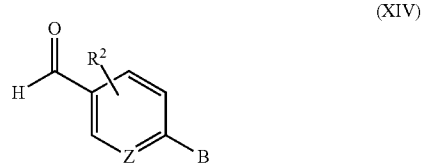

(XIV)

(where Z and $R^2$ have the aforesaid meanings and B is halogen, in particular bromine or iodine) with tert-butylacrylate according the Heck reaction. The reaction conditions are described for example in the book by Larhed and Hallberg (Larhed, M.; Hallberg, A. "Handbook of Organopalladium Chemistry for Organic Synthesis", Negishi, E., Ed.; Wiley-Interscience, 2002). The reaction can be carried out in a suitable organic solvent (e.g. DMF) in the presence of palladium salts (e.g. palladium acetate), organic or inorganic bases (e.g. triethylamine, 1,4-diazabicyclo[2,2,2]-octane, sodium or potassium carbonate) and phosphine ligand derivatives, such as triphenylphosphine, at a temperature between room temperature and about 140° C.

Otherwise, the compounds of formula (III), where Z is nitrogen, can be synthesized by treating a compound of formula (XV)

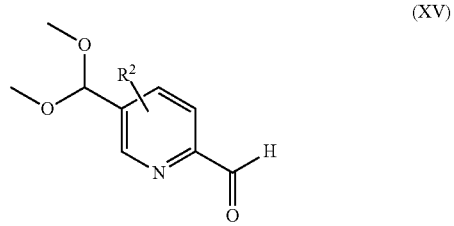

(XV)

where $R^2$ has the aforesaid meaning, with tert-butyl diethylphosphono acetate in the presence of an inorganic base, e.g. NaH, in an aprotic solvent, such as tetrahydrofuran, at a temperature between about 0° C. and room temperature. The deprotection of the tert-butyl group can be achieved by known methods.

The compounds of formula (XV) can be synthesized by treating a compound of formula (XVI)

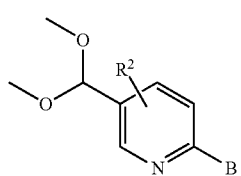

(XVI)

where B and $R^2$ have the aforesaid meaning, firstly with alkyl lithium, e.g. n-butyl-lithium, then with DMF in an aprotic solvent (e.g. THF) at a temperature between about −78° C. and room temperature between 1 and 3 hours.

The compounds of formula (IV) are known products or can be obtained by treating a compound of formula (XVII)

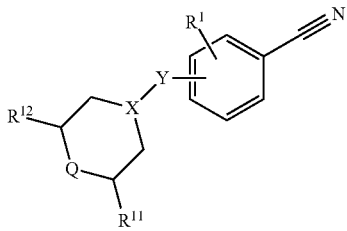

(XVII)

where Q, X, Y, $R^1$, $R^{11}$, $R^{12}$ have the aforesaid meanings provided that Q is different from $N(CO)R^7$, with methyl magnesium bromide.

The compounds of formula (IV) can also be synthesized by treating a compound of formula (XVIII)

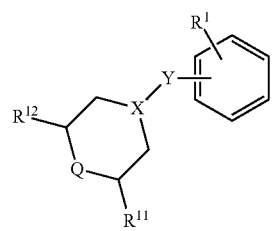

(XVIII)

where Q, X, Y, $R^1$, $R^{11}$, $R^{12}$ have the aforesaid meanings, with acetyl chloride in the presence of a Lewis acid ($AlCl_3$).

The compounds of formula (IV) with Q being equal to $NCOR^7$, where $R^7$ is hydrogen, $C_1$-$C_6$ alkyl, phenyl, benzyl or $OR^8$, with $R^8$ as aforedefined, can also be synthesized by treating a compound of formula (XII) with a compound of formula (VI) $R^7COA$, where $R^7$ is $C_1$-$C_6$ alkyl, phenyl, benzyl or $OR^8$ and A is a halogen or a O-EWG group where EWG indicates an electron-attracting group, such as a p-toluenesulfonic or methanesulfonic group, or benzotriazole if $R^7CO$ is formyl.

The compounds of formula (IV) where Q is $NR^5$, with $R^5$ being equal to $C_1$-$C_6$ alkyl or benzyl, can also be synthesized by treating a compound of formula (XII) with a compound of formula (VII).

The compounds of formula (IV) where Q is $CHNR^3R^4$, where $R^3$ and $R^4$ have the aforesaid meanings, can also be synthesized by treating a compound of formula (XIII) with a compound $HNR^3R^4$, where $R^3$ and $R^4$ have the aforesaid meanings.

The reaction between the compound of formula (XVII) and methyl magnesium bromide can be carried out under inert atmosphere in a suitable organic solvent (e.g. tetrahydrofuran or diethylether) at a temperature between about 0° C. and the boiling point of the chosen solvent.

The reaction between the compound of formula (XVIII) and acetyl chloride can be carried out in the presence of a stoichiometric quantity of a Lewis acid (e.g. $AlCl_3$) under inert atmosphere and in a suitable organic solvent (e.g. dichloromethane or hexane) at a temperature between about 0° C. and the boiling point of the chosen solvent.

The reactions between the compound of formula (XII) and the compound of formula (VI) or with a compound of formula (VII) can be carried out under the same conditions as the reaction between a compound of the aforedescribed formula (V) and a compound of the aforedescribed formula (VI) or (VII).

The reaction between the compound of formula (XIII) and $HNR^3R^4$ can be carried out under the same conditions as the reaction between a compound of the aforedescribed formula (XI) and $HNR^3R^4$.

The compounds of formula (XVII) are known products or, if Y is a bond and X is N, they can be obtained by treating a compound of formula (XIX)

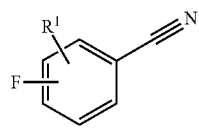

(XIX)

where $R^1$ has the aforesaid meaning and F is a fluorine atom, with a compound of formula (XX)

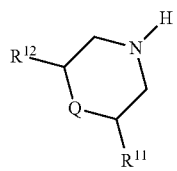

(XX)

where $R^{11}$, $R^{12}$ and Q have the aforesaid meaning.

Otherwise, to obtain compounds of formula (XVII), where Y is $CH_2$ and X is N, a compound of formula (XXI)

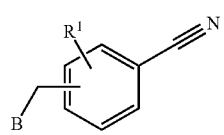

(XXI)

where $R^1$ has the aforesaid meaning and B is a chlorine, bromine, or iodine atom, is treated with a compound of formula (XX).

The reaction between the compound of formula (XIX) and the compound of formula (XX) can be carried out in the presence of a base (e.g. potassium carbonate) in a suitable organic solvent (e.g. DMSO) at a temperature between about room temperature and 150° C.

The reaction between the compound of formula (XXI) and the compound of formula (XX) can be carried out under the same conditions as for the reaction between a compound of formula (V) and a compound of formula (VII).

Alternatively, a compound of formula (IV), wherein Y is $CH_2$ and X is CH, can be obtained by treating a compound of formula (XXII) with methyl magnesium bromide and then by reducing it with hydrogen using Pd/C as a catalyst.

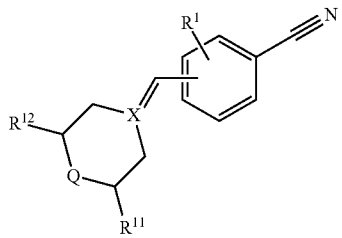

(XXII)

wherein $R^1$, $R^{11}$, $R^{12}$ and Q are as defined above and X is C.

Compound of formula (XXII) can be obtained by treating a compound of formula (XXI) with triethyl phosphite and then with a compound of formula (XXIII)

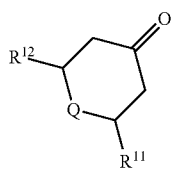

(XXIII)

wherein $R^{11}$, $R^{12}$ and Q are as defined above.

The reaction between a compound of formula (XXII) and methylmagnesium bromide can be carried out in an inert atmosphere in an appropriate organic solvent, such as tetrahydrofuran or diethylether, at a temperature ranging from room temperature to the boiling point of the solvent. The hydrogenation can be carried out in an appropriate organic solvent, such as an alcohol, in the presence of a catalyst, for example Pd/C at a pressure ranging from atmospheric pressure to 100 bars.

The reaction of a compound of formula (XXI) and triethyl phosphite can be carried out in an appropriate solvent, for example THF at a temperature ranging from room temperature to the boiling point of the solvent. The subsequent Horner-Emmons reaction with a compound of formula (XXIII) can be carried out in an appropriate solvent, for example THF or dioxan and using an appropriate base, for example NaH or BuLi, under an inert atmosphere.

Alternatively, a compound of formula (IV) with Y equal to oxygen can be obtained by treating a compound of formula (XXIV)

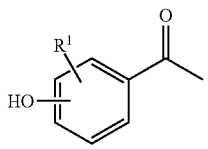

(XXIV)

wherein $R^1$ is defined above, with a compound of formula (XXV)

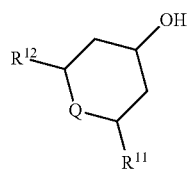

(XXV)

wherein $R^{11}$, $R^{12}$ and Q are as defined above, in the presence of $PPh_3$ and diethylazodicarboxylate in a suitable solvent, for example THF or toluene, at a temperature ranging from 0° C. to the boiling point of the solvent.

Alternatively a compound of formula (II), wherein Q, Z, $R^2$, $R^{11}$, $R^{12}$ are as defined above and $R^1$ is hydrogen, X $CH_2$ and Y NH, can be prepared treating a compound of formula (XXVI)

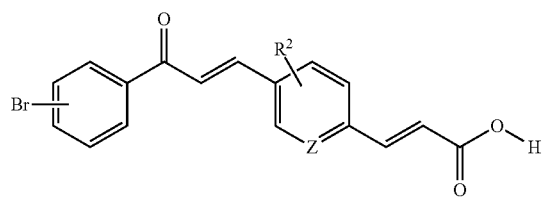

(XXVI)

wherein $R^2$ and Z are as defined above, with a compound of formula (XX)

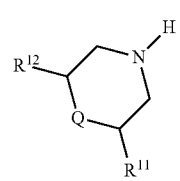

(XX)

wherein $R^{11}$, $R^{12}$ and Q are as defined above, in presence of a catalyst, for example $Pd_2(dba)_3$, in an appropriate solvent, for example toluene, at a temperature ranging from room temperature to the boiling point of the solvent.

Alternatively, a compound of formula (XXVII), which forms a compound of formula (I) by deprotecting the THP moiety following to the procedure described before,

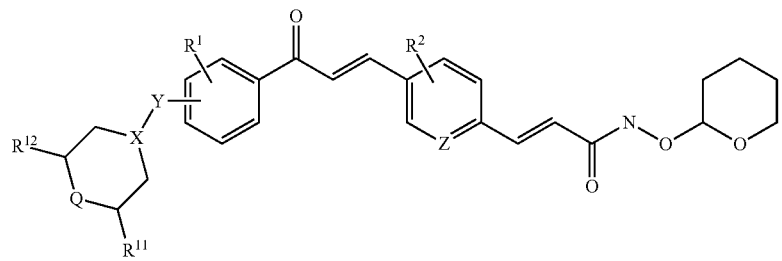

(XXVII)

wherein Q, Z, $R^1$, $R^2$, $R^{11}$ and $R^{12}$ are as defined above, and when Y=$CH_2$ and when X=N, can be obtained by treating a compound of formula (XXVIII)

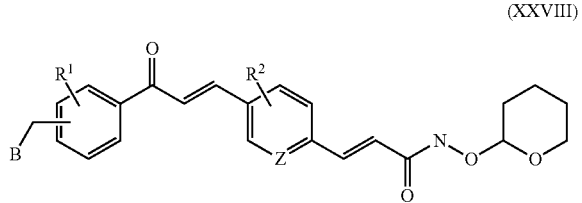

(XXVIII)

wherein Z, $R^1$, $R^2$ and B are as defined above, with a compound of formula (XX), following the experimental procedures described for the reaction between compounds of formula (XXI) and (XX).

$HNR^3R^4$ and the compounds of formula (VI), (VII), (VIII), (IX), (X), (XVI), (XVIII), (XIX), (XX), (XXI), (XXIII), (XXIV), (XXV), (XXVI), and (XXVIII) are known products or can be obtained with known methods by starting from known compounds.

Should the protection of a chemical group of a compound of the present invention and/or an intermediate thereof become necessary, before carrying out one of the afore-described reactions, said chemical group can be protected and deprotected according to known methods. References to protection/deprotection steps can be found for example in the book by Greene and Wuts (Greene, T. W.; Wuts, P. G. M. "Protective Groups in Organic Synthesis", John Wiley & Sons Inc., 1991) or the book by Kocienski (Kocienski, P. J. "Protecting Groups", George Thieme Verlag, 1994).

Salification of the compounds of formula (I), (Ia), (Ib), (Ic), and the preparation of compounds of formula (I), (Ia), (Ib), (Ic), free of their salts can be carried out by known conventional methods.

The compounds of formula (I), (Ia), (Ib), (Ic), have an inhibitory action on histone deacetylases and are therefore useful in the treatment of diseases linked to the disregulation of histone deacetylase activity.

The invention therefore provides compounds of formula (I), (Ia), (Ib), (Ic), as previously defined, for use in therapy, particularly for treating diseases linked to the disregulation of histone deacetylase activity.

The invention also comprises the use of one or more compounds of formula (I), (Ia), (Ib), (Ic), as previously defined, in the preparation of a drug for preventing and/or treating diseases linked to the disregulation of histone deacetylase activity.

The invention also comprises a method for preventing and/or treating diseases linked to the disregulation of histone deacetylase activity characterized by administering, to a patient requiring it, a pharmacologically useful quantity of one or more compounds of formula (I), (Ia), (Ib), (Ic), as previously defined.

The aforesaid uses and methods also include the possibility of co-administration, simultaneously with or delayed with respect to the administration of the compound of formula (I), (Ia), (Ib), (Ic), of additional therapeutic agents.

Diseases linked to the disregulation of histone deacetylase activity at which the present treatment is aimed are particularly tumor type diseases: e.g. leukemias and myeloid and lymphoid lymphomas, myelodysplastic syndromes, multiple myeloma, mammary tumors, pulmonary tumors and pleural mesotheliomas, skin tumors including basal cell carcinomas (basaliomas), melanomas, osteosarcomas, fibrosarcomas, rhabdomyosarcomas, neuroblastomas, glioblastomas, cerebral tumors, testicular and ovarian tumors, endometrial and prostate tumors, thyroid carcinomas, colorectal tumors, gastric tumors and gastrointestinal adenocarcinomas, hepatic carcinomas, pancreatic carcinomas, renal tumors, teratocarcinomas and embryonic carcinomas.

Non-tumor type diseases linked to the disregulation of histone deacetylase activity are for example Huntington's disease, diseases caused by triplet expansion, degenerative diseases, ischemia, oxidative stress, inflammatory responses of the nervous system, epilepsy, diseases caused by protein aggregates, HIV infections, malaria, leishmaniasis, infections by protozoa, fungi, phytotoxic agents, viruses and parasites, autoimmune diseases, chronic immune reactions against the host, hypertrophy and cardiac decompensation, fibrotic diseases of the skin, fibrosis, spinal and bulbar muscular atrophy, bipolar disorders, psychiatric disorders, fragile X syndrome, arthritis, renal diseases, psoriasis, intestinal and colitic diseases, beta thalassemia, respiratory diseases, Rubinstein-Taybi syndrome.

In the aforesaid uses and methods, the dosage of the compounds of formula (I), (Ia), (Ib), (Ic), can vary on the basis of patient type and condition, the degree of disease severity, administration route selected and the number of daily administrations given etc. As an indication, they can be administered within a dose range of between 0.001 and 1000 mg/kg/day.

The invention also comprises pharmaceutical compositions characterized by containing one or more active principles of formula (I), (Ia), (Ib), (Ic), in association with pharmaceutically acceptable excipients and diluents.

The compounds of formula (I), (Ia), (Ib), (Ic) can also be used in combination with additional anti-tumor agents and differentiating agents, for non-exclusive example retinoic acid, either by separate administrations, or by including the two active principles in the same pharmaceutical formulation.

The compounds of formula (I), (Ia), (Ib), (Ic) can be pharmaceutically formulated according to known methods. The pharmaceutical compositions can be chosen on the basis of the treatment requirements. Such compositions are prepared by blending and are suitably adapted to oral or parenteral administration, and as such can be administered in the form of tablets, capsules, oral preparations, powders, granules, pills, injectable or infusible liquid solutions, suspensions or suppositories.

Tablets and capsules for oral administration are normally presented in unit dose form and contain conventional excipients such as binders, fillers, diluents, tableting agents, lubricants, detergents, disintegrants, coloring agents, flavoring agents and wetting agents. The tablets can be coated with methods well known in the art.

Suitable fillers include cellulose, mannitol, lactose and other similar agents. Suitable disintegrants include, polyvinylpyrrolidone and starch derivatives such as sodium glycolate starch. Suitable lubricants include, for example, magnesium stearate. Suitable wetting agents include sodium lauryl sulfate.

These oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents.

Oral formulations also include conventional slow-release formulations such as enterically coated tablets or granules.

For parenteral administration, fluid unit dosages can be prepared, containing the compound and a sterile vehicle. The compound can be either suspended or dissolved, depending on the vehicle and concentration. The parenteral solutions are normally prepared by dissolving the compound in a vehicle and filter sterilizing before filling suitable vials or ampoules and sealing them. Advantageously, adjuvants such as local anaesthetics, preservatives and buffering agents can also be dissolved in the vehicle. To increase stability, the composition can be frozen after having filled the vials and removed the water in vacuo. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. A reference for the formulations is the book by Remington ("Remington: The Science and Practice of Pharmacy", Lippincott Williams & Willcins, 2000). Creams, as known to formulation experts, are viscous liquids or semisolid emulsions, and contain an oil phase, an emulsifier and an aqueous phase. The oil phase generally contains petrolatum and an alcohol such as cetyl or stearic alcohol. The emulsifier in a cream formulation is chosen from non-ionic, anionic, cationic or amphoteric surface-active agents. The monophasic gels contain the organic molecules uniformly distributed in the liquid, which is generally aqueous, but they also preferably contain an alcohol and optionally an oil. Preferred gelling agents are cross-linked acrylic acid polymers (e.g. carbomer-type polymers, such as carboxypolyalkylenes, which are commercially available under the Carbopol™ trademark). Hydrophilic polymers are also preferred, such as polyoxyethylene, polyoxyethylene-polyoxypropylene copolymers and polyvinyl alcohol; cellulose polymers such as hydroxypropyl cellulose, hydroxyethyl cellulose, hydroxypropyl methylcellulose, hydroxypropyl methylcellulose phthalate and methylcellulose; gums, such as xanthan gum and tragacanth gum; sodium alginate; and gelatin. Dispersing agents such as alcohol or glycerin can be added for gel preparation. The gelling agent can be dispersed by finely chopping and/or mixing.

A further method of administering the compounds of the invention regards transdermal delivery. Typical transdermal formulations comprise conventional aqueous and non-aqueous vectors, such as creams, oils, lotions or pastes or can be in the form of membranes or medicated patches. One formulation provides that a compound of the invention is dispersed within a pressure sensitive patch which adheres to the skin. This formulation enables the compound to diffuse from the patch to the patient through the skin. For a constant release of the drug through the skin, natural rubber and silicon can be used as pressure sensitive adhesives.

As is common practice, the compositions are normally accompanied by written or printed instructions for use in the treatment in question.

The invention is described hereinafter by means of the following non-limiting examples.

EXPERIMENTAL PART

1. Chemical Synthesis
Methods

Unless otherwise indicated, all the starting reagents were found to be commercially available and were used with no further purification. Specifically, the following abbreviations may have been used in the descriptions of the experimental methods.

| | |
|---|---|
| g (grams) | NMR (Nuclear Magnetic Resonance) |
| mg (milligrams) | $^1$H (proton) |
| ml (millilitres) | MHz (Megahertz) |
| M (molarity) | Hz (Hertz) |
| μl (microlitres) | LC-MS (Liquid Chromatography Mass Spectrum) |
| mmol (millimoles) | rt (retention time in minutes) |
| THF (tetrahydrofuran) | TEA (triethylamine) |
| EtOAc (ethyl acetate) | NH$_2$OTHP (O-(tetrahydro-2H-pyran-2-yl)hydroxylamine) |
| MeOH (methanol) | HOBT (1-hydroxybenzotriazole) |
| EtOH (ethanol) | AcOH (acetic acid) |
| DCM (dichloromethane) | Pd(OAc)$_2$ (palladium acetate) |
| DMF (dimethylformamide) | DMSO-d$_6$ (deuterated dimethyl sulfoxide) |
| EDC (1-3(dimethylaminopropyl)-3-ethylcarbodiimide hydrochloride) | BOC (tert-butoxycarbonyl) |
| Et$_2$O (diethyl ether) | n-BuLi (n-butyllithium) |

Except where indicated otherwise, all temperatures are expressed in ° C. (degrees centigrade).

The $^1$H-NMR spectra were acquired with a Brucker 300 MHz. The chemical shifts are expressed in parts per million (ppm, δ units). The coupling constants are expressed in Hertz (Hz) and the splitting patterns are described as s (singlet), d (doublet), t (triplet), q (quartet), quint (quintet), m (multiplet), bs (broad singlet).

The LC-MS analyses were carried out according to the following methods:

METHOD A: Waters Acquity UPLC, Micromass ZQ single quadruple (Waters).
Atlantis dC18 Column (100×2.1 mm×3 μm);
flow: 0.3 ml/min splitting ratio MS:waste/1:4;
mobile phase: phase A=H$_2$O/CH$_3$CN (95/5, v/v)+0.1% TFA; phase B=H$_2$O/CH$_3$CN (5/95, v/v)+0.1% TFA. 0-0.5 min (A: 95%, B: 5%), 0.5-7 min (A: 0%, B: 100%), 7-8 min (A: 0%, B: 100%), 8-8.10 min (A: 95%, B: 5%), 8.10-9.50 min (A: 95%, B: 5%); UV wavelength 254 nm or BPI; injection volume: 5 μl METHOD B: Waters Acquity UPLC, Micromass ZQ single quadruple (Waters).
Acquity UPLC-BEH C18 Column (50×2.1 mm×1.7 μm);
flow: 0.4 ml/min splitting ratio MS:waste/1:4;
mobile phase: phase A=H$_2$O/CH$_3$CN (95/5, v/v)+0.1% TFA; phase B=H$_2$O/CH$_3$CN (5/95, v/v)+0.1% TFA. 0-0.25 min (A: 98%, B: 2%), 0.25-4.0 min (A: 0%, B: 100%), 4.0-5.0 min (A: 0%, B: 100%), 5-5.10 min (A: 98%, B: 2%), 5.10-6 min (A: 98%, B: 2%); UV wavelength 254 nm or BPI; injection volume: 5 μl METHOD C: Waters Acquity UPLC, Micromass ZQ Single quadrupole (Waters).
Column Acquity UPLC-BEH C18 (50×2.1 mm, 1.7 μm);
Flow rate: 0.6 ml/min splitting ratio MS:waste/1:4;
Mobile phase: A phase=water/CH$_3$CN 95/5+0.1% TFA; B phase=water/CH$_3$CN 5/95+0.1% TFA. 0-0.25 min (A: 98%, B: 2%), 0.25-3.30 min (A: 0%, B: 100%), 3.30-4.00 min (A: 0%, B: 100%), 4.00-4.10 min (A: 98%, B: 2%); 4.10-5.00 min (A: 98%, B: 2%) UV detection wavelength 254 nm or BPI; Injection volume: 5 μl METHOD D: Waters Acquity UPLC, Micromass ZQ Single quadrupole (Waters).

Column Ascentis (100×2.1 mm, 3 μm);

Flow rate: 0.3 ml/min splitting ratio MS:waste/1:4;

Mobile phase: A phase=water/CH$_3$CN 95/5+0.1% TFA; B phase=water/CH$_3$CN 5/95+0.1% TFA. 0-0.5 min (A: 95%, B: 5%), 0.5-7 min (A: 0%, B: 100%), 7.00-8.00 min (A: 0%, B: 100%), 8.00-8.10 min (A: 95%, B: 5%); 8.10-9.50 min (A: 95%, B: 5%) UV detection wavelength 254 nm or BPI; Injection volume: 5 μl METHOD E: Waters Acquity UPLC, Micromass ZQ Single quadrupole (Waters).

Column Acquity UPLC-BEH C18 (50×2.1 mm, 1.7 μm);

Flow rate: 0.6 ml/min splitting ratio MS:waste/1:4;

Mobile phase: A phase=water/CH$_3$CN 95/5+0.1% TFA; B phase=water/CH$_3$CN 5/95+0.1% TFA. 0-0.5 min (A: 98%, B: 2%), 0.5-6 min (A: 0%, B: 100%), 6.00-7.00 min (A: 0%, B: 100%), 7.00-7.10 min (A: 98%, B: 2%); 7.10-8.50 min (A: 98%, B: 2%) UV detection wavelength 254 nm or BPI; Injection volume: 5 μl METHOD F: Waters Acquity UPLC, Micromass ZQ Single quadrupole (Waters).

Column Acquity UPLC-BEH C18 (50×2.1 mm, 1.7 μm);

Flow rate: 0.6 ml/min splitting ratio MS:waste/1:4;

Mobile phase: A phase=water/CH$_3$CN 95/5+0.1% TFA; B phase=water/CH$_3$CN 5/95+0.1% TFA. 0-0.25 min (A: 95%, B: 5%), 0.25-3.30 min (A: 0%, B: 100%), 3.30-4.00 min (A: 0%, B: 100%), 4.00-4.10 min (A: 95%, B: 5%); 4.10-5.00 min (A: 95%, B: 5%) UV detection wavelength 254 nm or BPI; Injection volume: 5 μl All the mass spectra were acquired with the ESI mode.

Most of the reactions were monitored by thin layer chromatography (TLC) with 0.2 mm Merck silica gel plates (60F-254), visualized with UV light (254 nm). The chromatographic columns were packed with Merck silica gel 60 (0.04-0.063 mm).

Example 1

(E)-N-Hydroxy-3-(4-{(E)-3-[2-(4-methyl-piperazin-1-yl)-phenyl]-3-oxo-propenyl}-phenyl)-acrylamide

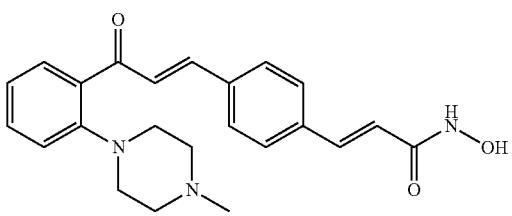

Step A

A mixture of 2-fluoro benzonitrile (2.28 g, 18.84 mmol), 1-methyl piperazine (3.14 ml, 28.26 mmol) and finely ground K$_2$CO$_3$ (3.19 g, 23 mmol) in DMSO (50 ml) was heated to 120° C. for 24 hours.

The mixture was then diluted with H$_2$O and extracted twice with AcOEt. The pooled organic phases were dried over Na$_2$SO$_4$ and evaporated in vacuo.

The crude product was purified by flash chromatography (DCM:MeOH:NH$_3$ 97:3:0.3), the product obtained was dissolved in DCM and treated with HCl in Et$_2$O.

The resulting precipitate was filtered off and washed with DCM to obtain 3.15 g of 2-(4-methyl-piperazin-1-yl)-benzonitrile hydrochloride.

Y=70%

Step B

A solution of 2-(4-methyl-piperazin-1-yl)-benzonitrile hydrochloride (2.16 g, 9.1 mmol) in H$_2$O was brought to basic conditions with NH$_4$OH and extracted with DCM. The organic phase was dried over Na$_2$SO$_4$, and evaporated in vacuo. The product obtained (1.77 g, 8.80 mmol) was dissolved in 30 ml of toluene and added under nitrogen atmosphere to a solution of 3 M methyl magnesium bromide in diethyl ether (8.79 ml, 26.38 mmol). The resulting suspension was heated under reflux for 4 hours. The reaction was cooled down to 0° C., acidified with 10% HCl, and then heated under reflux for 1 hour. The two phases were separated and the aqueous phase was extracted with AcOEt, then brought to basic conditions with NH$_4$OH and extracted with DCM. The organic phase was dried over Na$_2$SO$_4$ and concentrated in vacuo to dryness. The crude product was purified by flash chromatography (DCM:MeOH:NH$_3$ 98:2:0.2) to obtain 1.62 g of 1-[2-(4-methyl-piperazin-1-yl)-phenyl]-ethanone.

Y=84%

Step C

A mixture of 1-[2-(4-methyl-piperazin-1-yl)-phenyl]-ethanone (542 mg, 2.48 mmol), 4-formyl cinnamic acid (438 mg, 2.48 mmol) and 1.7 M KOH (2.92 ml) in H$_2$O (5 ml) and EtOH (5 ml) was stirred at room temperature for 24 hours.

The mixture was then acidified with 10% HCl and the resulting yellow precipitate was filtered off through a Buchner funnel to obtain 0.93 g of (E)-3-(4-{(E)-3-[2-(4-methyl-piperazin-1-yl)-phenyl]-3-oxo-propenyl}-phenyl)-acrylic acid hydrochloride.

Y=90%

Step D

A mixture of (E)-3-(4-{(E)-3-[2-(4-methyl-piperazin-1-yl)-phenyl]-3-oxo-propenyl}-phenyl)-acrylic acid hydrochloride (250 mg, 0.608 mmol), NH$_2$OTHP (85.4 mg, 0.73 mmol), EDC (232 mg, 1.22 mol), HOBT (164 mg, 1.22 mmol) and TEA (253 μl, 1.82 mmol) in THF (5 ml) and DMF (5 ml) was stirred for 24 hours at room temperature. The mixture was then diluted with water and extracted with AcOEt. The organic phase was washed with water, then with a saturated NaCl solution, dried over Na$_2$SO$_4$ and evaporated in vacuo to dryness.

The crude product was purified by flash chromatography (DCM:MeOH:NH$_3$ 98:2:0.2). The product obtained was dissolved in DCM and treated with HCl in Et$_2$O for 1 hour to obtain precipitation of a yellow solid. The solid was then filtered off through a Buchner funnel to obtain 115 mg of (E)-N-hydroxy-3-(4-{(E)-3-[2-(4-methyl-piperazin-1-yl)-phenyl]-3-oxo-propenyl}-phenyl)-acrylamide hydrochloride.

Y=44%

LC-MS: METHOD A, rt=3.34; (ES+) MH$^+$: 392.2

$^1$H-NMR (DMSO-d$_6$) δ: 10.90 (bs, 1H); 7.83 (d, 2H); 7.64 (d, 2H); 7.64-7.52 (m, 5H); 7.27 (d, 1H); 7.20 (dd, 1H); 6.56 (d, 1H); 3.50-3.13 (m, 6H); 2.89 (bs, 2H); 2.66 (d, 3H).

The compounds in table 1 were obtained by following the aforedescribed procedure (steps A-D or C-D when the intermediates were found to be commercially available).

TABLE 1

| Ex no | structure | Compound name | MH+ | 1H-NMR (DMSO-d6) δ: |
|---|---|---|---|---|
| 2 | 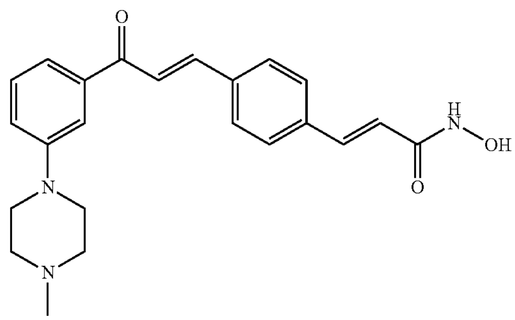 | (E)-N-Hydroxy-3-(4-{(E)-3-[3-(4-methyl-piperazin-1-yl)-phenyl]-3-oxo-propenyl}-phenyl)-acrylamide | 392.3 | 11.08 (bs, 1H); 7.94 (d, 1H); 7.93 (d, 2H); 7.74 (d, 1H); 7.66 (m, 4H); 7.50 (d, 1H); 7.47 (dd, 1H); 7.33 (dd, 1H); 6.60 (d, 1 H); 3.96 (d br, 2H); 3.51 (d br 2H); 3.20 (m, 4H); 2.82 (d, 3H) |
| 3 | 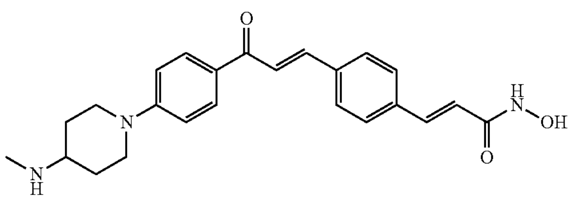 | (E)-N-Hydroxy-3-(4-{(E)-3-[4-(4-methylamino-piperidin-1-yl)-phenyl]-3-oxo-propenyl}-phenyl)-acrylamide | 406.50 | |
| 4 | 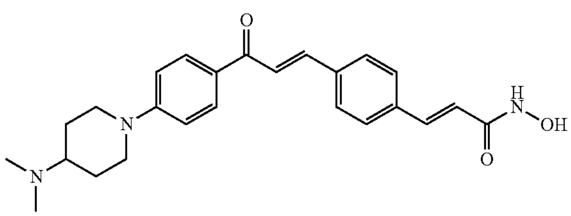 | (E)-3-(4-{(E)-3-[4-(4-Dimethylamino-piperidin-1-yl)-phenyl]-3-oxo-propenyl}-phenyl)-N-hydroxy-acrylamide | 420.3 | 10.89 (bs, 1H); 8.07 (d, 2H); 7.95 (d, 1H); 7.91 (d, 2H); 7.66 (d, 1H); 7.63 (d, 2H); 7.49 (d, 1H); 7.07 (d, 2H); 6.59 (d, 1H); 4.16 (d br, 2H); 3.40 (m, 1H); 2.91 (dd, 2H); 2.72 (d, 6H); 2.14 (d br, 2H); 1.69 (m, 2H) |
| 5 | 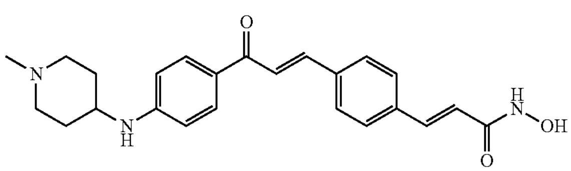 | (E)-N-Hydroxy-3-(4-{(E)-3-[4-(1-methyl-piperidin-4-yl-amino)-phenyl]-3-oxo-propenyl}-phenyl)-acrylamide | 406.50 | |
| 6 | 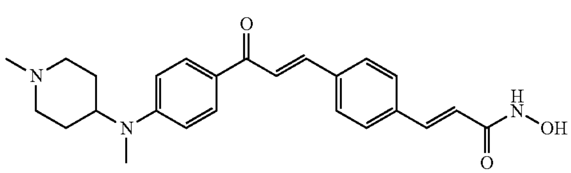 | (E)-N-Hydroxy-3-[4-(E)-3-{4-[N-methyl-(1-methyl-piperidin-4-yl)-amino]-phenyl}-3-oxo-propenyl)-phenyl]-acrylamide | 420.3 | |

The compound of Example 5 can be alternatively prepared by the following procedure:

Step A

A mixture of 1-(4-bromo-phenyl)-ethanone (1 g, 5.02 mmol), tert-butyl 4-formyl cinnamate (1.16 g, 5.02 mmol), KOH (560 mg, 1.04 mmol) in EtOH (20 ml) and H₂O (5 ml), was stirred at room temperature for 4 h. The mixture was then diluted with water and the resulting precipitate was filtered to give 1.7 g of tert-butyl (E)-3-{4-[(E)-3-(4-bromo-phenyl)-3-oxo-propenyl]-phenyl}-acrylate as yellow powder.
Y=81%

Step B

A mixture of (±)BINAP (435 mg, 0.7 mmol) and Pd₂(dba)₃ (320 mg, 0.35 mmol) in toluene (10 ml) was heated to 80° C. for 1 h under N₂. Then the mixture was cooled down to room temperature and tert-butyl (E)-3-{4-[(E)-3-(4-bromo-phenyl)-3-oxo-propenyl]-phenyl}-acrylate (726 mg, 1.75 mmol), 1-methyl-piperidin-4-ylamine (0.200, 1.75 mmol) and NaOtBu (252 mg, 2.6 mmol) were added. The reaction was refluxed overnight under N₂, then the slurry was filtrated (Celite) and the organic filtrate was evaporated in vacuo. The crude reaction mixture was purified by column chromatography (eluent: petroleum ether/AcOEt 1:1). The resulting product was dissolved in DCM (1 ml) and TFA (1 ml) and the solution was stirred at room temperature for 4 h. The solvent was removed in vacuo to give 280 mg of (E)-3-(4-{(E)-3-[4-

(1-methyl-piperidin-4-ylamino)-phenyl]-3-oxo-propenyl}-phenyl)-acrylic acid as its trifluoroacetate salt.
Y=32%

Step C
A mixture of (E)-3-(4-{(E)-3-[4-(1-methyl-piperidin-4-ylamino)-phenyl]-3-oxo-propenyl}-phenyl)-acrylic acid trifluoroacetate (126 mg, 0.25 mmol), HOBT (40 mg, 0.30 mmol), EDC (58 mg, 0.30 mmol), TEA (0.10 ml, 0.75 mmol) and NH₂OTHP (30 mg, 0.25 mmol) in THF (5 ml) and DMF (1 ml), was stirred at room temperature overnight and then partitioned between water and AcOEt. The organic extract was dried over Na₂SO₄ and evaporated in vacuo. The crude product was triturated in CH₃CN/MeOH 9:1 and filtered to give a brown powder that was dissolved in DCM and treated with HCl/Et₂O for 2 h. The precipitate was filtered off to give 65 mg of (E)-N-hydroxy-3-(4-{(E)-3-[4-(1-methyl-piperidin-4-ylamino)-phenyl]-3-oxo-propenyl}-phenyl)-acrylamide as its hydrochloride salt.
Y=60%
LC-MS: Method C, rt=1.29; (ES+) MH+: 406.24
1H NMR (DMSO-d₆) δ (ppm): 10.42 (bs, 1H), 10.22 (s, 1H), 7.99 (m, 2H), 7.90 (d, 1H), 7.87 (m, 2H), 7.56-7.70 (m, 3H), 7.48 (d, 1H), 6.70 (m, 2H), 6.56 (d, 1H), 3.56-3.69 (m, 1H), 3.36-3.53 (m, 2H), 2.92-3.33 (m, 2H), 2.74 (d, 3H), 2.00-2.19 (m, 2H), 1.67-1.94 (m, 2H).

Example 7

(E)-N-Hydroxy-3-(4-{(E)-3-[4-(4-methyl-piperazin-1-yl-methyl)-phenyl]-3-oxo-propenyl}-phenyl)-acrylamide

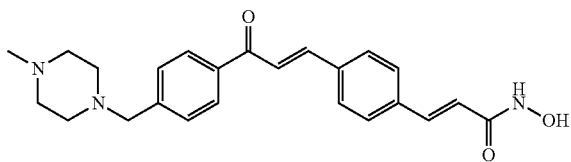

Step A
1-methyl piperazine (805 µl, 7.6 mmol) was added to a solution of 4-(bromomethyl)benzonitrile (1 g, 5.1 mmol) and TEA (1.4 ml, 10.2 mmol) in DCM (15 ml) and the resulting mixture was stirred at room temperature for 24 hours. The solution was then diluted with DCM, washed with a 5% NaHCO₃ solution and then with H₂O. The organic phase was dried over Na₂SO₄ and evaporated to dryness to give 0.73 g of 4-(4-methyl-piperazin-1-yl)-benzonitrile as a white solid.
Y=67%

Step B
0.73 g of 4-(4-methyl-piperazin-1-yl-methyl)-benzonitrile (3.40 mmol) were dissolved in toluene (13 ml) and added to a solution of 3 M methyl magnesium bromide in diethyl ether (3.4 ml, 10.2 mmol) under nitrogen atmosphere. The resulting suspension was heated under reflux for 4 hours. The reaction was cooled down to 0° C., acidified with 10% HCl and then heated under reflux for 1 hour. The two phases were separated and the aqueous phase rinsed with AcOEt, then brought to basic conditions with NH₄OH and extracted with DCM. The organic phase was dried over Na₂SO₄ and concentrated in vacuo to dryness to obtain 0.71 g of 1-[4-(4-methyl-piperazin-1-yl-methyl)-phenyl]-ethanone as a yellow oil.
Y=90%

Step C
A mixture of 1-[4-(4-methyl-piperazin-1-yl-methyl)-phenyl]-ethanone (392 mg, 1.69 mmol), 4-formyl cinnamic acid (300 mg, 1.69 mmol) and 1.7 M KOH (2.0 ml, 3.4 mmol) in H₂O (5 ml) and EtOH (5 ml) was stirred at room temperature for 24 hours.
The mixture was then acidified with 10% HCl and the resulting yellow precipitate was filtered off through a Buchner funnel to obtain 542 mg of (E)-3-(4-{(E)-3-[4-(4-methyl-piperazin-1-yl-methyl)-phenyl]-3-oxo-propenyl}-phenyl)-acrylic acid dihydrochloride.
Y=69%

Step D
A mixture of (E)-3-(4-{(E)-3-[4-(4-methyl-piperazin-1-yl-methyl)-phenyl]-3-oxo-propenyl}-phenyl)-acrylic acid dihydrochloride (542 mg, 1.17 mmol), NH₂OTHP (164 mg, 1.4 mmol), EDC (447 mg, 2.34 mol), HOBT (316 mg, 2.34 mmol) and TEA (488 µl, 3.51 mmol) in THF (5 ml) and DMF (5 ml) was stirred for 24 hours at room temperature. The mixture was then diluted with water and extracted with AcOEt. The organic phase was washed with water, then with a saturated NaCl solution, dried over Na₂SO₄ and evaporated in vacuo to dryness.
The crude product was purified by flash chromatography (DCM:MeOH:NH₃ 98:2:0.2). The product obtained was dissolved in DCM and treated with HCl in Et₂O for 1 hour to obtain precipitation of a yellow solid. The solid was then filtered off through a Buchner funnel to obtain 300 mg of (E)-N-hydroxy-3-(4-{(E)-3-[4-(4-methyl-piperazin-1-yl-methyl)-phenyl]-3-oxo-propenyl}-phenyl)-acrylamide dihydrochloride.
Y=53%
LC-MS: METHOD A, rt=3.02; (ES+) MH⁺: 406.2
¹H-NMR (DMSO-d₆) δ: 11.74 (bs, 1H); 10.12 (bs, 1H); 8.23 (d, 2H); 7.99 (d, 1H); 7.94 (d, 2H); 7.86 (d, 2H); 7.77 (d, 1H); 7.65 (d, 2H); 7.49 (d, 1H); 6.59 (d, 1H); 4.45 (d, 2H); 3.70-3.17 (m, 8H); 2.81 (s, 3H).

The compounds in Table 2 were obtained by following the aforedescribed procedure.

TABLE 2

| Ex no | Structure | Compound name | MH⁺ | ¹H-NMR (DMSO-d₆) δ: |
|---|---|---|---|---|
| 8 | 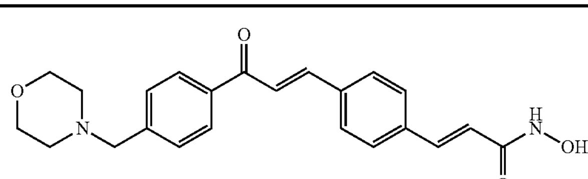 | (E)-N-Hydroxy-3-{4-[(E)-3-(4-morpholin-4-yl-methyl-phenyl)-3-oxo-propenyl]-phenyl}-acrylamide | 393.2 | 11.25 (bs, 1H); 10.83 (bs, 1H); 8.24 (d, 2H); 7.99 (d, 1H); 7.94 (d, 2H); 7.82 (d, 2H); 7.77 (d, 1H); 7.66 (d, 2H); 7.49 (d, 1H); 6.58 (d, 1H); 4.44 (s, 2H); 4.03-3.72 (m, 4H); 3.32-3.00 (m, 4H). |

TABLE 2-continued

| Ex no | Structure | Compound name | MH+ | 1H-NMR (DMSO-d6) δ: |
|---|---|---|---|---|
| 9 | 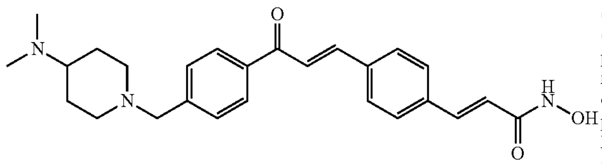 | (E)-3-(4-{(E)-3-[4-(4-Dimethylamino-piperidin-1-yl-methyl)-phenyl]-3-oxo-propenyl}-phenyl)-N-hydroxy-acrylamide | 434.5 | (DMSO-d6 + TFA): 11.15 (bs, 1H); 10.88 (bs, 1H); 8.25 (d, 2H); 8.00 (d, 1H); 7.95 (d, 2H); 7.82 (d, 2H); 7.77 (d, 1H); 7.66 (d, 2H); 7.50 (d, 1H); 6.60 (d, 1H); 4.42 (s, 2H); 3.58-3.26 (m, 2H); 3.01 (m, 2H); 2.87-2.62 (m, 7H); 2.32-202 (m, 4H). |

Example 10

(E)-N-Hydroxy-3-(4-{(E)-3-[4-(1-methyl-piperidin-4-yl)-phenyl]-3-oxo-propenyl}-phenyl)-acrylamide

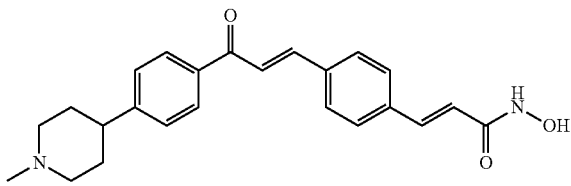

Step A

A mixture of 4-phenyl piperidine hydrochloride (1.23 g, 6.2 mmol), formaldehyde (36.5% in H₂O, 0.702 ml, 9.3 mmol), NaBH(OAc)₃ (2.63 g, 12.42 mmol) and AcOH (0.71 ml, 12.42 mmol) in DCM (30 ml) was stirred for 24 hours at room temperature. The mixture was then brought to basic conditions with a 5% NaHCO₃ solution and extracted twice with DCM. The pooled organic phases were dried over Na₂SO₄ and evaporated to dryness. The residue was dissolved in DCM and treated with HCl in Et₂O observing the precipitation of a white solid. The solid was filtered off through a Buchner funnel to obtain 1 g of 1-methyl-4-phenylpiperidine hydrochloride as a white solid.

Y=77%

Step B

Acetyl chloride (0.634 ml, 8.92 mmol) and AlCl₃ (991 mg, 7.43 mmol) were added to a solution of 1-methyl-4-phenylpiperidine hydrochloride (786 mg, 3.7 mmol) in DCM (16 ml). The resulting mixture was heated to reflux under nitrogen atmosphere for 5 hours during which further 0.53 ml of acetyl chloride and 991 mg of AlCl₃ were added.

The reaction was then cooled down to room temperature and slowly quenched with H₂O. The mixture was brought to basic conditions with a 5% K₂CO₃ solution and extracted with DCM. The organic phase was dried over Na₂SO₄ and evaporated to dryness.

The crude product was purified by flash chromatography (DCM:MeOH:NH₃ 98:2:0.2).

The resulting oil was dissolved in DCM and treated with HCl in Et₂O observing the precipitation of a white solid. The solid was filtered through a Buchner funnel to give 873 mg of 1-[4-(1-methyl-piperidin-4-yl)-phenyl]-ethanone hydrochloride as a white solid.

Y=93%

Step C

A mixture of 1-[4-(1-methyl-piperidin-4-yl)-phenyl]-ethanone hydrochloride (544 mg, 2.15 mmol), 4-formylcinnamic acid tert-butyl ester (500 mg, 2.15 mmol) and 1.7 M KOH (3.8 ml, 6.46 mmol) in EtOH (10 ml) was stirred at room temperature for 6 hours. During the reaction, the formation of a precipitate was observed. The solid was then filtered off through a Buchner funnel to obtain 270 mg of (E)-3-(4-{(E)-3-[4-(1-methyl-piperidin-4-yl)-phenyl]-3-oxo-propenyl}-phenyl)-acrylic acid tert-butyl ester as a yellow solid.

Y=29%

Step D

2 ml of trifluoroacetic acid were added to a solution of (E)-3-(4-{(E)-3-[4-(1-methyl-piperidin-4-yl)-phenyl]-3-oxo-propenyl}-phenyl)-acrylic acid tert-butyl ester (270 mg, 0.63 mmol) in 10 ml of DCM. The solution was stirred at room temperature for 2 hours. The solvent was then removed until dryness and 300 mg of (E)-3-(4-{(E)-3-[4-(1-methyl-piperidin-4-yl)-phenyl]-3-oxo-propenyl}-phenyl)-acrylic acid trifluoro acetate were obtained as a yellow solid.

Y=98%

Step E

A mixture of (E)-3-(4-{(E)-3-[4-(1-methyl-piperidin-4-yl)-phenyl]-3-oxo-propenyl}-phenyl)-acrylic acid trifluoro acetate (310 mg, 0.634 mmol), NH₂OTHP (89 mg, 0.76 mmol), EDC (242 mg, 1.268 mmol), HOBT (172 mg, 1.268 mmol) and TEA (176 μl, 1.268 mmol) in THF (5 ml) and DMF (5 ml), was stirred for 24 hours at room temperature. The mixture was then diluted with water and extracted with AcOEt. The organic phase was then washed with water, with a saturated NaCl solution and then dried over Na₂SO₄ and evaporated in vacuo to dryness.

The crude product was purified by flash chromatography (DCM:MeOH:NH₃ 98:2:0.2). The product obtained was dissolved in DCM and treated with HCl in Et₂O for 1 hour to obtain the precipitation of a yellow solid. The solid was then filtered off through a Bucher funnel and purified by preparative HPLC-MS to obtain mg of (E)-N-Hydroxy-3-(4-{(E)-3-[4-(1-methyl-piperidin-4-yl)-phenyl]-3-oxo-propenyl}-phenyl)-acrylamide trifluoro acetate.

Y=6%

LC-MS: METHOD A, rt=3.31; (ES+) MH+: 391.2

¹H-NMR (DMSO-d₆) δ: 10.78 (bs, 1H); 9.35 (bs, 1H); 9.06 (s, 1H); 8.15 (d, 2H); 7.96 (d, 1H); 7.92 (d, 2H); 7.74 (d, 1H); 7.66 (d, 2H); 7.50 (d, 1H); 7.45 (d, 2H); 6.57 (d, 1H); 3.55 (m, 2H); 3.09 (m, 2H); 2.93 (m, 1H); 2.84 (s, 3H); 2.15-1.76 (m, 4H).

Example 11

(E)-N-Hydroxy-3-(5-{(E)-3-[4-(4-methyl-piperazin-1-yl)-phenyl]-3-oxo-propenyl}-pyridin-2-yl)-acrylamide

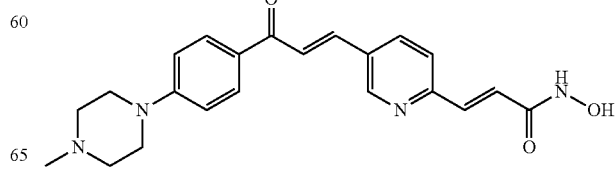

Step A

A solution of 6-bromopyridine-3-carbaldehyde (3.07 g, 16.5 mmol), p-toluenesulfonic acid (386 mg, 2.02 mmol) and trimethyl orthoformate (1.97 ml, 18 mmol) in MeOH (80 ml) was stirred at room temperature for 48 hours. The mixture was then brought to basic conditions with a 5% NaHCO$_3$ solution and extracted twice with diethyl ether. The pooled organic phases were dried over Na$_2$SO$_4$ and evaporated to dryness to give 3.66 g of 2-bromo-5-dimethoxymethyl-pyridine as a pale yellow oil.

Y=95%

Step B

A solution of 2.5 M BuLi in hexane (7.6 ml) was added drop-wise, under a N$_2$ atmosphere, to a solution of 2-bromo-5-dimethoxymethyl-pyridine (3.66 g, 15.84 mmol) in THF (60 ml) at −70° C. After 15 minutes, DMF (1.82 ml, 23.5 mmol) was added drop-wise and the mixture was stirred for 30 minutes at −70° C. and then allowed to reach room temperature. The reaction was diluted with H$_2$O and extracted with DCM. The organic phase was dried over Na$_2$SO$_4$ and evaporated to dryness in vacuo. The crude product was purified by flash chromatography (petroleum ether:AcOEt 7:3) to obtain 1.54 g of 5-dimethoxymethyl-pyridine-2-carbaldehyde as a yellow oil.

Y=54%

Step C

A solution of 5-dimethoxymethyl-pyridine-2-carbaldehyde (1.54 g, 8.50 mmol) in 20 ml of THF was added drop-wise under nitrogen to a mixture of tert-butyl diethyl phosphonoacetate (2.36 g, 9.36 mmol) and NaH (60%, 442 mg, 11.06 mmol) in THF (20 ml). The resulting solution was stirred at room temperature for 1 hour, then slowly diluted with H$_2$O and extracted twice with diethyl ether. The pooled organic phases were dried over Na$_2$SO$_4$ and evaporated to dryness. The crude product was purified by flash chromatography (petroleum ether: AcOEt 92:8) to obtain 1.76 g of (E)-3-(5-dimethoxymethyl-pyridin-2-yl)-acrylic acid tert-butyl ester as a pale yellow oil.

Y=74%

Step D

A mixture of (E)-3-(5-dimethoxymethyl-pyridin-2-yl)-acrylic acid tert-butyl ester (1.76 mg, 6.30 mmol) in THF (30 ml) and 1 M HCl (25 ml) was stirred for 4 hours at room temperature, then brought to basic conditions with a 5% NaHCO$_3$ solution and extracted twice with Et$_2$O. The pooled organic phases were dried over Na$_2$SO$_4$ and evaporated in vacuo to dryness to give 1.45 g of (E)-3-(5-formyl-pyridin-2-yl)-acrylic acid tert-butyl ester as a white solid.

Y=98%

Step E

A mixture of (E)-3-(5-formyl-pyridin-2-yl)-acrylic acid tert-butyl ester (261 mg, 1.12 mmol), 1-[4-(4-methyl-piperazin-1-yl)-phenyl]-ethanone (246 mg, 1.2 mmol) and KOH (125 mg, 2.24 mmol) in 10 ml of EtOH was stirred at room temperature for 24 hours, observing the formation of a precipitate. The solid was then filtered off through a Buchner funnel to obtain 222 mg of (E)-3-(5-{(E)-3-[4-(4-methyl-piperazin-1-yl)-phenyl]-3-oxo-propenyl}-pyridin-2-yl)-acrylic acid tert-butyl ester.

Y=45%

Step F

A mixture of (E)-3-(5-{(E)-3-[4-(4-methyl-piperazin-1-yl)-phenyl]-3-oxo-propenyl}-pyridin-2-yl)-acrylic acid tert-butyl ester (222 mg, 0.513 mmol) and trifluoro acetic acid (2 ml) in DCM (5 ml) was stirred at room temperature for 5 hours.

The solvent was evaporated in vacuo to dryness to give 330 mg of (E)-3-(5-{(E)-3-[4-(4-methyl-piperazin-1-yl)-phenyl]-3-oxo-propenyl}-pyridin-2-yl)-acrylic acid bis trifluoroacetate.

Y=>99%

Step G

A mixture of (E)-3-(5-{(E)-3-[4-(4-methyl-piperazin-1-yl)-phenyl]-3-oxo-propenyl}-pyridin-2-yl)-acrylic acid bis trifluoroacetate (330 mg, 0.54 mmol), NH$_2$OTHP (78 mg, 0.67 mmol), EDC (155 mg, 0.81 mmol), HOBT (109 mg, 0.80 mmol) and TEA (280 µl, 2 mmol) in THF (5 ml) and DMF (5 ml), was stirred for 72 hours at room temperature. The mixture was then diluted with water and extracted with AcOEt. The organic phase was washed with water, then with a saturated NaCl solution, dried over Na$_2$SO$_4$ and evaporated in vacuo to dryness.

The crude product was purified by flash chromatography (DCM:MeOH:NH$_3$ 96:4:0.2). The product obtained was dissolved in DCM and treated with HCl in Et$_2$O for 1 hour to obtain precipitation of a dark brown solid. The solid was then filtered off through a Buchner funnel, washed with DCM to obtain 156 mg of (E)-N-hydroxy-3-(5-{(E)-3-[4-(4-methyl-piperazin-1-yl)-phenyl]-3-oxo-propenyl}-pyridin-2-yl)-acrylamide dihydrochloride.

Y=62%

LC-MS: METHOD B, rt=1.36; (ES+) MH$^+$: 393.3

$^1$H-NMR (DMSO-d$_6$) δ: 11.38 (bs, 1H); 9.09 (d, 1H); 8.52 (dd, 1H); 8.19-8.09 (m, 3H); 7.81 (d, 1H); 7.72 (d, 1H); 7.56 (d, 1H); 7.12 (d, 2H); 7.07 (d, 1H); 4.13 (m, 2H); 3.49 (m, 2H); 3.35 (m, 2H); 3.13 (m, 2H); 2.80 (d, 3H).

Example 12

(E)-N-Hydroxy-3-(4-{(E)-3-[4-(4-isobutyl-piperazin-1-yl)-phenyl]-3-oxo-propenyl}-phenyl)-acrylamide

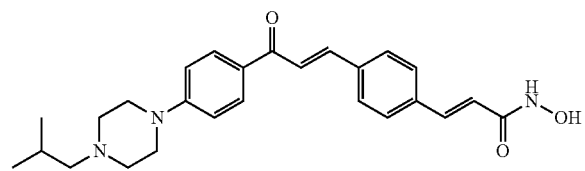

Step A

Isobutylaldehyde (0.230 ml, 2.94 mmol) and Na(CH$_3$CO$_2$)$_3$BH (620 mg, 2.94 mmol) were added at 5° C. to a solution of 4-piperazino-acetophenone (500 mg, 2.45 mmol) in 1,2-dichloroethane (10 ml). The resulting mixture was stirred for 4 hours at room temperature.

The mixture was then concentrated in vacuo, brought to basic conditions with a 5% NaHCO$_3$ solution and extracted with AcOEt. The organic phase was dried over Na$_2$SO$_4$ and evaporated in vacuo to dryness.

The crude product was ground in isopropyl ether, filtered off and then oven dried to obtain 1-[4-(4-isobutyl-piperazin-1-yl)-phenyl]-ethanone.

Y=80%

Step B

A mixture of 1-[4-(4-isobutyl-piperazin-1-yl)-phenyl]-ethanone (520 mg, 2 mmol), 4-formylcinnamic acid (360 mg, 2 mmol) and 1.7 M KOH (2.5 ml) in EtOH (10 ml) was stirred at room temperature for 12 hours.

The product was filtered off and oven dried to give 450 mg of (E)-3-(4-{(E)-3-[4-(4-isobutyl-piperazin-1-yl)-phenyl]-3-oxo-propenyl}-phenyl)-acrylic acid as potassium salt.

Y=50%

Step C

A mixture of (E)-3-(4-{(E)-3-[4-(4-isobutyl-piperazin-1-yl)-phenyl]-3-oxo-propenyl}-phenyl)-acrylic acid as potassium salt (450 mg, 1 mmol), NH$_2$OTHP (117 mg, 1 mmol), EDC (230 mg, 1.2 mmol), HOBT (160 mg, 1.2 mmol) and TEA (0.420 ml, 3 mmol) in THF (5 ml) and DMF (5 ml) was stirred for 24 hours at room temperature. The mixture was then diluted with water and extracted with AcOEt. The organic phase was washed with water, then with a saturated NaCl solution, dried over Na$_2$SO$_4$ and evaporated in vacuo to dryness. The crude product was purified by flash chromatography (DCM:MeOH:NH$_3$ 98:2:0.2). The product was then dissolved in DCM and a few drops of HCl in ether were added. The mixture was stirred for 12 hours at room temperature. The precipitate was then filtered and ground in acetonitrile to obtain 300 mg of (E)-N-hydroxy-3-(4-{(E)-3-[4-(4-isobutyl-piperazin-1-yl)-phenyl]-3-oxo-propenyl}-phenyl)-acrylamide hydrochloride.

Y=64%

LC-MS: METHOD B, rt=2.24; (ES+) MH$^+$: 434.5

$^1$H-NMR (DMSO-d$_6$) δ: 10.83 (bs, 1H); 10.49 (bs, 1H); 8.12 (d, 2H); 7.97 (d, 1H); 7.91 (d, 2H); 7.68 (d, 1H); 7.64 (d, 2H); 7.48 (d, 1H); 7.11 (d, 2H); 6.59 (d, 1H); 4.08 (m, 2H); 3.62-3.44 (m, 4H); 3.12 (m, 2H); 3.01 (m, 2H); 2.15 (m, 1H); 1.02 (d, 6H).

The compounds in Table 3 were obtained by following the aforedescribed process.

Step A

A solution of 4-piperazino-acetophenone (2 g, 9.8 mmol), 4-formyl cinnamic acid (1.72, 9.8 mmol) and 1.7 M KOH (10 ml) in EtOH (20 ml) and H$_2$O (5 ml) was stirred for 12 hours at room temperature.

10% HCl (30 ml) was then added to the mixture and the precipitate was filtered off and dried in vacuo to obtain 3.8 g of (E)-3-{4-[(E)-3-oxo-3-(4-piperazin-1-yl-phenyl)-propenyl]-phenyl}-acrylic acid as hydrochloride. Y=97%

Step B

A mixture of (E)-3-{-4-[(E)-3-(4-piperazin-1-yl-phenyl)-3-oxo-propenyl]-phenyl}-acrylic acid hydrochloride (550 mg, 1.38 mmol), BOC anhydride (361 mg, 1.65 mmol) and triethylamine (0.390 ml, 2.8 mmol) in 1,4-dioxane (5 ml) and H$_2$O (5 ml) was stirred for 12 hours at room temperature.

The solvent was evaporated in vacuo and the residue was ground in di-isopropylether. The solid was then filtered off and oven dried to obtain 638 mg of 4-(4-{(E)-3-[4-((E)-2-carboxy-vinyl)-phenyl]-acryloyl}-phenyl)-piperazino-1-carboxylic acid tert-butyl ester.

Y=quantitative.

Step C

A mixture of 4-(4-{(E)-3-[4-((E)-2-carboxy-vinyl)-phenyl]-acryloyl}-phenyl)-piperazino-1-carboxylic acid tert-butyl ester (460 mg, 1 mmol), NH$_2$OTHP (117 mg, 1 mmol), EDC (230 mg, 1.2 mmol), HOBT (160 mg, 1.2 mmol) and TEA (0.420 ml, 3 mmol) in THF (5 ml) and DMF (5 ml) was stirred for 24 hours at room temperature. The mixture was then diluted with water and extracted with AcOEt. The organic phase was washed with water, then with a saturated NaCl solution, dried over Na$_2$SO$_4$ and evaporated in vacuo to dryness.

TABLE 3

| Ex no | structure | Compound name | MH$^+$ | $^1$H-NMR (DMSO-d$_6$) δ: |
|---|---|---|---|---|
| 13 | 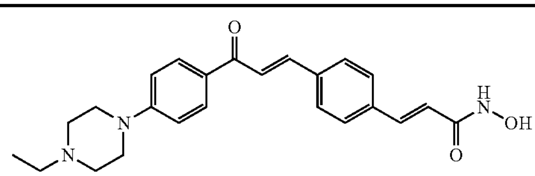 | (E)-3-(4-{(E)-3-[4-(4-Ethyl-piperazin-1-yl)-phenyl]-3-oxo-propenyl}-phenyl)-N-hydroxy-acrylamide | 406.50 | (DMSO-d$_6$ + TFA): 8.08 (d, 2H); 7.84 (d, 2H); 7.83 (d, 1H); 7.66 (d, 1H); 7.62 (d, 2H); 7.50 (d, 1H); 7.01 (d, 2H); 6.62 (d br, 1H); 4.12-3.24 (m br, 8H); 3.21 (q, 2H); 1.33 (t, 3H). |
| 14 | 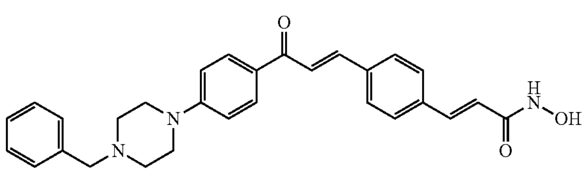 | (E)-3-(4-{(E)-3-[4-(4-Benzyl-piperazin-1-yl)-phenyl]-3-oxo-propenyl}-phenyl)-N-hydroxy-acrylamide | 468.1 | 10.79 (s, 1H); 10.52 (bs, 1H); 9.05 (bs, 1H); 8.11 (d, 2H); 7.96 (d, 1H); 7.90 (d, 2H); 7.74-7.37 (m, 9H); 7.08 (d, 2H); 6.55 (d, 1H); 4.41 (s, 2H); 4.14 (m, 2H); 3.41-3.07 (m, 6H). |

Example 15

(E)-N-Hydroxy-3-{4-[(E)-3-(4-piperazin-1-yl-phenyl)-3-oxo-propenyl]-phenyl}-acrylamide

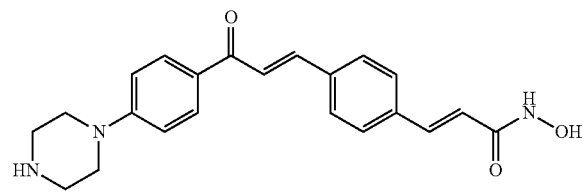

The crude product was then dissolved in DCM and a few drops of HCl in ether were added to the solution. The mixture was stirred for 12 hours at room temperature and the resulting precipitate was then filtered off to obtain 180 mg of (E)-N-hydroxy-3-{4-[(E)-3-oxo-3-(4-piperazin-1-yl-phenyl)-propenyl]-phenyl}-acrylamide hydrochloride.

Y=43%

LC-MS: METHOD A, rt=3.22; (ES+) MH$^+$: 378.1

$^1$H-NMR (DMSO-d$_6$) δ: 10.79 (bs, 1H); 9.23 (s, 2H); 8.11 (d, 2H); 7.97 (d, 1 H); 7.91 (d, 2H); 7.68 (d, 1H); 7.64 (d, 2H); 7.49 (d, 1H); 7.10 (d, 2H); 6.57 (d, 1H); 3.63 (m, 4H); 3.23 (m, 4H).

Preparation 1

1-[4-(1-Methyl-piperidin-4-yloxy)-phenyl]-ethanone

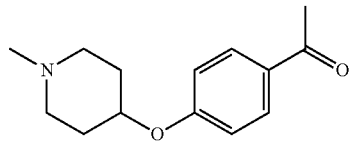

Diethyl azodicarboxylate (1.27 g, 7.35 mmol) was added to a stirred mixture of 1-(4-hydroxy-phenyl)-ethanone (1 g, 7.35 mmol), 1-methyl-piperidin-4-ol (845 mg, 7.35 mmol) and PPh$_3$ (1.92 g, 7.35 mmol) in THF (50 ml) at 0° C. The resulting brown solution was stirred at 0° C. for 1 h and then at room temperature for 4 h. The mixture was partitioned between water and AcOEt and the organic phase was extracted with 1 M HCl. The aqueous phase was brought to basic conditions with NH$_4$OH and extracted with AcOEt.

The organic phase was dried over Na$_2$SO$_4$ and evaporated in vacuo. The crude mixture was purified by silica gel chromatography to give 351 mg of 1-[4-(1-methyl-piperidin-4-yloxy)-phenyl]-ethanone.

Y=20%

Preparation 2

1-[4-(1-methyl-piperidin-4-ylmethyl)-phenyl]-ethanone

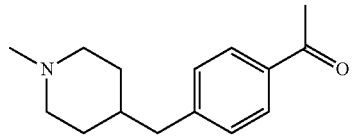

Step A

1-Methyl-piperidin-4-one (500 mg, 4.42 mmol) was dissolved in THF (10 ml) and added dropwise to a stirred mixture of (4-cyano-benzyl)-phosphonic acid diethyl ester (1.12 g, 4.42 mmol) and NaH (60% oil dispersion, 212 mg, 5.30 mmol) in THF (10 ml) under N$_2$. The solution was stirred at room temperature for 2 h, then partitioned between water and AcOEt. The organic phase was dried over Na$_2$SO$_4$ and evaporated in vacuo. The crude mixture was purified by silica gel chromatography (DCM/MeOH/NH$_4$OH 95:5:0.2). The collected fractions gave 392 mg of 4-(1-methyl-piperidin-4-ylidenemethyl)-benzonitrile as a yellow oil.

Y=42%

Step B

A solution of 4-(1-methyl-piperidin-4-ylidenemethyl)-benzonitrile (392 mg, 1.85 mmol) in toluene (5 ml) was added dropwise to a stirred solution of MeMgBr (3 M in Et$_2$O, 1.85 ml, 5.54 mmol) in toluene (10 ml) under N$_2$ atmosphere.

The resulting mixture was heated to 80° C. for 1 h then treated with 10% HCl and stirred at room temperature for 1 h. The phases were separated and the aqueous layer was washed with AcOEt and then brought to basic conditions with NH$_4$OH. The resulting slurry was extracted with AcOEt and the organic phase was dried over Na$_2$SO$_4$ and evaporated in vacuo to give 401 mg of 1-[4-(1-methyl-piperidin-4-ylidenemethyl)-phenyl]-ethanone.

Y=94%

Step C

1-[4-(1-methyl-piperidin-4-ylidenemethyl)-phenyl]-ethanone (401 mg, 1.75 mmol) was dissolved in EtOH (20 ml) and 5% Pd/C (40 mg) was added to the resulting solution. The mixture was hydrogenated in a Parr apparatus at 40 psi for 2 h. The catalyst was then filtered and the solvent was removed in vacuo. The residue was taken up with DCM and treated with HCl/Et$_2$O until reaching a pH value of 1. The solvent was removed in vacuo to give an oil which was allowed to crystallize. The solid was triturated in Et$_2$O and filtered to obtain 426 mg of 1-[4-(1-methyl-piperidin-4-ylmethyl)-phenyl]-ethanone as its hydrochloride salt.

Y=91%

Preparation 3

1-[4-((3R,5S)-3,4,5-trimethyl-piperazin-1-yl)-phenyl]-ethanone

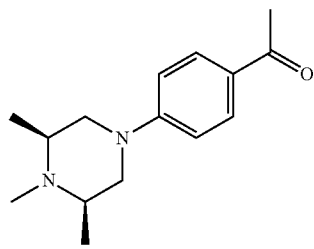

Step A

A mixture of 4-fluoro-benzonitrile (1.12 g, 9.25 mmol), (2R,6S)-2,6-dimethyl-piperazine (1.58 g, 13.9 mmol) and K$_2$CO$_3$ (3.20 g, 23.12 mmol) in DMSO (50 ml) was stirred at 130° C. for 24 h. The mixture was then partitioned between water and AcOEt and the organic phase was washed twice with water. The organic layer was then dried over Na$_2$SO$_4$ and evaporated in vacuo. The residue was taken up with Et$_2$O, treated with HCl/Et$_2$O and the resulting precipitate was filtered to give 2.2 g of 4-((3R,5S)-3,5-dimethyl-piperazin-1-yl)benzonitrile hydrochloride as a yellow powder.

Y=94%

Step B 4-((3R,5S)-3,5-dimethyl-piperazin-1-yl)-benzonitrile hydrochloride (1 g, 3.97 mmol) was dissolved in DCM (25 ml) and TEA (1.1 ml, 7.94 mmol). NaBH$_3$CN (374 mg, 5.96 mmol) and CH$_2$O (37% water solution, 0.446 ml, 5.96 mmol) were added to the resulting solution. The slurry was stirred overnight at room temperature, then further CH$_2$O (0.297 ml, 3.97 mmol) and NaBH$_3$CN (249 mg, 3.97 mmol) were added. The slurry was stirred at room temperature for 4 h, then brought to basic conditions with 5% NaHCO$_3$ and extracted twice with DCM. The collected organic phases were dried over Na$_2$SO$_4$ and evaporated in vacuo. The resulting oil was taken up with DCM and treated with HCl/Et$_2$O. The precipitate was filtered and washed with di-isopropylether to give 1 g of 4-((3R,5S)-3,4,5-trimethyl-piperazin-1-yl)-benzonitrile hydrochloride.

Y=95%

Step C

A solution of 4-((3R,5S)-3,4,5-trimethyl-piperazin-1-yl) benzonitrile (506 mg, 2.21 mmol) in toluene (10 ml) was added dropwise to a stirred solution of MeMgBr (3 M in Et$_2$O, 2.2 ml, 6.63 mmol) in toluene (10 ml) under N$_2$ atmosphere.

The resulting mixture was heated to 80° C. for 4 h, then treated with 10% HCl and heated to 80° C. for 1 h. The phases were separated and the aqueous layer was washed with AcOEt and then brought to basic conditions with NH₄OH. The resulting slurry was extracted with AcOEt and the organic phase was dried over Na₂SO₄ and evaporated in vacuo to give 481 mg of 1-[4-((3R,5S)-3,4,5-trimethyl-piperazin-1-yl)-phenyl]-ethanone as a yellow oil.

Y=88%

Preparation 4

1-[3-Chloro-5-(4-methyl-piperazin-1-yl)-phenyl]-ethanone

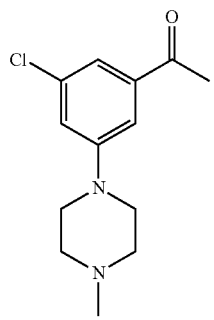

Step A

A mixture of 3-chloro-5-fluoro-benzonitrile (1 g, 6.45 mmol), 1-methyl-piperazine (0.715 ml, 6.45 mmol), and K₂CO₃ (2.64 g, 19.3 mmol) in DMF (5 ml) was heated to 140° C. for 40 min in a microwave apparatus. The resulting slurry was filtered and the solvent was removed in vacuo to give 1 g of 3-chloro-5-(4-methyl-piperazin-1-yl)-benzonitrile. The crude reaction mixture was used in the next step without any further purification.

Step B

A solution of 3-chloro-5-(4-methyl-piperazin-1-yl)-benzonitrile (1 g, crude mixture from step A) in toluene (5 ml) was added dropwise to a stirred solution of MeMgBr (3 M in Et₂O, 4.25 ml, 12.7 mmol) in toluene (5 ml) under N₂.

The resulting mixture was heated to 100° C. for 6 h, then cooled down to 0° C. and treated with 10% HCl. The mixture was refluxed for 1 h and then stirred at room temperature for 12 h. The phases were separated and the aqueous layer was brought to basic conditions with NH₄OH and extracted with DCM. The organic phase was dried over Na₂SO₄ and evaporated in vacuo. The crude material was purified by column chromatography (eluent: AcOEt/petroleum ether 9:1) to give 250 mg of 1-[3-chloro-5-(4-methyl-piperazin-1-yl)-phenyl]-ethanone as a yellow oil.

Preparation 5

Methanesulfonic acid 4-((E)-3-{4-[(E)-2-(tetrahydro-pyran-2-yloxycarbamoyl)-vinyl]-phenyl}-acryloyl)-benzyl ester

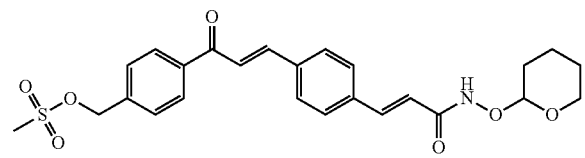

Step A

A mixture of 1-(4-hydroxymethyl-phenyl)-ethanone (1 g, 6.67 mmol), 4-formylcinnamic acid (1.17 g, 6.67 mmol) and 1.7 M KOH (5.89 ml) in EtOH (60 ml) was stirred at room temperature overnight. The resulting precipitate was filtered and washed with EtOH to give 1.39 g of (E)-3-{4-[(E)-3-(4-hydroxymethyl-phenyl)-3-oxo-propenyl]-phenyl}-acrylic acid as its potassium salt.

Y=60%

Step B

A mixture of (E)-3-{4-[(E)-3-(4-hydroxymethyl-phenyl)-3-oxo-propenyl]-phenyl}-acrylic acid potassium salt (1.39 g, 4.01 mmol), EDC (1.53 g, 8.03 mmol), HOBT (1.08 g, 8.03 mmol), TEA (1.11 ml, 8.03 mmol), NH₂OTHP (939 mg, 8.03 mmol) in THF (20 ml) and DMF (20 ml) was stirred at room temperature overnight and then partitioned between water and AcOEt. The organic phase was washed with water, dried over Na₂SO₄ and evaporated in vacuo. The resulting solid was triturated with di-isopropylether and filtered to give 1.15 g of (E)-3-{4-[(E)-3-(4-hydroxymethyl-phenyl)-3-oxo-propenyl]-phenyl}-N-(tetrahydro-pyran-2-yloxy)-acrylamide.

Y=70%

Step C

Methanesulfonyl chloride (388 mg, 3.39 mmol) was added to a stirred solution of (E)-3-{4-[(E)-3-(4-hydroxymethyl-phenyl)-3-oxo-propenyl]-phenyl}-N-(tetrahydro-pyran-2-yloxy)-acrylamide (1.15 g, 2.82 mmol) and TEA (1.18 ml, 8.46 mmol) in DCM (20 ml) and DMF (20 ml). The mixture was stirred at room temperature for 1 h and then additional methanesulfonyl chloride (258 mg, 2.25 mmol) and TEA (0.393 ml, 2.82 mmol) were added. After stirring for additional 1 h the solution was diluted with water and brought to basic conditions with 5% NaHCO₃. The resulting slurry was extracted with AcOEt and the organic phase was washed with water, dried over Na₂SO₄ and evaporated in vacuo. The crude reaction mixture was purified by column chromatography (eluent: petroleum ether/AcOEt 1:1) to give 277 mg of the title compound and 423 mg of (E)-3-{4-[(E)-3-(4-chloromethyl-phenyl)-3-oxo-propenyl]-phenyl}-N-(tetrahydro-pyran-2-yloxy)-acrylamide.

Preparation 6

1-((2R,6S)-2,6-Dimethyl-piperazin-1-yl)-ethanone

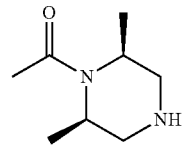

Step A

A solution of BOC₂O (1.05 g, 4.8 mmol) in DCM (10 ml) was added dropwise to a stirred solution of (2R,6S)-2,6-dimethyl-piperazine (500 mg, 4.38 mmol) and TEA (1.22 ml, 8.75 mmol) in DCM (20 ml) at 0° C. The mixture was stirred at room temperature for 4 h, the solvent was evaporated and the residue was partitioned between water and Et₂O. The organic phase was dried over Na₂SO₄, evaporated in vacuo and the crude reaction mixture was purified by column chromatography (eluent: DCM/MeOH/NH₄OH 97:3:0.1) to give 840 mg of (3S,5R)-3,5-dimethyl-piperazine-1-carboxylic acid tert-butyl ester as a yellow oil.

Y=89%

Step B

Acetyl chloride (0.216 ml, 3.04 mmol) was added to a stirred solution of (3S,5R)-3,5-dimethyl-piperazine-1-carboxylic acid tert-butyl ester (500 mg, 2.34 mmol) and TEA (0.49 ml, 3.51 mmol) in DCM (20 ml). The mixture was stirred at room temperature overnight, then the solvent was evaporated and the residue was partitioned between Et₂O and 5% citric acid. The organic phase was dried over Na₂SO₄ and evaporated in vacuo to give 545 mg of (3S,5R)-4-acetyl-3,5-dimethyl-piperazine-1-carboxylic acid tert-butyl ester as a colourless oil.

Y=90%

Step C (3S,5R)-4-Acetyl-3,5-dimethyl-piperazine-1-carboxylic acid tert-butyl ester (450 mg, 1.75 mmol) was dissolved in DCM (10 ml) and acidified with HCl/Et₂O. The mixture was stirred at room temperature for two days. The resulting solid was filtered to give 190 mg of 1-((2R,6S)-2,6-dimethyl-piperazin-1-yl)ethanone hydrochloride. The mother liquors were treated with HCl/Et₂O for 4 h and the resulting solid was filtered to give additional 43 mg of the title compound as hydrochloric salt.

Y=69%

Preparation 7

Methanesulfonic acid 3-((E)-3-{4-[(E)-2-(tetrahydro-pyran-2-yloxycarbamoyl)-vinyl]-phenyl}-acryloyl)-benzyl ester

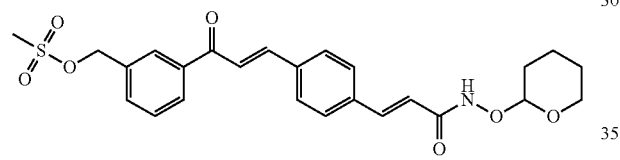

Step A

A mixture of 3-acetyl-benzaldehyde (850 mg, 5.74 mmol) and NaBH(OAc)₃ (2.44 g, 11.48 mmol) in toluene (15 ml) was stirred at 80° C. for 4 h. The resulting solution was brought to basic conditions with 2 N NaOH and extracted with AcOEt. The organic phase was dried over Na₂SO₄ and evaporated in vacuo to give 850 mg of crude mixture of 1-(3-hydroxymethyl-phenyl)-ethanone as a pale yellow oil.

Step B

A mixture of 1-(3-hydroxymethyl-phenyl)-ethanone (810 mg), 4-formylcinnamic acid (950 mg, 5.4 mmol) and 1.7 M KOH (6.4 ml) in EtOH (40 ml) was stirred at room temperature for 18 h. The resulting precipitate was filtered and washed with EtOH to give 1.25 g of (E)-3-{4-[(E)-3-(3-hydroxymethyl-phenyl)-3-oxo-propenyl]-phenyl}-acrylic acid as its potassium salt.

Step C

A mixture of (E)-3-{4-[(E)-3-(3-hydroxymethyl-phenyl)-3-oxo-propenyl]-phenyl}-acrylic acid potassium salt (1.25 g, 3.6 mmol), EDC (828 mg, 4.32 mmol), HOBT (584 mg, 4.32 mmol), TEA (1.0 ml, 7.2 mmol), NH₂OTHP (421 mg, 3.60 mmol) in THF (20 ml) and DMF (20 ml) was stirred at room temperature for 12 h and then partitioned between water and AcOEt. The organic phase was washed with water, dried over Na₂SO₄ and evaporated in vacuo. The crude reaction mixture was purified by column chromatography (eluent: petroleum ether/AcOEt 2:8) to give 1.2 g of (E)-3-{4-[(E)-3-(3-hydroxymethyl-phenyl)-3-oxo-propenyl]-phenyl}-N-(tetrahydro-pyran-2-yloxy)-acrylamide as a yellow powder.

Y=81%

Step D

Methanesulfonyl chloride (0.41 ml, 5.3 mmol) was added to a stirred solution of (E)-3-{4-[(E)-3-(3-hydroxymethyl-phenyl)-3-oxo-propenyl]-phenyl}-N-(tetrahydro-pyran-2-yloxy)-acrylamide (1.08 g, 2.68 mmol) and TEA (1.47 ml, 10.6 mmol) in DCM (18 ml) and DMF (12 ml). The mixture was stirred at room temperature for 30 min and then brought to basic conditions with 5% NaHCO₃. The resulting slurry was extracted with Et₂O and the organic phase was washed with water, dried over Na₂SO₄ and evaporated in vacuo. The crude reaction mixture was purified by column chromatography (eluent: petroleum ether/AcOEt 1:1) to give 600 mg of a mixture of the title compound and (E)-3-{4-[(E)-3-(3-chloromethyl-phenyl)-3-oxo-propenyl]-phenyl}-N-(tetrahydro-pyran-2-yloxy)-acrylamide as the main product.

Preparation 8

1-[3-((3R,5S)-3,4,5-Trimethyl-piperazin-1-yl)-phenyl]-ethanone

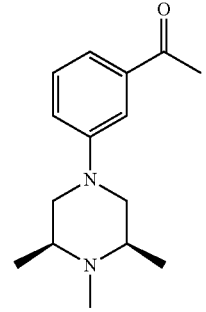

Step A

An oven-dried MW tube was charged with Pd₂(dba)₃ (592 mg, 0.65 mmol), K₃PO₄ (1.92 g, 9.06 mmol) and (2'-dicyclohexylphosphanyl-biphenyl-2-yl)-dimethyl-amine (127 mg, 0.32 mmol). The tube was purged and backfilled with N₂ and then 1-(3-chloro-phenyl)-ethanone (1 g, 6.47 mmol), (2R,6S)-2,6-dimethyl-piperazine (886 mg, 7.76 mmol) and DME (10 ml) were added. The mixture was heated in a MW apparatus for 4 h at 100° C. and then further Pd₂(dba)₃ (592 mg, 0.65 mmol) and (2'-dicyclohexylphosphanyl-biphenyl-2-yl)-dimethyl-amine (127 mg, 0.32 mmol) were added. The reaction mixture was heated to 100° C. for additional 10 h and then the solid was filtered off over a Celite pad. The filtrate was diluted with AcOEt and extracted with 1 M HCl. The aqueous phase was brought to basic conditions with NH₄OH and extracted with AcOEt. The organic phase was dried over Na₂SO₄ and evaporated in vacuo. The crude reaction mixture was purified by column chromatography (eluent: AcOEt/MeOH 8:2) to give 226 mg of 1-[3-((3R,5S)-3,5-dimethyl-piperazin-1-yl)-phenyl]-ethanone.

Y=15%

Step B

A mixture of 1-[3-((3R,5S)-3,5-dimethyl-piperazin-1-yl)-phenyl]-ethanone (226 mg, 0.974 mmol), NaBH(OAc)₃ (309 mg, 1.46 mmol) and CH₂O (37% water solution, 0.087 ml, 1.17 mmol) in DCM (10 ml) was stirred at room temperature overnight. The resulting solution was diluted with water, brought to basic conditions with NH₄OH and extracted with DCM. The organic phase was dried over Na₂SO₄ and evaporated in vacuo. The crude reaction mixture was purified by SCX cartridge (eluent: MeOH and then 3% NH₄OH in MeOH) to give 188 mg of 1-[3-((3R,5S)-3,4,5-trimethyl-piperazin-1-yl)-phenyl]-ethanone.
Y=78%

Preparation 9

4-(4-Acetyl-phenyl)-piperazine-1-carboxylic acid tert-butyl ester

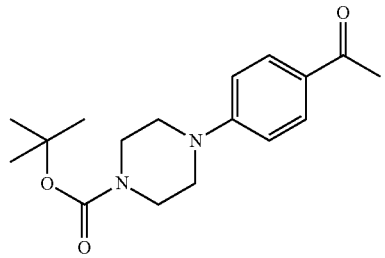

A mixture of 1-(4-piperazin-1-yl-phenyl)-ethanone (513 mg, 2.51 mmol), BOC$_2$O (820 mg, 3.76 mmol) and TEA (0.698 ml, 5.02 mmol) in DCM (20 ml) was stirred at room temperature overnight. The resulting solution was concentrated in vacuo and then partitioned between water and AcOEt. The organic phase was dried over Na$_2$SO$_4$, evaporated in vacuo and the crude reaction mixture was purified by column chromatography (eluent: petroleum ether/AcOEt) to give 701 mg of 4-(4-acetyl-phenyl)-piperazine-1-carboxylic acid tert-butyl ester.
Y=92%

Preparation 10

1-[5-Chloro-2-(4-methyl-piperazin-1-yl)-phenyl]-ethanone

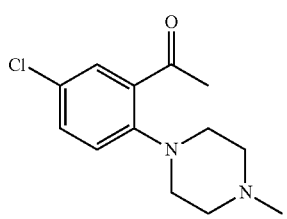

Step A
A mixture of 5-chloro-2-fluoro-benzonitrile (500 mg, 3.21 mmol), K$_2$CO$_3$ (1.32 g, 9.64 mmol) and 1-methyl-piperazine (482 mg, 4.81 mmol) in DMSO (6.4 ml) was stirred at 100° C. for 6 h and then partitioned between water and Et$_2$O. The organic phase was dried over Na$_2$SO$_4$ and evaporated in vacuo. The crude mixture was purified by column chromatography (eluent: DCM/MeOH/NH$_4$OH 98:2:0.1) to give 660 mg of 5-chloro-2-(4-methyl-piperazin-1-yl)-benzonitrile.
Y=87%
Step B
A solution of 5-chloro-2-(4-methyl-piperazin-1-yl)-benzonitrile (660 mg, 2.80 mmol) in dry toluene (6 ml) was added dropwise to a stirred solution of MeMgBr (3 M in Et$_2$O, 2.8 ml, 8.42 mmol) under N$_2$ atmosphere.
The resulting mixture was heated to 80° C. for 4 h, then treated with 10% HCl until reaching a pH value of 1 and extracted with AcOEt. The phases were separated and the aqueous layer was brought to basic conditions with Na$_2$CO$_3$ and extracted with AcOEt. The organic phase was dried over Na$_2$SO$_4$ and evaporated in vacuo to give 570 mg of 1-[5-chloro-2-(4-methyl-piperazin-1-yl)-phenyl]-ethanone as a yellow powder.
Y=81%

Preparation 11

1-[2-(4-Methyl-piperazin-1-ylmethyl)-phenyl]-ethanone

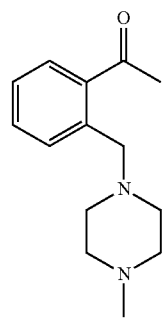

A mixture of 2-acetyl-benzaldehyde (1 g, 6.75 mmol), N-methyl piperazine (878 mg, 8.76 mmol) and NaBH(OAc)$_3$ (2.14 g, 10.12 mmol) in DCM (50 ml) was stirred at room temperature for 1 h and then acetic acid (526 mg, 8.76 mmol) was added. The resulting solution was stirred at room temperature overnight and then diluted with DCM and washed with 1 M Na$_2$CO$_3$. The organic phase was dried over Na$_2$SO$_4$ and evaporated in vacuo. The crude mixture was purified by column chromatography (eluent: DCM/MeOH/NH$_4$OH 95:5:0.2) to give 1.06 g of 1-[2-(4-methyl-piperazin-1-ylmethyl)-phenyl]-ethanone.
Y=67%

Preparation 12

4-(4-Acetyl-benzyl)-piperazine-1-carboxylic acid tert-butyl ester

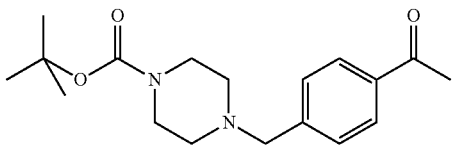

Step A
Methanesulfonyl chloride (0.335 ml, 5.05 mmol) was added dropwise to a stirred solution of 1-(4-hydroxymethyl-phenyl)-ethanone (500 mg, 3.37 mmol) and TEA (0.928 ml, 6.74 mmol) in DCM (25 ml). The resulting mixture was stirred at room temperature for 3 h and then the solvent was removed in vacuo. The residue was partitioned between water and Et$_2$O and the organic phase was dried over Na$_2$SO$_4$ and evaporated in vacuo to give 580 mg of a 1:1 mixture of 1-(4-methanesulfonylmethyl-phenyl)-ethanone and 1-(4-chloromethyl-phenyl)-ethanone, which was used in the next step without further purification.

Step B

N-Boc piperazine (485 mg, 2.61 mmol) was added to a stirred solution of a mixture of 1-(4-methanesulfonylmethyl-phenyl)-ethanone, 1-(4-chloromethyl-phenyl)-ethanone (obtained in STEP A, 580 mg) and TEA (0.522 ml, 3.75 mmol) in $CH_3CN$ (5 ml). The resulting mixture was stirred at room temperature overnight and then further TEA (0.250 ml, 1.80 mmol) and N-Boc piperazine (100 mg, 0.53 mmol) were added. After 4 h the solution was partitioned between water and AcOEt, the organic phase was dried over $Na_2SO_4$ and evaporated in vacuo. The crude mixture was purified by column chromatography (eluent: petroleum ether/AcOEt 7:3 to 6:4) to give 700 mg of 4-(4-acetyl-benzyl)-piperazine-1-carboxylic acid tert-butyl ester.

Preparation 13

1-[2-Chloro-5-(4-methyl-piperazin-1-yl)-phenyl]-ethanone

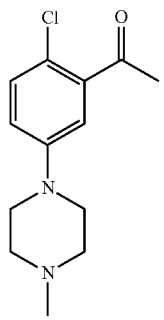

Step A

A mixture of 2-chloro-5-fluoro-benzonitrile (1 g, 6.43 mmol), $K_2CO_3$ (2.66 g, 19.3 mmol) and 1-methyl-piperazine (1.02 g, 10.26 mmol) in DMSO (14 ml) was stirred at 100° C. overnight and then further 1-methyl-piperazine (1.02 g, 10.26 mmol) was added. The mixture was stirred at 100° C. overnight and then partitioned between water and $Et_2O$. The organic phase was extracted with 1 M HCl and the aqueous layer was brought to basic conditions with $NH_4OH$ and extracted with DCM. The organic phase was dried over $Na_2SO_4$ and evaporated in vacuo to give 1 g of 2-chloro-5-(4-methyl-piperazin-1-yl)-benzonitrile.
Y=66%

Step B

A solution of 2-chloro-5-(4-methyl-piperazin-1-yl)-benzonitrile (1 g, 4.24 mmol) in dry toluene (12 ml) was added dropwise to a stirred solution of MeMgBr (3 M in $Et_2O$, 4.24 ml, 12.73 mmol) in dry toluene (8 ml) under $N_2$ atmosphere.

The mixture was heated to 80° C. for 4 h, and then acidified with 10% HCl. The resulting mixture were stirred for 2 h at room temperature and then separated. The aqueous phase was brought to basic conditions with $NH_4OH$ and extracted with AcOEt. The organic phase was dried over $Na_2SO_4$ and evaporated in vacuo to give 1.02 g of 1-[2-chloro-5-(4-methyl-piperazin-1-yl)-phenyl]-ethanone.
Y=94%

Preparation 14

1-[3-(4-Methyl-piperazin-1-ylmethyl)-phenyl]-ethanone

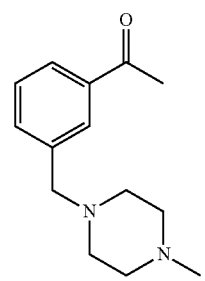

Step A

A mixture of 3-formyl-benzonitrile (1.5 g, 11.45 mmol), N-methyl piperazine (1.49 g, 14.9 mmol) and $NaBH(OAc)_3$ (3.63 g, 17.18 mmol) in DCM (75 ml) and $CH_3COOH$ (0.851 ml, 14.9 mmol) was stirred overnight at room temperature, then diluted with DCM and washed with 1 M $Na_2CO_3$. The organic phase was dried over $Na_2SO_4$ and evaporated in vacuo. The crude mixture was purified by column chromatography (eluent: DCM/MeOH/$NH_4OH$ 97:3:0.5) to give 1.7 g of 3-(4-methyl-piperazin-1-ylmethyl)-benzonitrile.
Y=70%

Step B

A solution of 3-(4-methyl-piperazin-1-ylmethyl)-benzonitrile (1.7 g, 7.91 mmol) in dry toluene (20 ml) was added dropwise to a stirred solution of MeMgBr (3 M in $Et_2O$, 7.91 ml, 23.72 mmol) under $N_2$ atmosphere at 0° C.

The mixture was heated to 80° C. for 6 h and then kept at room temperature overnight. The resulting slurry was treated with 10% HCl and ice for 1 h and than brought to basic conditions with 1 M NaOH and extracted with AcOEt. The organic phase was dried over $Na_2SO_4$ and evaporated in vacuo. The crude mixture was purified by column chromatography (eluent: DCM/MeOH/$NH_4OH$ from 97:3:0.1 to 95:5:0.2) to give 1.69 g of 1-[3-(4-methyl-piperazin-1-ylmethyl)-phenyl]-ethanone.
Y=92%

Example 16

(E)-3-(4-{(E)-3-[4-(4-Benzoyl-piperazin-1-yl)-phenyl]-3-oxo-propenyl}-phenyl)-N-hydroxy-acrylamide

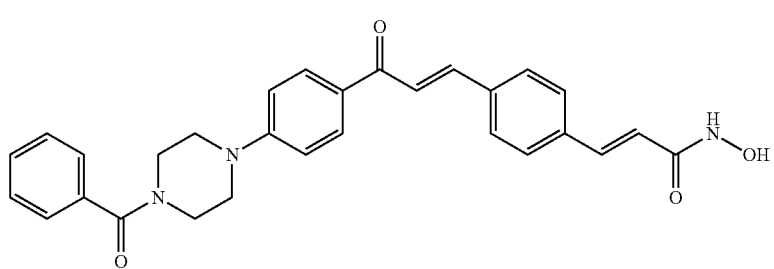

Step A

Benzoyl chloride (0.341 ml, 2.94 mmol) was added dropwise to a stirred mixture of 1-(4-piperazin-1-yl-phenyl)-ethanone (500 mg, 2.45 mmol) and TEA (0.681 ml, 4.9 mmol) in DCM (25 ml). The resulting solution was stirred overnight at room temperature, then diluted with DCM and washed with water, with $NaHCO_3$ (5% in $H_2O$) and finally with citric acid (20% in $H_2O$). The organic phase was dried over $Na_2SO_4$ and evaporated in vacuo. The resulting solid was triturated with di-isopropylether and filtered to give 687 mg of 1-[4-(4-benzoyl-piperazin-1-yl)-phenyl]-ethanone.

Y=91%

Step B

1-[4-(4-Benzoyl-piperazin-1-yl)-phenyl]-ethanone (500 mg, 1.62 mmol) was dissolved in 1,4-dioxane (3 ml) and added to a stirred solution of 4-formylcinnamic acid (286 mg, 1.62 mmol) and 1.7 M KOH (1.9 ml) in EtOH (5 ml) and water (5 ml). The resulting mixture was stirred overnight at room temperature and then heated to 40° C. for 4 h. The reaction was then quenched with 10% HCl, the resulting precipitate was filtered and washed with EtOH. The resulting green solid was dried in vacuo to give 240 mg of (E)-3-(4-{(E)-3-[4-(4-benzoyl-piperazin-1-yl)-phenyl]-3-oxo-propenyl}-phenyl)-acrylic acid as its hydrochloride salt.

Y=30%

Step C

A mixture of (E)-3-(4-{(E)-3-[4-(4-benzoyl-piperazin-1-yl)-phenyl]-3-oxo-propenyl}-phenyl)-acrylic acid hydrochloride (200 mg, 0.398 mmol), HOBT (107.4 mg, 0.796 mmol), EDC (152 mg, 0.796 mmol), TEA (0.111 ml, 0.796 mmol) and $NH_2OTHP$ (56 mg, 0.477 mmol) in THF (5 ml) and DMF (5 ml) was stirred overnight at room temperature and then partitioned between water and AcOEt. The organic phase was dried over $Na_2SO_4$ and evaporated in vacuo. The crude mixture was purified by silica gel chromatography (eluent: DCM/MeOH 98:2) and the resulting product was dissolved in DCM and treated with $HCl/Et_2O$ for 2 h. The precipitate was filtered giving 115 mg of (E)-3-(4-{(E)-3-[4-(4-benzoyl-piperazin-1-yl)-phenyl]-3-oxo-propenyl}-phenyl)-N-hydroxy acrylamide as its hydrochloride salt.

Yield=56%

LC-MS: Method C, rt=1.94; (ES+) $MH^+$: 482.1

'1H NMR (DMSO-$d_6$, +TFA) δ (ppm): 8.08 (d, 2H), 7.95 (d, 1H), 7.90 (d, 2H), 7.66 (d, 1H), 7.63 (d, 2H), 7.33-7.57 (m, 6H), 7.04 (d, 2H), 6.59 (d, 1H), 3.41-3.72 (m, 8H).

Example 17

(E)-3-(4-{(E)-3-[4-(4-Acetyl-piperazin-1-yl)-phenyl]-3-oxo-propenyl}-phenyl)-N-hydroxy-acrylamide

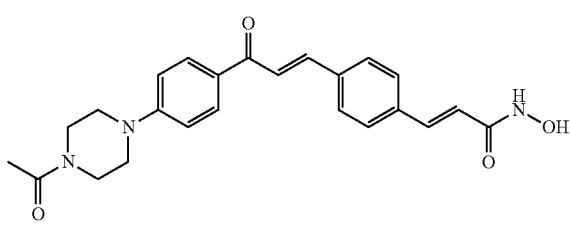

Step A

A mixture of 1-[4-(4-acetyl-piperazin-1-yl)-phenyl]-ethanone (prepared following the procedure described in Example 16 STEP A, 533 mg, 2.16 mmol), 4-formylcinnamic acid (381 mg, 2.16 mmol) and 1.7 M KOH (2.54 ml) in EtOH (15 ml) and water (3 ml) was stirred overnight at room temperature. The resulting precipitate was filtered to get 260 mg of (E)-3-(4-{(E)-3-[4-(4-acetyl-piperazin-1-yl)-phenyl]-3-oxo-propenyl}-phenyl)-acrylic acid as its potassium salt. The mother liquors were acidified with 10% HCl and the resulting green precipitate was filtered to give 240 mg of (E)-3-(4-{(E)-3-[4-(4-acetyl-piperazin-1-yl)-phenyl]-3-oxo-propenyl}-phenyl)-acrylic acid hydrochloride. The mixture of both, the potassium salt and of the hydrochloric salt, was used in the next step without any further purification.

Step B (E)-3-(4-{(E)-3-[4-(4-Acetyl-piperazin-1-yl)-phenyl]-3-oxo-propenyl}-phenyl)-acrylic acid (mixture of potassium salt and hydrochloric salt, 200 mg) was dissolved in THF (5 ml), DMF (5 ml) and TEA (0.126 ml, 0.908 mmol), then HOBT (122 mg, 0.908 mmol), EDC (173 mg, 0.908 mmol) and $NH_2OTHP$ (63.7 mg, 0.545 mmol) were added to the resulting solution. The mixture was stirred overnight at room temperature and then partitioned between water and AcOEt. The organic phase was dried over $Na_2SO_4$ and evaporated in vacuo. The crude mixture was purified by silica gel chromatography (eluent: DCM/MeOH/$NH_4OH$ 96:4:0.2). The resulting product was dissolved in DCM and treated with $HCl/Et_2O$ for 1 h. The precipitate was filtered and crystallized from $H_2O/CH_3CN/DMSO$ to give 20 mg of (E)-3-(4-{(E)-3-[4-(4-acetyl-piperazin-1-yl)-phenyl]-3-oxo-propenyl}-phenyl)-N-hydroxy-acrylamide hydrochloride.

LC-MS: Method E, rt=1.54; (ES+) $MH^+$: 420.2

'1H NMR (DMSO-$d_6$) δ (ppm): 10.77 (bs, 1H), 8.08 (m, 2H), 7.95 (d, 1H), 7.90 (d, 2H), 7.66 (d, 1H), 7.60-7.66 (m, 2H), 7.49 (d, 1H), 7.03 (m, 2H), 6.55 (d, 1 H), 3.56-3.67 (m, 4H), 3.43-3.46 (m, 2H), 3.36-3.41 (m, 2H), 2.05 (s, 3H).

Example 18

(E)-N-Hydroxy-3-(4-{(E)-3-[4-(4-methanesulfonyl-piperazin-1-yl)-phenyl]-3-oxo-propenyl}-phenyl)-acrylamide

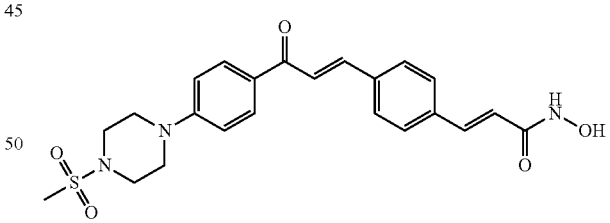

Step A

1-[4-(4-Methanesulfonyl-piperazin-1-yl)-phenyl]-ethanone (obtained following the experimental procedure described in Example 16 STEP A, 500 mg, 1.77 mmol) was dissolved in 1,4-dioxane (3 ml) and added to a stirred solution of 4-formylcinnamic acid (312 mg, 1.77 mmol) and 1.7 M KOH (2 ml) in EtOH (5 ml) and water (5 ml). The resulting mixture was stirred overnight at room temperature and then heated to 40° C. for 6 h. The resulting precipitate was filtered to give 470 mg of (E)-3-(4-{(E)-3-[4-(4-methanesulfonyl-piperazin-1-yl)-phenyl]-3-oxo-propenyl}-phenyl)-acrylic acid as its potassium salt.

Y=55%

Step B (E)-3-(4-{(E)-3-[4-(4-Methanesulfonyl-piperazin-1-yl)-phenyl]-3-oxo-propenyl}-phenyl)-acrylic acid potassium salt (190 mg, 0.398 mmol) was dissolved in THF (5 ml), DMF (5 ml) and TEA (0.111 ml, 0.796 mmol). HOBT (107.4 mg, 0.796 mmol), EDC (152 mg, 0.796 mmol) and NH$_2$OTHP (56 mg, 0.477 mmol) were added to the resulting solution. The mixture was stirred overnight at room temperature and then partitioned between water and AcOEt. The organic phase was dried over Na$_2$SO$_4$ and evaporated in vacuo. The crude mixture was purified by silica gel chromatography (eluent: DCM/MeOH 98:2). The resulting product was dissolved in DCM and treated with HCl/Et$_2$O for 2 h. The precipitate was filtered and washed with DCM to give 20 mg of (E)-N-hydroxy-3-(4-{(E)-3-[4-(4-methanesulfonyl-piperazin-1-yl)-phenyl]-3-oxo-propenyl}-phenyl)-acrylamide hydrochloride.

Yield=11%

LC-MS: Method C, rt=1.75; (ES+) MH$^+$: 456.0

$^1$H NMR (DMSO-d$_6$) δ (ppm): 8.09 (m, 2H), 7.95 (d, 1H), 7.90 (d, 2H), 7.67 (d, 1 H), 7.63 (d, 2H), 7.49 (d, 1H), 7.08 (m, 2H), 6.56 (d, 1H), 3.48-3.55 (m, 4H), 3.20-3.31 (m, 4H), 2.92 (s, 3H).

Example 19

4-(4-{(E)-3-[4-((E)-2-Hydroxycarbamoyl-vinyl)-phenyl]-acryloyl}-phenyl)-piperazine-1-carboxylic acid dimethylamide

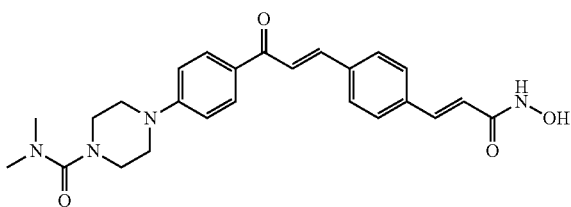

The product was obtained starting from 4-(4-acetyl-phenyl)-piperazine-1-carboxylic acid dimethylamide (obtained following the procedure in Example 16 STEP A) and 4-formylcinnamic acid, following the experimental procedure described in Example 17 STEP A and B. The title compound was obtained as its hydrochloride salt.

LC-MS: Method C, rt=2.62; (ES+) MH$^+$: 449.1

$^1$H NMR (DMSO-d$_6$) δ (ppm): 8.07 (m, 2H), 7.95 (d, 1H), 7.90 (d, 2H), 7.66 (d, 1 H), 7.63 (d, 2H), 7.48 (d, 1H), 7.03 (m, 2H), 6.57 (d, 1H), 3.37-3.47 (m, 4H), 3.20-3.33 (m, 4H), 2.79 (s, 6H).

Example 20

4-(4-{(E)-3-[4-((E)-2-Hydroxycarbamoyl-vinyl)-phenyl]-acryloyl}-phenyl)-piperazine-1-carboxylic acid amide

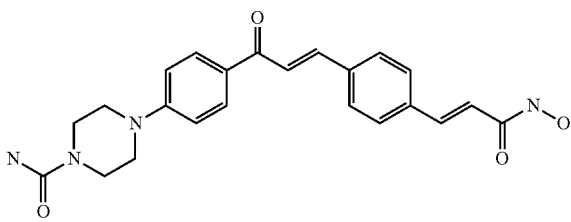

Step A 1-(4-Piperazin-1-yl-phenyl)-ethanone (500 mg, 2.45 mmol) was dissolved in DCM (20 ml) and NaOCN (318.6 mg, 4.90 mmol) and AcOH (0.28 ml, 4.90 mmol) were added to the resulting solution. The mixture was stirred at room temperature for 36 h and the resulting precipitate was filtered off, washed with DCM and water to give 675 mg of 4-(4-acetyl-phenyl)-piperazine-1-carboxylic acid amide (crude compound was used without further purification in the next step).

Step B

A mixture of 4-(4-acetyl-phenyl)-piperazine-1-carboxylic acid amide (crude mixture from STEP A, 300 mg), 4-formylcinnamic acid (214 mg, 1.21 mmol) and 1.7 M KOH (1.42 ml) in MeOH (10 ml) was stirred at room temperature overnight and then heated to 50° C. for 8 h. After stirring at room temperature for additional 72 h the mixture was heated to 50° C. for 4 h then quenched with 10% HCl. The resulting precipitate was filtered off and washed with MeOH to give 316 mg of (E)-3-(4-{(E)-3-[4-(4-carbamoyl-piperazin-1-yl)-phenyl]-3-oxo-propenyl}-phenyl)-acrylic acid hydrochloride.

Step C (E)-3-(4-{(E)-3-[4-(4-Carbamoyl-piperazin-1-yl)-phenyl]-3-oxo-propenyl}-phenyl)-acrylic acid hydrochloride (316 mg, 0.716 mmol) was suspended in DMF (5 ml). HOBT (193 mg, 1.43 mmol), EDC (273 mg, 1.43 mmol), TEA (0.200 ml, 1.43 mmol) and NH$_2$OTHP (100 mg, 0.86 mmol) were added. The mixture was stirred at room temperature for 72 h and then partitioned between water and hot AcOEt. The organic extract was dried over Na$_2$SO$_4$, evaporated in vacuo and the crude product was crystallized from DCM/Et$_2$O. The resulting solid was suspended in DCM and treated with HCl/Et$_2$O for 1 h. The precipitate was filtered off, giving 103 mg of 4-(4-{(E)-3-[4-((E)-2-hydroxycarbamoyl-vinyl)-phenyl]-acryloyl}-phenyl)-piperazine-1-carboxylic acid amide as its hydrochloride salt.

Yield=31%

LC-MS: Method C, rt=1.44; (ES+) MH$^+$: 421.06

$^1$H NMR (DMSO-d$_6$+TFA) δ (ppm): 8.06 (d, 2H), 7.94 (d, 1H), 7.89 (d, 2H), 7.65 (d, 1H), 7.63 (d, 2H), 7.48 (d, 1H), 7.04 (d, 2H), 6.57 (d, 1H), 3.43-3.51 (m, 4 H), 3.32-3.42 (m, 4H).

Example 21

4-(4-{(E)-3-[4-((E)-2-Hydroxycarbamoyl-vinyl)-phenyl]-acryloyl}-phenyl)-piperazine-1-carboxylic acid ethyl ester

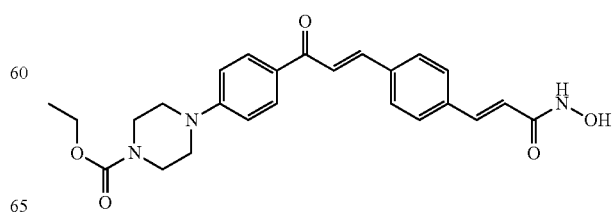

The product was obtained starting from 4-(4-acetyl-phenyl)-piperazine-1-carboxylic acid ethyl ester (obtained following the experimental procedure described in Example 16 STEP A) and 4-formylcinnamic acid, following the experimental procedure described in Example 16 STEP B and C. The title compound was obtained as its hydrochloride salt.

LC-MS: Method C, rt=1.99; (ES+) MH+: 450.1

$^1$H NMR (DMSO-d$_6$) δ (ppm): 8.07 (d, 2H), 7.95 (d, 1H), 7.90 (d, 2H), 7.66 (d, 1 H), 7.63 (d, 2H), 7.49 (d, 1H), 7.03 (d, 2H), 6.56 (d, 1H), 4.08 (q, 2H), 3.48-3.56 (m, 4H), 3.36-3.46 (m, 4H), 1.21 (t, 3H).

Example 22

(E)-N-Hydroxy-3-(4-{(E)-3-[4-(1-methyl-piperidin-4-yloxy)-phenyl]-3-oxo-propenyl}-phenyl)-acrylamide

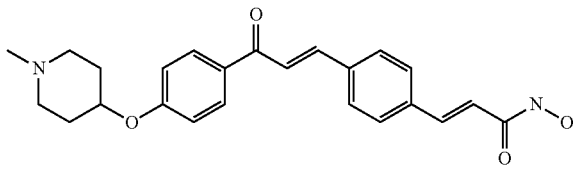

The product was obtained starting from 1-[4-(1-methyl-piperidin-4-yloxy)-phenyl]-ethanone (prepared as described in Preparation 1) and 4-formylcinnamic acid, following the experimental procedure described for Example 1 (STEP C and D). The title compound was purified by preparative LC-MS and was obtained as its trifluoroacetate salt.

LC-MS: Method C, rt=1.74; (ES+) MH+: 407.4

$^1$H NMR (DMSO-d$_6$) δ (ppm): 10.47 (bs, 1H), 9.30 (bs, 1H), 8.14 (m, 2H), 7.80-7.91 (m, 3H), 7.69 (d, 1H), 7.64 (d, 2H), 7.50 (d, 1H), 7.16 (m, 2H), 6.62 (d, 1 H), 4.68-4.98 (m, 1H), 2.96-3.57 (m, 6H), 2.86 (s, 3H), 1.97-2.26 (m, 2H).

Example 23

(E)-N-Hydroxy-3-(4-{(E)-3-[4-(1-methyl-piperidin-4-ylmethyl)-phenyl]-3-oxo-propenyl}-phenyl)-acrylamide

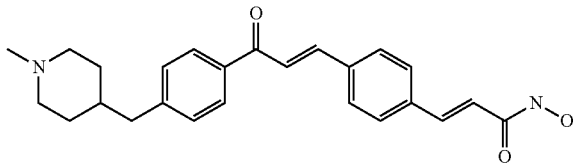

Step A

A mixture of 1-[4-(1-methyl-piperidin-4-ylmethyl)-phenyl]-ethanone hydrochloride (prepared as described in Preparation 2, 426 mg, 1.59 mmol), 4-formylcinnamic acid (280 mg, 1.59 mmol) and 1.7 M KOH (2.8 ml) in EtOH (7 ml) was stirred at room temperature overnight. The mixture was acidified with 10% HCl and the resulting precipitate was filtered off to give 388 mg of (E)-3-(4-{(E)-3-[4-(1-methyl-piperidin-4-ylmethyl)-phenyl]-3-oxo-propenyl}-phenyl)-acrylic acid hydrochloride.

Y=57%

Step B (E)-3-(4-{(E)-3-[4-(1-methyl-piperidin-4-ylmethyl)-phenyl]-3-oxo-propenyl}-phenyl)-acrylic acid hydrochloride (160 mg, 0.376) was dissolved in THF (5 ml), and then HOBT (66.5 mg, 0.493 mmol), EDC (94.6 mg, 0.493 mmol), TEA (0.171 ml, 1.233 mmol) and NH$_2$OTHP (47.6 mg, 0.411 mmol) were added to the resulting solution. The mixture was stirred overnight at room temperature and then partitioned between water and AcOEt. The organic extracts were dried over Na$_2$SO$_4$ and evaporated in vacuo. The crude mixture was dissolved in DCM and treated with HCl/Et$_2$O for 2 h. The precipitate was filtered off to give 90 mg (E)-N-hydroxy-3-(4-{(E)-3-[4-(1-methyl-piperidin-4-ylmethyl)-phenyl]-3-oxo-propenyl}-phenyl)-acrylamide hydrochloride.

Yield=54%

LC-MS: Method C, rt=1.45; (ES+) MH+: 405.2

$^1$H NMR (DMSO-d$_6$+TFA) δ (ppm): 9.72 (bs, 1H), 8.11 (d, 2H), 7.96 (d, 1H), 7.92 (d, 2H), 7.73 (d, 1H), 7.65 (d, 2H), 7.49 (d, 1H), 7.40 (d, 2H), 6.57 (d, 1H), 3.29-3.44 (m, 2H), 2.72-2.94 (m, 2H), 2.70 (d, 3H), 2.65 (d, 2H), 1.66-1.95 (m, 3H), 1.33-1.64 (m, 2H).

Example 24

(E)-N-Hydroxy-3-(4-{(E)-3-oxo-3-[4-((3R,5S)-3,4,5-trimethyl-piperazin-1-yl)-phenyl]-propenyl}-phenyl)-acrylamide

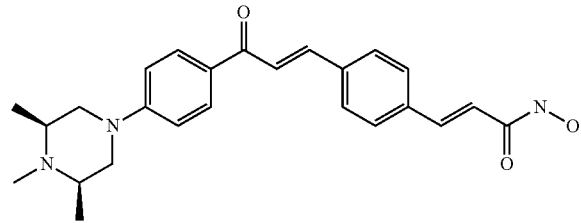

The product was obtained starting from 1-[4-((3R,5S)-3,4,5-trimethyl-piperazin-1-yl)-phenyl]-ethanone (prepared as described in Preparation 3) and 4-formylcinnamic acid, following the experimental procedure described for Example 1 (STEP C and D). The title compound was obtained as its hydrochloride salt.

LC-MS: Method D, rt=3.28; (ES+) MH+: 420.2

$^1$H NMR (DMSO-d$_6$) δ (ppm): 10.95 (bs, 1H), 8.10 (d, 2H), 7.96 (d, 1H), 7.91 (d, 2H), 7.68 (d, 1H), 7.64 (d, 2H), 7.49 (d, 1H), 7.15 (d, 2H), 6.58 (d, 1H), 4.18 (d, 2H), 3.26-3.49 (m, 2H), 3.10-3.25 (m, 2H), 2.80 (d, 3H), 1.44 (d, 6H).

Example 25

(E)-3-(4-{(E)-3-[3-Chloro-5-(4-methyl-piperazin-1-yl)-phenyl]-3-oxo-propenyl}-phenyl)-N-hydroxy-acrylamide

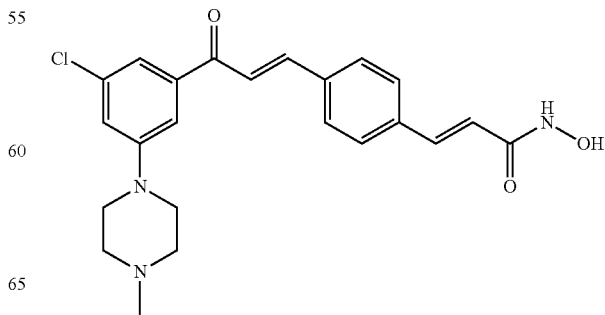

Step A

A mixture of 1-[3-chloro-5-(4-methyl-piperazin-1-yl)-phenyl]-ethanone (prepared as described in Preparation 4, 300 mg, 1.19 mmol), KOH (133 mg, 2.38 mmol) and (E)-3-(4-formyl-phenyl)-acrylic acid tert-butyl ester (276 mg, 1.19 mmol) in EtOH (10 ml) and H$_2$O (2 ml) was stirred at −20° C. for 1 h and then at room temperature for 12 h. The resulting mixture was partitioned between water and AcOEt and the organic phase was dried over Na$_2$SO$_4$ and evaporated in vacuo. The crude reaction mixture was purified by column chromatography (eluent: AcOEt/MeOH 9:1). The collected fractions were evaporated in vacuo and the resulting powder was dissolved in DCM (5 ml) and TFA (1 ml). The solution was stirred at room temperature for 12 h and then the solvent was removed to give 40 mg (E)-3-(4-{(E)-3-[3-chloro-5-(4-methyl-piperazin-1-yl)-phenyl]-3-oxo-propenyl}-phenyl)-acrylic acid as its trifluoroacetate salt.

Y=6%

Step B (E)-3-(4-{(E)-3-[3-Chloro-5-(4-methyl-piperazin-1-yl)-phenyl]-3-oxo-propenyl}-phenyl)-acrylic acid trifluoroacetate (40 mg, 0.076 mmol) was suspended in THF (5 ml). HOBT (16 mg, 0.116 mmol), EDC (22.3 mg, 0.116 mmol), TEA (0.04 ml, 0.291 mmol) and NH$_2$OTHP (12 mg, 0.097 mmol) were added to the resulting mixture. The reaction was stirred at room temperature overnight and then partitioned between water and AcOEt. The organic phase was dried over Na$_2$SO$_4$, evaporated in vacuo and the crude product was purified by column chromatography (eluent: AcOEt/MeOH 9:1). The collected fractions were evaporated and the resulting product was dissolved in DCM and treated with HCl/Et$_2$O for 1 h. The precipitate was filtered and purified by preparative LC-MS to give 20 mg of (E)-3-(4-{(E)-3-[3-Chloro-5-(4-methyl-piperazin-1-yl)-phenyl]-3-oxo-propenyl}-phenyl)-N-hydroxy-acrylamide as its trifluoroacetate salt.

Y=48%

LC-MS: Method C, rt=1.57; (ES+) MH$^+$: 426.31

$^1$H NMR (DMSO-d$_6$) δ (ppm): 10.79 (bs, 1H), 9.69 (bs, 1H), 7.96 (m, 2H), 7.94 (d, 1H), 7.77 (d, 1H), 7.62-7.71 (m, 3H), 7.56-7.60 (m, 1H), 7.51 (d, 1H), 7.38 (d, 1H), 6.56 (d, 1H), 3.98-4.13 (m, 2H), 3.43-3.62 (m, 2H), 2.94-3.25 (m, 4H), 2.87 (s, 3H).

Example 26

(E)-N-Hydroxy-3-{4-[(E)-3-oxo-3-(4-piperazin-1-ylmethyl-phenyl)-propenyl]-phenyl}-acrylamide

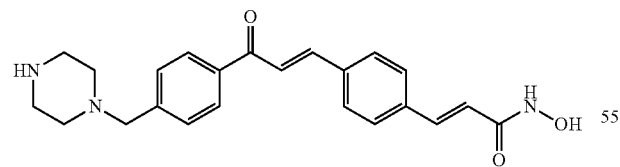

N-Boc-piperazine (46 mg, 0.246 mmol) was added to a stirred mixture of methanesulfonic acid 4-((E)-3-{4-[(E)-2-(tetrahydro-pyran-2-yloxycarbamoyl)-vinyl]-phenyl}-acryloyl)-benzyl ester (prepared as described in Preparation 5, 100 mg, 0.206 mmol) and TEA (0.057 ml, 0.412 mmol) in DMF (1 ml) and DCM (1 ml). The resulting solution was stirred at room temperature for 1 h. The mixture was diluted with water and extracted with AcOEt. The organic phase was washed with water, dried over Na$_2$SO$_4$ and evaporated in vacuo. The crude mixture was purified by column chromatography (eluent: DCM/MeOH/NH$_4$OH 99:1:0.2). The resulting product was dissolved in DCM and treated with HCl/Et$_2$O for 4 h. The precipitate was filtered off and rinsed with DCM to give 42.6 mg of (E)-N-hydroxy-3-{4-[(E)-3-oxo-3-(4-piperazin-1-ylmethyl-phenyl)-propenyl]-phenyl}-acrylamide as its bis-hydrochloride salt.

Y=44%

LC-MS: Method C, rt=1.16; (ES+) MH$^+$: 392.19

$^1$H NMR (DMSO-d$_6$+TFA) δ (ppm): 9.52 (bs, 3H), 8.24 (d, 2H), 8.00 (d, 1H), 7.94 (m, 2H), 7.85 (m, 2H), 7.77 (d, 1H), 7.66 (d, 2H), 7.49 (d, 1H), 6.58 (d, 1H), 4.48 (s, 2H), 3.23-3.56 (m, 8H).

Example 27

(E)-3-(4-{(E)-3-[4-(4-Benzyl-piperazin-1-ylmethyl)-phenyl]-3-oxo-propenyl}-phenyl)-N-hydroxy-acrylamide

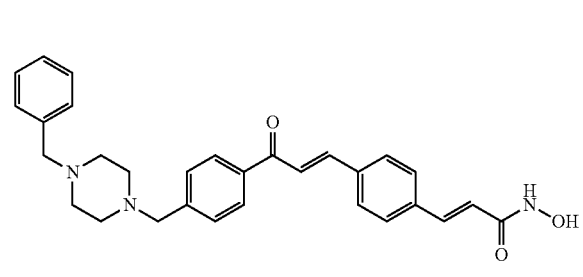

1-Benzyl-piperazine (40 mg, 0.22 mmol) was added to a stirred mixture of methanesulfonic acid 4-((E)-3-{4-[(E)-2-(tetrahydro-pyran-2-yloxycarbamoyl)-vinyl]-phenyl}-acryloyl)-benzyl ester (prepared as described in Preparation 5, 90 mg, 0.185 mmol) and TEA (0.052 ml, 0.37 mmol) in DMF (2 ml). The resulting solution was stirred at room temperature for 1 h. The mixture was diluted with water and extracted with hot AcOEt. The organic phase was washed with water, dried over Na$_2$SO$_4$ and evaporated in vacuo. The crude reaction mixture was triturated with di-isopropylether/DCM, filtered and the resulting powder was suspended in DCM and treated with HCl/Et$_2$O for 1 h. The solid was filtered and washed with DCM to give 28.1 mg of (E)-3-(4-{(E)-3-[4-(4-benzyl-piperazin-1-ylmethyl)-phenyl]-3-oxo-propenyl}-phenyl)-N-hydroxy-acrylamide as its bis-hydrochloride salt.

Y=27%

LC-MS: Method C, rt=1.41; (ES+) MH$^+$: 482.19

$^1$H NMR (DMSO-d$_6$+TFA 353 K) δ (ppm): 8.13 (m, 2H), 7.86 (m, 2H), 7.83 (d, 1H), 7.68-7.76 (m, 3H), 7.63 (m, 2H), 7.54-7.60 (m, 2H), 7.49 (d, 1H), 7.40-7.46 (m, 3H), 6.64 (d, 1H), 4.24 (s, 2H), 4.18 (s, 2H), 3.08-3.40 (m, 8H).

Example 28

(E)-3-(4-{(E)-3-[4-((2R,6S)-2,6-Dimethyl-morpholin-4-ylmethyl)-phenyl]-3-oxo-propenyl}-phenyl)-N-hydroxy-acrylamide

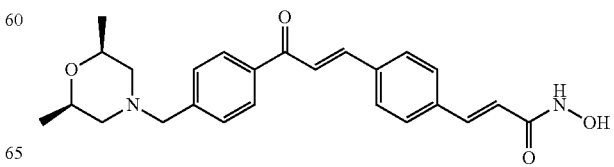

(2S,6R)-2,6-Dimethyl-morpholine (32 mg, 0.277 mmol) was added to a stirred mixture of methanesulfonic acid 4-((E)-3-{4-[(E)-2-(tetrahydro-pyran-2-yloxycarbamoyl)-vinyl]-phenyl}-acryloyl)-benzyl ester (prepared as described in Preparation 5, 112 mg, 0.231 mmol) and TEA (0.064 ml, 0.462 mmol) in DMF (1 ml). The resulting solution was stirred at room temperature overnight. The mixture was diluted with water and extracted with AcOEt. The organic phase was washed with water, dried over $Na_2SO_4$ and evaporated in vacuo. The crude mixture was purified by column chromatography (eluent: DCM/MeOH/$NH_4OH$ 99:1:0.2). The resulting oil was dissolved in DCM and treated with HCl/$Et_2O$ for 1 h. The precipitate was filtered and washed with DCM to give 58.6 mg of (E)-3-(4-{(E)-3-[4-((2R,6S)-2,6-dimethyl-morpholin-4-ylmethyl)-phenyl]-3-oxo-propenyl}-phenyl)-N-hydroxy-acrylamide hydrochloride.

Y=56%

LC-MS: Method C, rt=1.33; (ES+) MH$^+$: 421.19

$^1$H NMR (DMSO-$d_6$+TFA 353 K) δ (ppm): 8.16 (m, 2H), 7.80-7.92 (m, 5H), 7.73 (d, 1H), 7.63 (m, 2H), 7.49 (d, 1H), 6.64 (d, 1H), 4.39 (s, 2H), 3.90-4.19 (m, 2H), 3.25 (d, 2H), 2.68 (dd, 2H), 1.14 (d, 6H).

Example 29

(E)-3-(4-{(E)-3-[4(3R,5S)-3,5-Dimethyl-piperazin-1-ylmethyl)-phenyl]-3-oxo-propenyl}-phenyl)-N-hydroxy-acrylamide

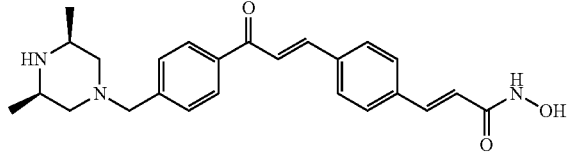

The product was obtained starting from (E)-3-{4-[(E)-3-(4-chloromethyl-phenyl)-3-oxo-propenyl]-phenyl}-N-(tetrahydro-pyran-2-yloxy)-acrylamide (obtained as described in Preparation 5) and (2S,6R)-2,6-dimethyl-piperazine following the experimental procedure described for Example 28. The title compound was obtained as its bis-hydrochloride salt.

LC-MS: Method C, rt=1.16 (ES+) MH$^+$: 420.25

$^1$H NMR (DMSO-$d_6$+TFA 353 K) δ (ppm): 8.12 (m, 2H), 7.86 (m, 2H), 7.84 (d, 1H), 7.72 (d, 1H), 7.60-7.69 (m, 4H), 7.50 (d, 1H), 6.63 (d, 1H), 4.02 (s, 2H), 3.39-3.66 (m, 2H), 3.15-3.24 (m, 2H), 2.57 (dd, 2H), 1.27 (d, 6H).

Example 30

(E)-3-(4-{(E)-3-[4-(4-Acetyl-piperazin-1-ylmethyl)-phenyl]-3-oxo-propenyl}-phenyl)-N-hydroxy-acrylamide

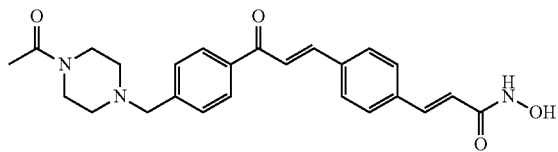

The product was obtained starting from a mixture of methanesulfonic acid 4-((E)-3-{4-[(E)-2-(tetrahydro-pyran-2-yloxycarbamoyl)-vinyl]-phenyl}-acryloyl)-benzyl ester and (E)-3-{4-[(E)-3-(4-chloromethyl-phenyl)-3-oxo-propenyl]-phenyl}-N-(tetrahydro-pyran-2-yloxy)-acrylamide (both obtained as described in Preparation 5) and 1-piperazin-1-yl-ethanone, following the experimental procedure described for Example 28. The title compound was obtained as its hydrochloride salt.

LC-MS: Method C, rt=1.19 (ES+) MH$^+$: 434.19

$^1$H NMR (DMSO-$d_6$+TFA 353 K) δ (ppm): 8.17 (m, 2H), 7.68-7.96 (m, 6H), 7.64 (m, 2H), 7.49 (d, 1H), 6.64 (d, 1H), 4.42 (s, 2H), 3.62-3.89 (m, 4H), 3.04-3.32 (m, 4H), 2.04 (s, 3H).

Example 31

(E)-3-(4-{(E)-3-[4(3R,5S)-4-Acetyl-3,5-dimethyl-piperazin-1-ylmethyl)-phenyl]-3-oxo-propenyl}-phenyl)-N-hydroxy-acrylamide

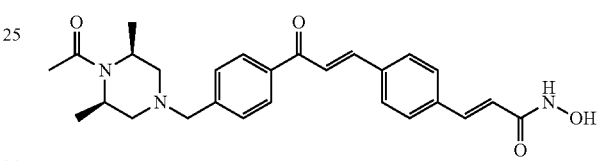

The product was obtained starting from a mixture of methanesulfonic acid 4-((E)-3-{4-[(E)-2-(tetrahydro-pyran-2-yloxycarbamoyl)-vinyl]-phenyl}-acryloyl)-benzyl ester and (E)-3-{4-[(E)-3-(4-chloromethyl-phenyl)-3-oxo-propenyl]-phenyl}-N-(tetrahydro-pyran-2-yloxy)-acrylamide (both obtained as described in Preparation 5) and 1-((2R,6S)-2,6-dimethyl-piperazin-1-yl)-ethanone (obtained as described in Preparation 6), following the experimental procedure described for Example 28. The title compound was obtained as its hydrochloride salt.

LC-MS: Method C, rt=1.28 (ES+) MH$^+$: 462.21

$^1$H NMR (DMSO-$d_6$+TFA 353 K) δ (ppm): 8.14 (m, 2H), 7.68-7.96 (m, 6H), 7.63 (d, 2H), 7.49 (d, 1H), 6.64 (d, 1H), 4.37-4.54 (m, 2H), 4.22 (bs, 2H), 3.10 (d, 2H), 2.86 (bs, 2H), 2.04 (s, 3H), 1.38 (d, 6H).

Example 32

(E)-3-(4-{(E)-3-[4-(4-Ethyl-piperazin-1-ylmethyl)-phenyl]-3-oxo-propenyl}-phenyl)-N-hydroxy-acrylamide

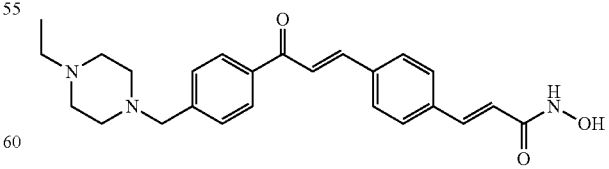

The product was obtained starting from methanesulfonic acid 4-((E)-3-{4-[(E)-2-(tetrahydro-pyran-2-yloxycarbamoyl)-vinyl]-phenyl}-acryloyl)-benzyl ester (obtained as described in Preparation 5) and 1-ethyl-piperazine following the experimental procedure described for Example 28. The title compound was purified by preparative LC-MS and was obtained as its bis-trifluoroacetate salt.

LC-MS: Method C, rt=1.18 (ES+) MH⁺: 420.25

¹H NMR (DMSO-d₆) δ (ppm): 10.79 (bs, 1H), 9.20 (bs, 1H), 8.16 (m, 2H), 7.97 (d, 1H), 7.93 (m, 2H), 7.75 (d, 1H), 7.66 (m, 2H), 7.55 (m, 2H), 7.50 (d, 1 H), 6.56 (d, 1H), 3.77 (s, 2H), 3.27-3.57 (m, 2H), 3.13 (q, 2H), 3.02 (bs, 4H), 2.44 (bs, 2H), 1.21 (t, 3H).

Example 33

(E)-N-Hydroxy-3-{4-[(E)-3-(3-morpholin-4-ylmethyl-phenyl)-3-oxo-propenyl]-phenyl}-acrylamide

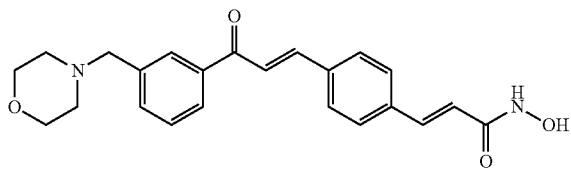

The product was obtained starting from (E)-3-{4-[(E)-3-(3-chloromethyl-phenyl)-3-oxo-propenyl]-phenyl}-N-(tetrahydro-pyran-2-yloxy)-acrylamide (obtained as described in Preparation 7) and morpholine, following the experimental procedure described for the Example 28. The title compound was purified by preparative LC-MS and was obtained as its trifluoroacetate salt.

LC-MS: Method C, rt=1.31 (ES+) MH⁺: 393.08

¹H NMR (DMSO-d₆ 353K+TFA) δ (ppm): 8.19-8.26 (m, 2H), 7.87 (m, 2H), 7.76-7.82 (m, 3H), 7.61-7.74 (m, 3H), 7.50 (d, 1H), 6.64 (d, 1H), 4.47 (s, 2H), 3.71-3.99 (m, 4H), 3.25 (t, 4H).

Example 34

(E)-N-Hydroxy-3-(4-{(E)-3-[3-(4-methyl-piperazin-1-ylmethyl)-phenyl]-3-oxo-propenyl}-phenyl)-acrylamide

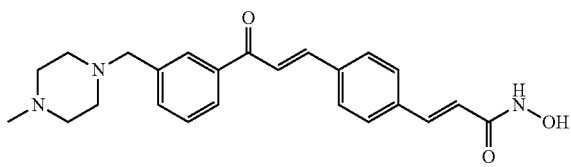

The product was obtained starting from (E)-3-{4-[(E)-3-(3-chloromethyl-phenyl)-3-oxo-propenyl]-phenyl}-N-(tetrahydro-pyran-2-yloxy)-acrylamide (obtained as described in Preparation 7) and N-methylpiperazine, following the experimental procedure described for the Example 28. The title compound was purified by preparative LC-MS and was obtained as its bis-trifluoroacetate salt.

LC-MS: Method C, rt=1.25 (ES+) MH⁺: 406.13

¹H NMR (DMSO-d₆ 353K+TFA) δ (ppm): 8.05-8.12 (m, 2H), 7.73-7.90 (m, 4 H), 7.61-7.72 (m, 3H), 7.58 (t, 1H), 7.50 (d, 1H), 6.63 (d, 1H), 3.86 (s, 2 H), 3.25 (t, 4H), 2.81-2.89 (m, 4H), 2.80 (s, 3H).

Example 35

(E)-N-Hydroxy-3-(4-{(E)-3-[2-(4-methyl-piperazin-1-ylmethyl)-phenyl]-3-oxo-propenyl}-phenyl)-acrylamide

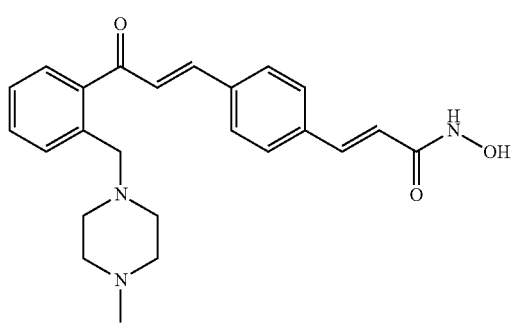

Step A

A mixture of 4-formylcinnamic acid (189 mg, 1.077 mmol), 1-[2-(4-methyl-piperazin-1-ylmethyl)-phenyl]-ethanone (obtained as described in Preparation 11, 250 mg, 1.077 mmol) and 1.7 M KOH (1.26 ml) in EtOH (5 ml) and H₂O (5 ml) was stirred at room temperature overnight and then acidified with 10% HCl. The resulting precipitate was filtered to give 350 mg of (E)-3-(4-{(E)-3-[2-(4-methyl-piperazin-1-ylmethyl)-phenyl]-3-oxo-propenyl}-phenyl)-acrylic acid bis-hydrochloride.

Y=70%

Step B

A mixture of (E)-3-(4-{(E)-3-[2-(4-methyl-piperazin-1-ylmethyl)-phenyl]-3-oxo-propenyl}-phenyl)-acrylic acid bis-hydrochloride (350 mg, 0.756 mmol), HOBT (204 mg, 1.51 mmol), EDC (288 mg, 1.51 mmol), TEA (0.210 ml, 1.51 mmol) and NH₂OTHP (106 mg, 0.907 mmol) in DMF (8 ml) was stirred overnight at room temperature and then partitioned between water and AcOEt. The phases were separated and the aqueous layer was brought to basic conditions with NH₄OH and extracted with DCM. The collected organic extracts were dried over Na₂SO₄ and evaporated in vacuo. The crude mixture was purified by silica gel chromatography (eluent: DCM/MeOH/NH₄OH 95:5:0.2) and the resulting product was dissolved in DCM and treated with HCl/Et₂O for 1 h. The hygroscopic precipitate was filtered and freeze dried to give 229 mg of (E)-N-Hydroxy-3-(4-{(E)-3-[2-(4-methyl-piperazin-1-ylmethyl)-phenyl]-3-oxo-propenyl}-phenyl)-acrylamide as its bis-hydrochloride salt.

Y=63%

LC-MS: Method F, rt=1.14; (ES+) MH⁺: 406.25

¹H NMR (DMSO-d₆ 353K+TFA) δ (ppm): 7.77 (m, 2H), 7.61 (m, 2H), 7.47-7.59 (m, 5H), 7.43 (d, 1H), 7.33 (d, 1H), 6.63 (d, 1H), 3.91 (s, 2H), 3.08-3.25 (m, 4 H), 2.79-2.93 (m, 4H), 2.71 (s, 3H).

Example 36

(E)-N-Hydroxy-3-(5-{(E)-3-[2-(4-methyl-piperazin-1-yl)-phenyl]-3-oxo-propenyl}-pyridin-2-yl)-acrylamide

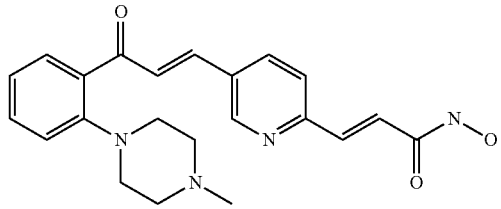

Step A

A mixture of (E)-3-(5-formyl-pyridin-2-yl)-acrylic acid tert-butyl ester (described in Example 11 STEP A-D, 250 mg, 1.07 mmol), KOH (90 mg, 1.61 mmol) and 1-[2-(4-methyl-piperazin-1-yl)-phenyl]-ethanone (described in Example 1 STEP A-B, 233 mg, 1.07 mmol) in EtOH (10 ml) was stirred at room temperature overnight. The mixture was acidified with 10% HCl and the solvent was removed in vacuo. The crude reaction mixture (700 mg) was used in the next step without any further purification.

Step B (E)-3-(5-{(E)-3-[2-(4-Methyl-piperazin-1-yl)-phenyl]-3-oxo-propenyl}-pyridin-2-yl)-acrylic acid hydrochloride (crude mixture from Step A, 400 mg) was suspended in DMF (10 ml). HOBT (240 mg, 1.78 mmol), EDC (340 mg, 1.78 mmol), TEA (0.371 ml, 2.67 mmol) and NH$_2$OTHP (125 mg, 1.06 mmol) were added to the resulting slurry. The mixture was stirred overnight at room temperature and then partitioned between water and AcOEt. The organic phase was washed with water, dried over Na$_2$SO$_4$ and evaporated in vacuo. The crude reaction mixture was purified by column chromatography (DCM/MeOH/NH$_4$OH 95:5:0.2). The collected fractions were evaporated and the resulting product was dissolved in DCM and treated with HCl/Et$_2$O for 1 h. The precipitate was filtered off and purified by preparative LC-MS to give 23.7 mg of (E)-N-hydroxy-3-(5-{(E)-3-[2-(4-methyl-piperazin-1-yl)-phenyl]-3-oxo-propenyl}-pyridin-2-yl)-acrylamide as its trifluoroacetate salt.

LC-MS: Method C, rt=1.26; (ES+) MH$^+$: 393.12

$^1$H NMR (DMSO-d$_6$) δ (ppm): 9.81 (bs, 1H), 8.97 (d, 1H), 8.29 (dd, 1H), 7.67 (d, 1H), 7.62 (d, 1H), 7.48-7.60 (m, 4H), 7.30 (d, 1H), 7.21 (td, 1H), 7.00 (d, 1H), 3.47 (d, 2H), 3.22-3.40 (m, 2H), 3.02-3.21 (m, 2H), 2.82-3.02 (m, 2H), 2.75 (s, 3H).

Example 37

(E)-N-Hydroxy-3-(5-{(E)-3-[3-(4-methyl-piperazin-1-yl)-phenyl]-3-oxo-propenyl}-pyridin-2-yl)-acrylamide

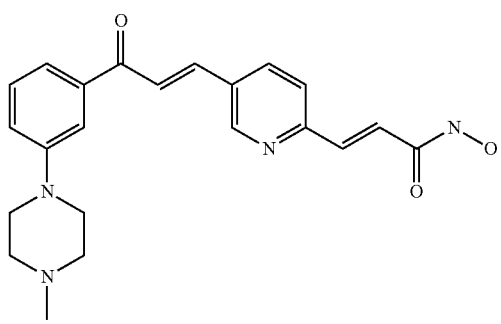

Step A

A mixture of (E)-3-(5-formyl-pyridin-2-yl)-acrylic acid tert-butyl ester (described in Example 11 STEP A-D, 190 mg, 0.81 mmol), KOH 1.7 M (0.716 ml, 1.22 mmol) and 1-[3-(4-methyl-piperazin-1-yl)-phenyl]-ethanone (177 mg, 0.812 mmol) in EtOH (8 ml) was stirred at 0° C. for 4 h. The resulting slurry was partitioned between water and AcOEt and the organic phase was dried over Na$_2$SO$_4$ and evaporated in vacuo. The crude reaction mixture was purified by column chromatography (eluent: DCM/MeOH/NH$_4$OH 98:2:0.2). The collected fractions were evaporated and the resulting powder was dissolved in DCM (10 ml) and TFA (1 ml). The solution was stirred at room temperature for 72 h. The solvent was then removed and the residue was triturated in Et$_2$O to give 164 mg (E)-3-(5-{(E)-3-[3-(4-methyl-piperazin-1-yl)-phenyl]-3-oxo-propenyl}-pyridin-2-yl)-acrylic acid as its bis-trifluoroacetate salt.

Y=32%

Step B (E)-3-(5-{(E)-3-[3-(4-Methyl-piperazin-1-yl)-phenyl]-3-oxo-propenyl}-pyridin-2-yl)-acrylic acid bis-trifluoroacetate (164 mg, 0.27 mmol) was dissolved in DMF (7 ml). HOBT (90 mg, 0.668 mmol), EDC (127 mg, 0.668 mmol), TEA (0.139 ml, 1 mmol) and NH$_2$OTHP (47 mg, 0.400 mmol) were added to the resulting solution. The mixture was stirred overnight at room temperature and then partitioned between water and AcOEt. Then the organic phase was dried over Na$_2$SO$_4$, evaporated in vacuo and the crude product was purified by column chromatography (eluent: DCM/MeOH/NH$_4$OH 98:2:0.2). The collected fractions were evaporated and the resulting product was dissolved in DCM and treated with HCl/Et$_2$O for 1 h. The precipitate was filtered off and purified by preparative LC-MS to give 23.6 mg of (E)-N-hydroxy-3-(5-{(E)-3-[3-(4-methyl-piperazin-1-yl)-phenyl]-3-oxo-propenyl}-pyridin-2-yl)-acrylamide as its bis-trifluoroacetate salt.

Y=14%

LC-MS: Method C, rt=1.17; (ES+) MH$^+$: 393.25

$^1$H NMR (DMSO-d$_6$) δ (ppm): 10.96 (bs, 1H), 9.66 (bs, 1H), 9.05 (d, 1H), 8.39 (dd, 1H), 8.06 (d, 1H), 7.78 (d, 1H), 7.62-7.73 (m, 3H), 7.53 (d, 1H), 7.48 (t, 1 H), 7.34 (dd, 1H), 7.01 (d, 1H), 3.95-4.05 (m, 2H), 3.52-3.62 (m, 2H), 2.96-3.29 (m, 4H), 2.89 (dd, 3H).

Example 38

(E)-3-(5-{(E)-3-[4-(4-Benzyl-piperazin-1-yl)-phenyl]-3-oxo-propenyl}-pyridin-2-yl)-N-hydroxy-acrylamide

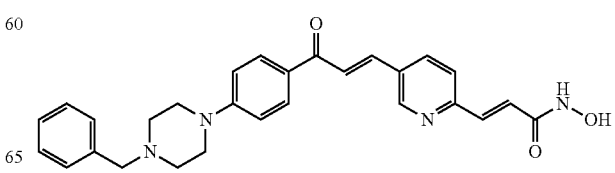

Step A

A mixture of 1-(4-piperazin-1-yl-phenyl)-ethanone (500 mg, 2.45 mmol), benzaldehyde (312 mg, 2.94 mmol) and NaBH(OAc)$_3$ (778 mg, 3.67 mmol) in AcOEt (15 ml) was stirred at room temperature overnight. The resulting solution was partitioned between water and DCM and the organic phase was dried over Na$_2$SO$_4$ and evaporated in vacuo. The crude product was purified by silica gel chromatography (eluent: DCM/MeOH/NH$_4$OH 95:5:0.2) to give 390 mg of 1-[4-(4-benzyl-piperazin-1-yl)-phenyl]-ethanone.

Y=54%

Step B

A mixture of 1-[4-(4-benzyl-piperazin-1-yl)-phenyl]-ethanone (319 mg, 1.085 mmol), (E)-3-(5-formyl-pyridin-2-yl)-acrylic acid tert-butyl ester (described in Example 11 STEP A-D, 253 mg, 1.08 mmol) and KOH 1.7 M (0.638 ml) in EtOH (10 ml) was stirred at 0° C. overnight. The resulting precipitate was filtered washing with hot EtOH and the powder was dissolved in DCM (10 ml) and treated with TFA (2 ml) for 6 h. The solvent was then removed in vacuo to give 388 mg of (E)-3-(5-{(E)-3-[4-(4-benzyl-piperazin-1-yl)-phenyl]-3-oxo-propenyl}-pyridin-2-yl)-acrylic acid as its bis-trifluoroacetate salt.

Y=53%

Step C (E)-3-(5-{(E)-3-[4-(4-Benzyl-piperazin-1-yl)-phenyl]-3-oxo-propenyl}-pyridin-2-yl)-acrylic acid bis-trifluoroacetate (388 mg, 0.569 mmol) was dissolved in DMF (6 ml). HOBT (154 mg, 1.14 mmol), EDC (217.7 mg, 1.14 mmol), TEA (0.238 ml, 1.74 mmol) and NH$_2$OTHP (80 mg, 0.684 mmol) were added to the resulting solution. The mixture was stirred at room temperature overnight and then partitioned between water and AcOEt. The organic phase was washed with water, dried over Na$_2$SO$_4$ and evaporated in vacuo. The crude reaction mixture was purified by column chromatography (eluent: DCM/MeOH/NH$_4$OH 98:2:0.2). The collected fractions were evaporated and the resulting product was dissolved in DCM and treated with HCl/Et$_2$O for 1 h. The precipitate was filtered off and washed with DCM to give 95.4 mg of (E)-3-(5-{(E)-3-[4-(4-benzyl-piperazin-1-yl)-phenyl]-3-oxo-propenyl}-pyridin-2-yl)-N-hydroxy-acrylamide as its bis-hydrochloride salt.

Y=31%

LC-MS: Method E, rt=2.00; (ES+) MH$^+$: 469.33

$^1$H NMR (DMSO-d$_6$) δ (ppm): 11.46 (bs, 1H), 9.05 (d, 1H), 8.44 (dd, 1H), 8.12 (d, 2H), 8.09 (d, 1H), 7.62-7.80 (m, 4H), 7.53 (d, 1H), 7.44-7.50 (m, 3H), 7.09 (d, 2H), 7.03 (d, 1H), 4.38 (d, 2H), 4.08-4.21 (m, 2H), 3.30-3.51 (m, 4 H), 2.99-3.24 (m, 2H).

Example 39

(E)-N-Hydroxy-3-(5-{(E)-3-oxo-3-[4-((3R,5S)-3,4,5-trimethyl-piperazin-1-yl)-phenyl]-propenyl}-pyridin-2-yl)-acrylamide

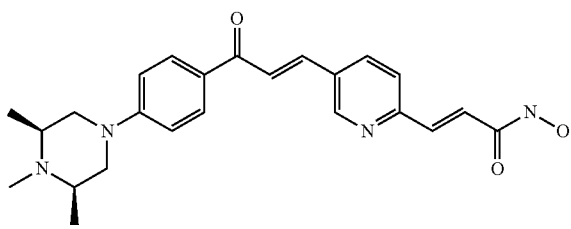

The title compound was obtained starting from 1-[4-((3R,5S)-3,4,5-trimethyl-piperazin-1-yl)-phenyl]-ethanone (prepared as described in Preparation 3) and (E)-3-(5-formyl-pyridin-2-yl)-acrylic acid tert-butyl ester (described in Example 11 STEP A-D), following procedure described for Example 38 (STEP B-C). The title compound was purified by preparative LC-MS and was obtained as its bis-trifluoroacetate salt.

LC-MS: Method C, rt=1.61; (ES+) MH$^+$: 421.23

$^1$H NMR (DMSO-d$_6$) δ (ppm): 10.95 (bs, 1H), 9.26 (bs, 1H), 9.02 (d, 1H), 8.38 (dd, 1H), 8.03-8.18 (m, 3H), 7.72 (d, 1H), 7.68 (d, 1H), 7.53 (d, 1H), 7.16 (d, 2 H), 7.00 (d, 1H), 4.24 (d, 2H), 3.51 (bs, 2H), 2.96 (dd, 2H), 2.88 (d, 3H), 1.39 (d, 6H).

Example 40

(E)-N-Hydroxy-3-{5-[(E)-3-(4-morpholin-4-ylmethyl-phenyl)-3-oxo-propenyl]-pyridin-2-yl}-acrylamide

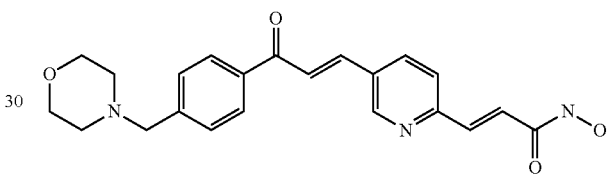

The title compound was obtained starting from 1-(4-morpholin-4-ylmethyl-phenyl)-ethanone (described in Example 7 STEP A and B) and (E)-3-(5-formyl-pyridin-2-yl)-acrylic acid tert-butyl ester (described in Example 11 STEP A-D), following the procedure described for Example 38 (STEP B-C). The title compound was obtained as its bis-hydrochloride salt.

LC-MS: Method C, rt=1.06; (ES+) MH$^+$: 394.26

$^1$H NMR (DMSO-d$_6$) δ (ppm): 9.07 (d, 1H), 8.44 (dd, 1H), 8.25 (d, 2H), 8.13 (d, 1 H), 7.86 (d, 2H), 7.81 (d, 1H), 7.72 (d, 1H), 7.53 (d, 1H), 7.03 (d, 1H), 4.44 (m, 2H), 3.75-4.01 (m, 4H), 3.02-3.34 (m, 4H).

Example 41

(E)-3-(5-{(E)-3-[4-(4-Ethyl-piperazin-1-yl)-phenyl]-3-oxo-propenyl}-pyridin-2-yl)-N-hydroxy-acrylamide

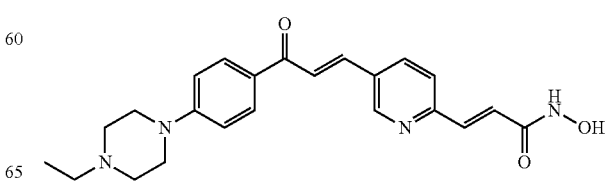

Step A

A mixture of 1-(4-piperazin-1-yl-phenyl)-ethanone (500 mg, 2.45 mmol), CH$_3$CHO (161 mg, 3.67 mmol) and NaBH(OAc)$_3$ (778 mg, 3.67 mmol) in DCM (15 ml) was stirred at room temperature overnight. The resulting solution was partitioned between water and DCM and the organic phase was extracted with 1 M HCl. The aqueous layer was brought to basic conditions with NH$_4$OH, extracted with AcOEt and then the organic phase was dried over Na$_2$SO$_4$ and evaporated in vacuo to give 250 mg of 1-[4-(4-ethyl-piperazin-1-yl)-phenyl]-ethanone.

Y=44%

Step B

A mixture of 1-[4-(4-ethyl-piperazin-1-yl)-phenyl]-ethanone (250 mg, 1.073 mmol), (E)-3-(5-formyl-pyridin-2-yl)-acrylic acid tert-butyl ester (described in Example 11 STEP A-D, 250 mg, 1.073 mmol) and KOH 1.7 M (1.26 ml) in EtOH (10 ml) was stirred at 0° C. for 2 h and then at 4° C. overnight. The solution was then acidified with HCl/Et$_2$O and the solvent was removed in vacuo. The crude reaction mixture was dissolved in DCM (10 ml) and TFA (2 ml) and the solution was stirred at room temperature for 6 h. The solvent was removed under vacuo and the resulting solid was triturated with EtOH to give 391 mg of (E)-3-(5-{(E)-3-[4-(4-ethyl-piperazin-1-yl)-phenyl]-3-oxo-propenyl}-pyridin-2-yl)-acrylic acid bis-trifluoroacetate as a yellow powder.

Y=59%

Step C (E)-3-(5-{(E)-3-[4-(4-Ethyl-piperazin-1-yl)-phenyl]-3-oxo-propenyl}-pyridin-2-yl)-acrylic acid bis-trifluoroacetate (391 mg, 0.631 mmol) was dissolved in DMF (7 ml) and TEA (0.263 ml, 1.89 mmol). HOBT (170 mg, 1.26 mmol), EDC (240 mg, 1.26 mmol), and NH$_2$OTHP (89 mg, 0.758 mmol) were added to the resulting solution. The mixture was stirred at room temperature overnight and then partitioned between water and AcOEt. The organic phase was washed with water, dried over Na$_2$SO$_4$ and evaporated in vacuo. The crude reaction mixture was purified by column chromatography (eluent: DCM/MeOH/NH$_4$OH 99:1:0.2). The collected fractions were evaporated and the resulting product was dissolved in DCM and treated with HCl/Et$_2$O for 1 h. The precipitate was filtered off, washed with DCM and Et$_2$O to give 112 mg of (E)-3-(5-{(E)-3-[4-(4-ethyl-piperazin-1-yl)-phenyl]-3-oxo-propenyl}-pyridin-2-yl)-N-hydroxy-acrylamide bis-hydrochloride.

Y=37%

LC-MS: Method C, rt=1.09; (ES+) MH$^+$: 407.32

$^1$H NMR (DMSO-d$_6$+TFA) δ (ppm): 11.31 (bs, 1H), 9.09 (d, 1H), 8.52 (dd, 1H), 8.13 (m, 2H), 8.14 (d, 1H), 7.80 (d, 1H), 7.72 (d, 1H), 7.56 (d, 1H), 7.12 (m, 2 H), 7.07 (d, 1H), 4.13 (d, 2H), 3.55 (d, 2H), 3.26-3.46 (m, 2H), 2.96-3.23 (m, 4H), 1.30 (t, 3H).

Example 42

(E)-3-(5-{(E)-3-[4-(4-Acetyl-piperazin-1-yl)-phenyl]-3-oxo-propenyl}-pyridin-2-yl)-N-hydroxy-acrylamide

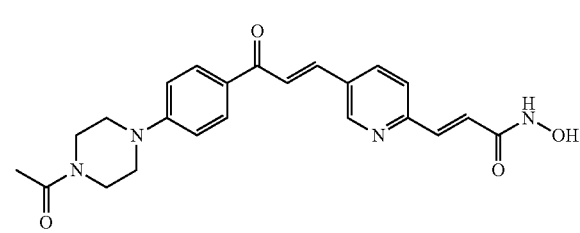

The title compound was obtained starting from 1-[4-(4-acetyl-piperazin-1-yl)-phenyl]-ethanone (prepared following the procedure described in Example 16 STEP A) and (E)-3-(5-formyl-pyridin-2-yl)-acrylic acid tert-butyl ester (described in Example 11 STEP A-D), following the procedure described for Example 38 (STEP B-C). The title compound was purified by preparative LC-MS and was obtained as its trifluoroacetate salt.

LC-MS: Method C, rt=1.32; (ES+) MH$^+$: 421.19

$^1$H NMR (DMSO-d$_6$) δ (ppm): 9.01 (d, 1H), 8.37 (dd, 1H), 8.09 (m, 2H), 8.08 (d, 1H), 7.69 (d, 1H), 7.67 (d, 1H), 7.52 (d, 1H), 7.04 (m, 2H), 7.00 (d, 1H), 3.57-3.67 (m, 4H), 3.33-3.49 (m, 4H), 2.05 (s, 3H).

Example 43

(E)-N-Hydroxy-3-(5-{(E)-3-oxo-3-[3-((3R,5S)-3,4,5-trimethyl-piperazin-1-yl)-phenyl]-propenyl}-pyridin-2-yl)-acrylamide

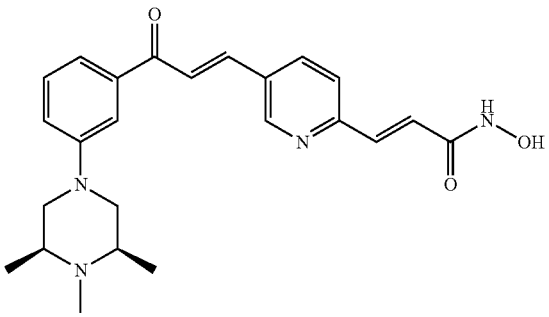

Step A

A mixture of (E)-3-(5-formyl-pyridin-2-yl)-acrylic acid tert-butyl ester (described in Example 11 STEP A-D, 168 mg, 0.718 mmol), 1.7 M KOH (0.674 ml) and 1-[3-((3R,5S)-3,4,5-trimethyl-piperazin-1-yl)-phenyl]-ethanone (described in Preparation 8, 188 mg, 0.764 mmol) in EtOH (7 ml) was stirred at 0° C. for 6 h. The resulting precipitate was filtered off and dissolved in DCM (5 ml) and TFA (1 ml). The mixture was stirred at room temperature for 4 h and then the solvent was removed in vacuo to give 282 mg of (E)-3-(5-{(E)-3-oxo-3-[3-((3R,5S)-3,4,5-trimethyl-piperazin-1-yl)-phenyl]-propenyl}-pyridin-2-yl)-acrylic acid as its bis-trifluoroacetate salt.

Y=58%

Step B

A mixture of (E)-3-(5-{(E)-3-oxo-3-[3-((3R,5S)-3,4,5-trimethyl-piperazin-1-yl)-phenyl]-propenyl}-pyridin-2-yl)-acrylic acid bis-trifluoroacetate (282 mg, 0.445 mmol), HOBT (120 mg, 0.890 mmol), EDC (170 mg, 0.890 mmol), TEA (0.186 ml, 1.33 mmol) and NH$_2$OTHP (62 mg, 0.534 mmol) in DMF (5 ml), was stirred at room temperature overnight and then partitioned between water and AcOEt. The organic extract was dried over Na$_2$SO$_4$, evaporated in vacuo and the crude was purified by column chromatography (eluent: DCM/MeOH/NH$_4$OH 96:4:0.2). The collected fractions were evaporated and the resulting product was dissolved in DCM and treated with HCl/Et$_2$O for 1 h. The precipitate was filtered off and washed with DCM to give 26.6 mg of (E)-N-hydroxy-3-(5-{(E)-3-oxo-3-[3-((3R,5S)-3,4,5-trimethyl-piperazin-1-yl)-phenyl]-propenyl}-pyridin-2-yl)-acrylamide as its bis-hydrochloride salt.

Y=12%

LC-MS: Method C, rt=1.25; (ES+) MH$^+$: 421.2

$^1$H NMR (DMSO-d$_6$) δ (ppm): 10.84 (bs, 2H), 9.08 (d, 1H), 8.46 (dd, 1H), 8.09 (d, 1H), 7.78 (d, 1H), 7.63-7.77 (m, 3H), 7.54 (d, 1H), 7.47 (dd, 1H), 7.36 (dd, 1H), 7.04 (d, 1H), 3.97-4.12 (m, 2H), 3.27-3.49 (m, 2H), 3.06 (dd, 2H), 2.82 (d, 3H), 1.44 (d, 6H).

Example 44

(E)-N-Hydroxy-3-(5-{(E)-3-[4-(1-methyl-piperidin-4-ylmethyl)-phenyl]-3-oxo-propenyl}-pyridin-2-yl)-acrylamide

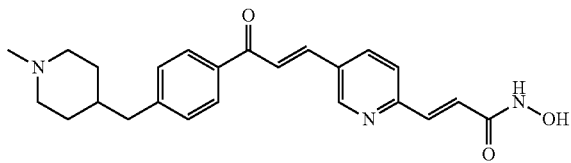

The product was obtained starting from (E)-3-(5-formyl-pyridin-2-yl)-acrylic acid tert-butyl ester (described in Example 11 STEP A-D) and 1-[4-(1-methyl-piperidin-4-ylmethyl)-phenyl]-ethanone (prepared as described in Preparation 2) following the experimental procedure described for Example 43.

The title compound was obtained as its bis-hydrochloric salt.

LC-MS: Method C, rt=1.24; (ES+) MH$^+$: 406.18

$^1$H NMR (DMSO-d$_6$+TFA 353 K) δ (ppm): 9.91 (s, 1H), 8.99 (d, 1H), 8.30 (dd, 1H), 8.07 (m, 2H), 7.95 (d, 1H), 7.73 (d, 1H), 7.65 (d, 1H), 7.51 (d, 1H), 7.40 (m, 2H), 7.05 (d, 1H), 3.39 (d, 2H), 2.82-2.96 (m, 2H), 2.71 (s, 3H), 2.70 (d, 2H), 1.74-1.95 (m, 3H), 1.46-1.67 (m, 2H).

Example 45

(E)-N-Hydroxy-3-{5-[(E)-3-oxo-3-(4-piperazin-1-yl-phenyl)-propenyl]-pyridin-2-yl}-acrylamide

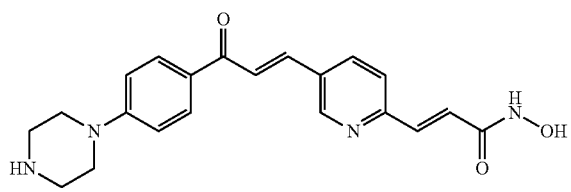

Step A

A mixture of (E)-3-(5-formyl-pyridin-2-yl)-acrylic acid tert-butyl ester (described in Example 11 STEP A-D, 250 mg, 1.07 mmol) and TFA (1 ml) in DCM (4 ml) was stirred at room temperature for 6 h. The solvent was then removed in vacuo and the solid was triturated with Et$_2$O to give 272 mg of (E)-3-(5-formyl-pyridin-2-yl)-acrylic acid as its trifluoroacetate salt.

Y=87%

Step B

A mixture of (E)-3-(5-formyl-pyridin-2-yl)-acrylic acid trifluoroacetate (272 mg, 0.93 mmol), 4-(4-acetyl-phenyl)-piperazine-1-carboxylic acid tert-butyl ester (obtained as described in Preparation 9, 283 mg, 0.93 mmol) and 1.7 M KOH (0.820 ml) in EtOH (10 ml) was stirred at 0° C. for 8 h and then at room temperature for 6 days. The mixture was acidified with 10% HCl until reaching a pH value of 3 and the resulting precipitate was filtered to give 184 mg of 4-(4-{(E)-3-[6-((E)-2-carboxy-vinyl)-pyridin-3-yl]-acryloyl}-phenyl)-piperazine-1-carboxylic acid tert-butyl ester hydrochloride.

Y=40%

Step C 4-(4-{(E)-3-[6-((E)-2-carboxy-vinyl)-pyridin-3-yl]-acryloyl}-phenyl)-piperazine-1-carboxylic acid tert-butyl ester hydrochloride (184 mg, 0.363 mmol) was dissolved in DMF (5 ml), THF (5 ml) and TEA (0.190 ml, 1.47 mmol). Then EDC (140 mg, 0.736 mmol), HOBT (99 mg, 0.736 mmol) and NH$_2$OTHP (51.6 mg, 0.441 mmol) were added to the resulting solution. The mixture was stirred at room temperature overnight and then partitioned between water and AcOEt. The organic phase was dried over Na$_2$SO$_4$ and evaporated in vacuo. The crude reaction mixture was purified by column chromatography (eluent: DCM/MeOH/NH$_4$OH 98:2:0.2) and the resulting compound was dissolved in DCM and treated with HCl/Et$_2$O for 1 h. The precipitate was filtered off and washed with DCM. The hygroscopic powder was dissolved in water and freeze dried to give 53 mg of (E)-N-hydroxy-3-{5-[(E)-3-oxo-3-(4-piperazin-1-yl-phenyl)-propenyl]-pyridin-2-yl}-acrylamide as its bis-hydrochloride salt.

Y=32%

LC-MS: Method C, rt=1.08; (ES+) MH$^+$: 379.18

$^1$H NMR (DMSO-d$_6$+TFA 353 K) δ (ppm): 9.20 (bs, 2H), 8.98 (d, 1H), 8.29 (dd, 1H), 8.07 (m, 2H), 7.95 (d, 1H), 7.68 (d, 1H), 7.65 (d, 1H), 7.51 (d, 1H), 7.08 (m, 2H), 7.05 (d, 1H), 3.59-3.70 (m, 4H), 3.16-3.33 (m, 4H).

Example 46

(E)-3-(4-{(E)-3-[5-Chloro-2-(4-methyl-piperazin-1-yl)-phenyl]-3-oxo-propenyl}-phenyl)-N-hydroxy-acrylamide

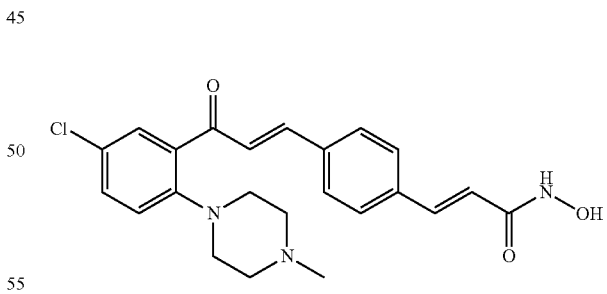

Step A

A mixture of 4-formylcinnamic acid (397 mg, 2.25 mmol), 1-[5-chloro-2-(4-methyl-piperazin-1-yl)-phenyl]-ethanone (obtained as described in Preparation 10, 570 mg, 2.25 mmol) and 1.7 M KOH (2.66 ml) in EtOH (25 ml) was stirred at 0° C. for 3 h and then acidified with 10% HCl. The solution was concentrated until formation of a yellow precipitate. The solid was filtered to give 823 mg of (E)-3-(4-{(E)-3-[5-chloro-2-(4-methyl-piperazin-1-yl)-phenyl]-3-oxo-propenyl}-phenyl)-acrylic acid hydrochloride.

Y=82%

Step B

A mixture of (E)-3-(4-{(E)-3-[5-chloro-2-(4-methyl-piperazin-1-yl)-phenyl]-3-oxo-propenyl}-phenyl)-acrylic acid hydrochloride (250 mg, 0.56 mmol), HOBT (139 mg, 1.03 mmol), EDC (196 mg, 1.03 mmol), TEA (0.568 ml, 4.08 mmol) and NH$_2$OTHP (89 mg, 0.765 mmol) in DCM (5 ml) was stirred overnight at room temperature. The solvent was evaporated and the residue was partitioned between water and AcOEt. The phases were separated and the aqueous layer was brought to basic conditions with NH$_4$OH and extracted with DCM. The collected organic extract were dried over Na$_2$SO$_4$ and evaporated in vacuo. The crude mixture was purified by silica gel chromatography (eluent: DCM/MeOH/NH$_4$OH 97:3:0.1) and the resulting product was dissolved in DCM and treated with HCl/Et$_2$O for 2.5 h. The precipitate was filtered and triturated with isopropanol and di-isopropylether to give 61 mg of (E)-3-(4-{(E)-3-[5-chloro-2-(4-methyl-piperazin-1-yl)-phenyl]-3-oxo-propenyl}-phenyl)-N-hydroxy-acrylamide hydrochloride.

Y=23%

LC-MS: Method F, rt=1.61; (ES+) MH$^+$: 426.17

1H NMR (DMSO-d$_6$) δ (ppm): 10.83 (bs, 1H), 7.85 (m, 2H), 7.64 (m, 2H), 7.42-7.62 (m, 5H), 7.31 (d, 1H), 6.57 (d, 1H), 3.43 (d, 2H), 3.08-3.35 (m, 4H), 2.78-3.01 (m, 2H), 2.67 (d, 3H).

Example 47

(E)-N-Hydroxy-3-(5-{(E)-3-[2-(4-methyl-piperazin-1-ylmethyl)-phenyl]-3-oxo-propenyl}-pyridin-2-yl)-acrylamide

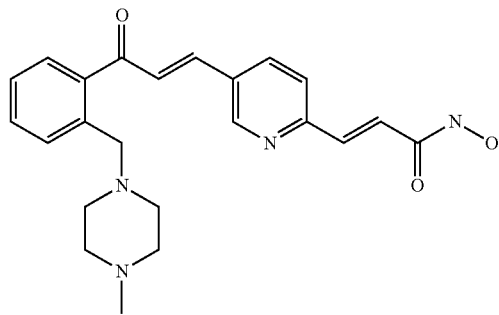

Step A

A mixture of 1-[2-(4-methyl-piperazin-1-ylmethyl)-phenyl]-ethanone (obtained as described in Preparation 11, 250 mg, 1.07 mmol), (E)-3-(5-formyl-pyridin-2-yl)-acrylic acid tert-butyl ester (described in Example 11 STEP A-D, 251 mg, 1.07 mmol) and 1.7 M KOH (0.633 ml) in EtOH (10 ml) was stirred at 4° C. overnight. The resulting solution was diluted with water and extracted with AcOEt. The organic phase was dried over Na$_2$SO$_4$ and evaporated in vacuo. The crude reaction mixture was purified by column chromatography (eluent: DCM/MeOH/NH$_4$OH 95:5:0.2) and the resulting product was dissolved in DCM (10 ml) and TFA (2 ml) and stirred at room temperature for 4 h. The solvent was evaporated to give 558 mg of (E)-3-(5-{(E)-3-[2-(4-methyl-piperazin-1-ylmethyl)-phenyl]-3-oxo-propenyl}-pyridin-2-yl)-acrylic acid as its tris-trifluoroacetate salt.

Y=71%

Step B

A mixture of (E)-3-(5-{(E)-3-[2-(4-methyl-piperazin-1-ylmethyl)-phenyl]-3-oxo-propenyl}-pyridin-2-yl)-acrylic acid tris-trifluoroacetate (558 mg, 0.76 mmol), HOBT (205 mg, 1.52 mmol), EDC (290 mg, 1.52 mmol), TEA (0.423 ml, 3.04 mmol) and NH$_2$OTHP (107 mg, 0.913 mmol) in DMF (10 ml) was stirred overnight at room temperature. The solution was diluted with water, brought to basic conditions with NH$_4$OH and extracted with AcOEt and DCM. The collected organic extracts were dried over Na$_2$SO$_4$ and evaporated in vacuo. The crude mixture was purified by silica gel chromatography (eluent: DCM/MeOH/NH$_4$OH 96:4:0.2) and the resulting product was dissolved in DCM and treated with HCl/Et$_2$O for 2 h. The hygroscopic precipitate was filtered and freeze dried to give 130 mg of the title compound. 70 mg were purified by preparative LC-MS to give 35 mg of (E)-N-hydroxy-3-(5-{(E)-3-[2-(4-methyl-piperazin-1-ylmethyl)-phenyl]-3-oxo-propenyl}-pyridin-2-yl)-acrylamide as its formate salt.

LC-MS: Method F, rt=0.93; (ES+) MH$^+$: 407.20

$^1$H NMR (DMSO-d$_6$) δ (ppm): 10.90 (bs, 1H), 8.90 (d, 1H), 8.24 (dd, 1H), 8.15 (s, 1H), 7.63 (d, 1H), 7.50 (d, 1H), 7.33-7.47 (m, 5H), 7.20-7.33 (m, 1H), 6.98 (d, 1H), 3.58 (s, 2H), 2.27 (m, 4H), 2.18 (m, 4H), 2.05 (s, 3H).

Example 48

(E)-N-Hydroxy-3-{5-[(E)-3-oxo-3-(4-piperazin-1-ylmethyl-phenyl)-propenyl]-pyridin-2-yl}-acrylamide

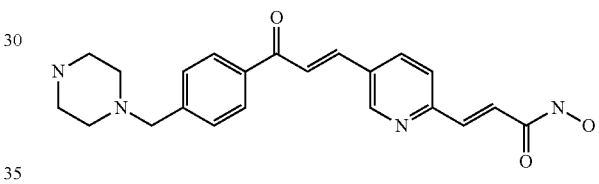

Step A

A mixture of (E)-3-(5-formyl-pyridin-2-yl)-acrylic acid trifluoroacetate (described in Example 45 STEP A, 206 mg, 0.71 mmol), 4-(4-acetyl-benzyl)-piperazine-1-carboxylic acid tert-butyl ester (described in Preparation 12, 368 mg, 1.16 mmol) and 1.7 M KOH (2 ml) in EtOH (12 ml) was stirred at 4° C. overnight. The resulting precipitate was filtered and washed with AcOEt to give 250 mg of 4-(4-{(E)-3-[6-((E)-2-carboxy-vinyl)-pyridin-3-yl]-acryloyl}-benzyl)-piperazine-1-carboxylic acid tert-butyl ester as its potassium salt.

Y=69%

Step B

A mixture of 4-(4-{(E)-3-[6-((E)-2-carboxy-vinyl)-pyridin-3-yl]-acryloyl}-benzyl)-piperazine-1-carboxylic acid tert-butyl ester potassium salt (250 mg, 0.48 mmol), HOBT (130 mg, 0.96 mmol), EDC (184 mg, 0.96 mmol), TEA (0.134 ml, 0.96 mmol) and NH$_2$OTHP (84 mg, 0.72 mmol) in DMF (4 ml) and DCM (4 ml) was stirred at room temperature for 5 h. The solution was diluted with DCM and washed with water and brine. The organic phase was dried over Na$_2$SO$_4$ and evaporated in vacuo. The crude mixture was purified by column chromatography (eluent: DCM/MeOH/NH$_4$OH 95:5:0.1) and the resulting product was dissolved in DCM and treated with HCl/Et$_2$O for 4 h. The resulting precipitate was filtered and purified by preparative LC-MS to give 40 mg of (E)-N-hydroxy-3-{5-[(E)-3-oxo-3-(4-piperazin-1-ylmethyl-phenyl)-propenyl]-pyridin-2-yl}-acrylamide as its formate salt.

Y=19%

LC-MS: Method F, rt=0.91; (ES+) MH$^+$: 393.18

1H NMR (DMSO-d$_6$ 353K) δ (ppm): 8.99 (d, 1H), 8.29 (dd, 1H), 8.18 (s, 1H), 8.08 (m, 2H), 7.87-8.01 (m, 1H), 7.68-7.80 (m, 1H), 7.64 (d, 1H), 7.51 (d, 1 H), 7.51 (m, 2H), 7.05 (d, 1H), 3.58 (s, 2H), 2.75-2.86 (m, 4H), 2.33-2.46 (m, 4H).

Example 49

(E)-3-(5-{(E)-3-[4-(4-Acetyl-piperazin-1-ylmethyl)-phenyl]-3-oxo-propenyl}-pyridin-2-yl)-N-hydroxy-acrylamide

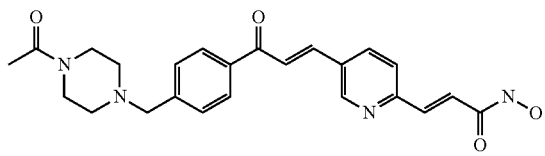

Step A

A mixture of 1-[4-(4-acetyl-benzyl)piperazin-1-yl]-ethanone (prepared following the procedure described in Preparation 12, 500 mg, 1.92 mmol), (E)-3-(5-formyl-pyridin-2-yl)-acrylic acid tert-butyl ester (described in Example 11 STEP A-D, 448 mg, 1.92 mmol) and 1.7 M KOH (1.2 ml) in EtOH (19 ml) was stirred at room temperature for 6 h and then partitioned between water and AcOEt. The organic phase was dried over Na$_2$SO$_4$ and evaporated in vacuo. The crude reaction mixture was purified by column chromatography (eluent: DCM/MeOH/NH$_4$OH 97:3:0.1) and the resulting product was dissolved in DCM (1.5 ml) and TFA (0.560 ml). The solution was stirred at room temperature for 3 h and then the solvent was evaporated to give 300 mg (E)-3-(5-{(E)-3-[4-(4-acetyl-piperazin-1-ylmethyl)-phenyl]-3-oxo-propenyl}-pyridin-2-yl)-acrylic acid as its bis-trifluoroacetate salt (the compound was used without further purification in the next step).

Step B

A mixture of (E)-3-(5-{(E)-3-[4-(4-acetyl-piperazin-1-ylmethyl)-phenyl]-3-oxo-propenyl}-pyridin-2-yl)-acrylic acid bis-trifluoroacetate (300 mg), HOBT (105 mg, 0.78 mmol), EDC (149 mg, 0.78 mmol), TEA (0.271 ml, 1.95 mmol) and NH$_2$OTHP (69 mg, 0.58 mmol) in DMF (2 ml) and DCM (20 ml) was stirred at room temperature overnight. Further NH$_2$OTHP (69 mg, 0.58 mmol) was added and after stirring at room temperature overnight the solution was diluted with DCM and washed with water and brine. The organic phase was dried over Na$_2$SO$_4$ and evaporated in vacuo. The crude mixture was purified by silica gel chromatography (eluent: DCM/MeOH/NH$_4$OH 96:4:0.1) and the resulting product was dissolved in DCM and treated with HCl/Et$_2$O for 3 h. The resulting precipitate was filtered and purified by preparative LC-MS to give 9.4 mg of (E)-3-(5-{(E)-3-[4-(4-acetyl-piperazin-1-ylmethyl)-phenyl]-3-oxo-propenyl}-pyridin-2-yl)-N-hydroxy-acrylamide as its bis-trifluoroacetate salt.

LC-MS: Method F, rt=0.94; (ES+) MH$^+$: 435.21

$^1$H NMR (DMSO-d$_6$ 353K+TFA) δ (ppm): 9.01 (d, 1H), 8.31 (dd, 1H), 8.21 (m, 2 H), 7.97 (d, 1H), 7.77 (d, 1H), 7.71 (m, 2H), 7.66 (d, 1H), 7.52 (d, 1H), 7.05 (d, 1H), 4.42 (s, 2H), 3.71 (m, 4H), 3.03-3.35 (m, 4H), 2.05 (s, 3H).

Example 50

(E)-N-Hydroxy-3-(5-{(E)-3-[4-(4-methyl-piperazin-1-ylmethyl)-phenyl]-3-oxo-propenyl}-pyridin-2-yl)-acrylamide

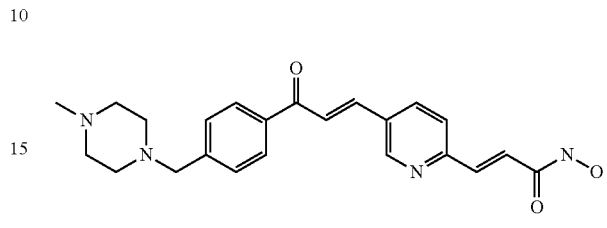

Step A

A solution of 1-(4-hydroxymethyl-phenyl)-ethanone (750 mg, 5 mmol) in EtOH (15 ml) was added dropwise at 0° C. to a stirred solution of (E)-3-(5-formyl-pyridin-2-yl)-acrylic acid tert-butyl ester (described in Example 11 STEP A-D, 1.16 g, 5 mmol) and 1.7 M KOH (4.4 ml) in EtOH (10 ml). The mixture was stirred at 0° C. for 5 h and the resulting precipitate was filtered and triturated with di-isopropylether to give 630 mg of desired (E)-3-{5-[(E)-3-(4-hydroxymethyl-phenyl)-3-oxo-propenyl]-pyridin-2-yl}-acrylic acid tert-butyl ester. The mother liquors were diluted with water and extracted with AcOEt. The organic layer was dried over Na$_2$SO$_4$ and evaporated in vacuo. The residue was triturated with EtOH to give additional 70 mg of (E)-3-{5-[(E)-3-(4-hydroxymethyl-phenyl)-3-oxo-propenyl]-pyridin-2-yl}-acrylic acid tert-butyl ester.

Y=39%

Step B

A solution of (E)-3-{5-[(E)-3-(4-hydroxymethyl-phenyl)-3-oxo-propenyl]-pyridin-2-yl}-acrylic acid tert-butyl ester (700 mg, 1.92 mmol) and TFA (2.9 ml) in DCM (10 ml) was stirred at room temperature for 3 h and then the solvent was evaporated in vacuo. The resulting yellow solid was treated with a solution of KOH (240 mg, 4.28 mmol) in EtOH (30 ml) for 30 min. The mixture was acidified with HCl/Et$_2$O and the solid was filtered with a buchner funnel. The powder was dissolved in DCM (10 ml), DMF (10 ml) and TEA (1.1 ml, 7.76 mmol), HOBT (524 mg, 3.88 mmol), EDC (741 mg, 3.88 mmol) and NH$_2$OTHP (227 mg, 1.94 mmol) were added. The solution was stirred at room temperature overnight and then diluted with water and extracted twice with DCM. The organic layer was washed with water, dried over Na$_2$SO$_4$ and evaporated in vacuo. The crude reaction mixture was purified by column chromatography (eluent: DCM/MeOH/NH$_4$OH 95:5:0.1) to give 230 mg of (E)-3-{5-[(E)-3-(4-hydroxymethyl-phenyl)-3-oxo-propenyl]-pyridin-2-yl}-N-(tetrahydro-pyran-2-yloxy)-acrylamide.

Y=30%

Step C

Methanesulfonyl chloride (0.133 ml, 1.72 mmol) was added dropwise to a stirred solution of (E)-3-{5-[(E)-3-(4-hydroxymethyl-phenyl)-3-oxo-propenyl]-pyridin-2-yl}-N-(tetrahydro-pyran-2-yloxy)-acrylamide (230 mg, 0.56 mmol) and TEA (0.48 ml, 3.44 mmol) in DCM (2.5 ml) and DMF (2.5 ml). The resulting mixture was stirred at room temperature for 40 min. Then further methanesulfonyl chloride (0.067 ml, 0.86 mmol) and TEA (0.120 ml, 0.86 mmol) were added. After stirring for additional 1 h the solution was treated with 5% NaHCO₃ and extracted twice with DCM. The collected organic phases were washed with water, dried over Na₂SO₄ and evaporated in vacuo. The crude mixture was purified by column chromatography (eluent: DCM/MeOH/NH₄OH 97:3:0.1) to give 275 mg of a mixture of methanesulfonic acid 4-((E)-3-{6-[(E)-2-(tetrahydro-pyran-2-yloxycarbamoyl)-vinyl]-pyridin-3-yl}-acryloyl)-benzyl ester and (E)-3-{5-[(E)-3-(4-chloromethyl-phenyl)-3-oxo-propenyl]-pyridin-2-yl}-N-(tetrahydro-pyran-2-yloxy)-acrylamide. 80 mg of this mixture were dissolved in CH₃CN (10 ml) and TEA (0.046 ml, 0.33 mmol) and N-methyl piperazine (0.022 ml, 0.198 mmol) were added. The solution was stirred at 80° C. for 1 h and then at room temperature overnight. Further N-methyl piperazine (0.022 ml, 0.198 mmol) and TEA (0.046 ml, 0.33 mmol) were added and the mixture was stirred at 80° C. for additional 1 h. The solvent was removed in vacuo and the residue was partitioned between water and AcOEt. The organic phase was dried over Na₂SO₄ and evaporated. The crude reaction mixture was purified by column chromatography (eluent: DCM/MeOH/NH₄OH 97:3:0.1) and the product was dissolved in DCM and treated with HCl/Et₂O for 2 h. The resulting precipitate was filtered and rinsed with DCM to give 14.5 mg of (E)-N-Hydroxy-3-(5-{(E)-3-[4-(4-methyl-piperazin-1-ylmethyl)-phenyl]-3-oxo-propenyl}-pyridin-2-yl)-acrylamide as its tris-hydrochloride salt.

Y=3.3%

LC-MS: Method F, rt=1.07; (ES+) MH⁺: 407.26

1H NMR (DMSO-d₆ 353K+TFA) δ (ppm): 9.01 (d, 1H), 8.31 (dd, 1H), 8.14 (m, 2 H), 7.89-8.05 (m, 1H), 7.75 (d, 1H), 7.63-7.71 (m, 3H), 7.52 (d, 1H), 7.06 (d, 1H), 4.05 (s, 2H), 3.26-3.47 (m, 4H), 2.97-3.21 (m, 4H), 2.79 (s, 3H).

Example 51

(E)-3-(4-{(E)-3-[2-Chloro-5-(4-methyl-piperazin-1-yl)-phenyl]-3-oxo-propenyl}-phenyl)-N-hydroxy-acrylamide

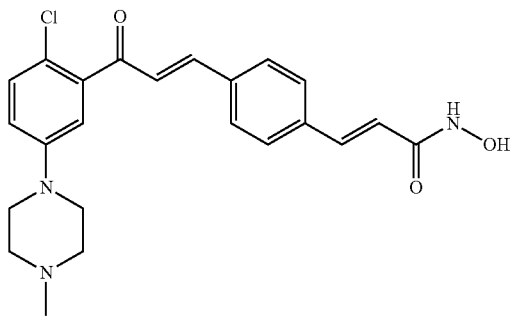

Step A

A mixture of 4-formylcinnamic acid (250 mg, 1.42 mmol), 1-[2-chloro-5-(4-methyl-piperazin-1-yl)-phenyl]-ethanone (obtained as described in Preparation 13, 358 mg, 1.42 mmol) and 1.7 M KOH (1.67 ml) in EtOH (10 ml) was stirred at 0° C. for 6 h and then acidified with 10% HCl until reaching a pH value of 6. The resulting yellow precipitate was filtered and rinsed with EtOH and Et₂O to give 519 mg of (E)-3-(4-{(E)-3-[2-chloro-5-(4-methyl-piperazin-1-yl)-phenyl]-3-oxo-propenyl}-phenyl)-acrylic acid. The reaction product was used in the next step without any further purification.

Step B

A mixture of (E)-3-(4-{(E)-3-[2-chloro-5-(4-methyl-piperazin-1-yl)-phenyl]-3-oxo-propenyl}-phenyl)-acrylic acid (compound from STEP A, 205 mg), HOBT (134 mg, 0.99 mmol), EDC (190 mg, 0.99 mmol), TEA (0.138 ml, 0.99 mmol) and NH₂OTHP (70 mg, 0.60 mmol) in DMF (10 ml) was stirred at room temperature overnight. The reaction mixture was diluted with water and extracted with AcOEt twice. The organic phases were washed with water, brine and then dried over Na₂SO₄ and evaporated in vacuo. The crude mixture was purified by silica gel chromatography (eluent: DCM/MeOH/NH₄OH 95:5:0.2) and the resulting product was dissolved in DCM and treated with HCl/Et₂O for 3 h. The precipitate was filtered and rinsed with DCM and Et₂O to give 124 mg of (E)-3-(4-{(E)-3-[2-chloro-5-(4-methyl-piperazin-1-yl)-phenyl]-3-oxo-propenyl}-phenyl)-N-hydroxy-acrylamide hydrochloride.

LC-MS: Method F, rt=1.40; (ES+) MH⁺: 426.19

¹H NMR (DMSO-d₆ 353K) δ (ppm): 7.76 (m, 2H), 7.61 (m, 2H), 7.48 (d, 1H), 7.45 (d, 1H), 7.42 (d, 1H), 7.22 (d, 1H), 7.16 (dd, 1H), 7.12 (d, 1H), 6.62 (d, 1 H), 3.86 (m, 4H), 3.22 (m, 4H), 2.83 (s, 3H).

Example 52

(E)-3-(5-{(E)-3-[3-Chloro-5-(4-methyl-piperazin-1-yl)-phenyl]-3-oxo-propenyl}-pyridin-2-yl)-N-hydroxy-acrylamide

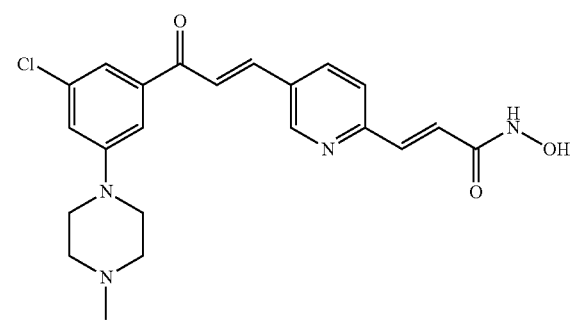

Step A

A solution of 1-[3-chloro-5-(4-methyl-piperazin-1-yl)-phenyl]-ethanone (obtained as described in Preparation 4, 360 mg, 1.43 mmol) in EtOH (20 ml) was added dropwise to a stirred solution of (E)-3-(5-formyl-pyridin-2-yl)-acrylic acid tert-butyl ester (described in Example 11 STEP A-D, 332 mg, 1.43 mmol) and 1.7 M KOH (0.85 ml) in EtOH (15 ml), cooled down to −15° C. The mixture was stirred at −15° C. for 3 h and then partitioned between water and AcOEt. The organic layer was dried over Na₂SO₄ and evaporated in vacuo. The crude reaction mixture was purified by column chromatography (eluent: DCM/MeOH/NH₄OH 96:4:0.1) and the resulting product was dissolved in DCM (2 ml) and TFA (0.6 ml). The solution was stirred at room temperature for 4 h and then the solvent was removed in vacuo to give 192 mg of (E)-3-(5-{(E)-3-[3-chloro-5-(4-methyl-piperazin-1-yl)-phenyl]-3-oxo-propenyl}-pyridin-2-yl)-acrylic acid bis-trifluoroacetate. The crude mixture was used in the next step without any further purification.

Step B

A mixture of (E)-3-(5-{(E)-3-[3-chloro-5-(4-methyl-piperazin-1-yl)-phenyl]-3-oxo-propenyl}-pyridin-2-yl)-acrylic acid bis-trifluoroacetate (obtained in STEP A, 190 mg), HOBT (81 mg, 0.60 mmol), EDC (115 mg, 0.60 mmol), TEA (0.335 ml, 2.4 mmol) and NH₂OTHP (52.6 mg, 0.45 mmol) in DCM (7 ml) was stirred at room temperature for 4 h. The solvent was evaporated and the residue was partitioned between water and AcOEt. The organic phase was dried over Na₂SO₄ and evaporated in vacuo. The crude mixture was purified by silica gel chromatography (eluent: DCM/MeOH/NH₄OH from 97:3:0.1 to 95:5:0.1) and the resulting product was dissolved in DCM and treated with HCl/Et₂O at room temperature for 3 h. The precipitate was filtered and triturated with isopropanol. The crude mixture was purified by preparative LC-MS to give 25 mg (E)-3-(5-{(E)-3-[3-chloro-5-(4-methyl-piperazin-1-yl)-phenyl]-3-oxo-propenyl}-pyridin-2-yl)-N-hydroxy-acrylamide as its bis-trifluoroacetate salt.

LC-MS: Method F, rt=1.83; (ES+) MH⁺: 427.13

¹H NMR (DMSO-d₆) δ (ppm): 9.72 (bs 1H), 9.06 (d, 1H), 8.42 (dd, 1H), 8.06 (d, 1H), 7.80 (d, 1H), 7.64-7.76 (m, 2H), 7.47-7.64 (m, 2H), 7.39 (t, 1H), 7.01 (d, 1H), 3.94-4.16 (m, 2H), 3.40-3.65 (m, 2H), 3.05-3.23 (m, 4H), 2.88 (s, 3H).

Example 53

(E)-N-Hydroxy-3-(5-{(E)-3-[3-(4-methyl-piperazin-1-ylmethyl)-phenyl]-3-oxo-propenyl}-pyridin-2-yl)-acrylamide

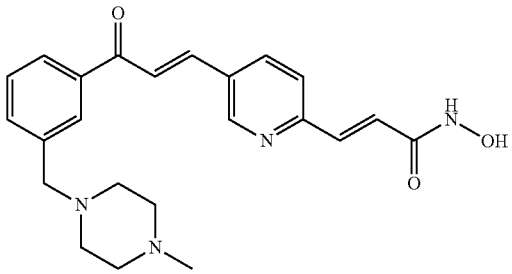

Step A 1.7 M KOH (0.634 ml) was added dropwise to a stirred mixture of (E)-3-(5-formyl-pyridin-2-yl)-acrylic acid tert-butyl ester (see Example 11 STEP A-D, 250 mg, 1.078 mmol) and 1-[3-(4-methyl-piperazin-1-ylmethyl)-phenyl]-ethanone (obtained as described in Preparation 14, 250 mg, 1.078 mmol) in EtOH (15 ml). The resulting solution was stirred at 0° C. for 7 h and then diluted with water and extracted with AcOEt. The organic phase was dried over Na₂SO₄ and evaporated in vacuo. The crude product was purified by chromatographic column (eluent: DCM/MeOH/NH₄OH from 97:3:0.1 to 95:5:0.2) and the desired intermediate was dissolved in DCM (4 ml) and TFA (1 ml). The mixture was stirred at room temperature for 6 h and then the solvent was removed in vacuo to give 200 mg of (E)-3-(5-{(E)-3-[3-(4-methyl-piperazin-1-ylmethyl)-phenyl]-3-oxo-propenyl}-pyridin-2-yl)-acrylic acid as its tris-trifluoroacetate salt. The crude mixture was used in the next step without further purifications.

Step B

A mixture of (E)-3-(5-{(E)-3-[3-(4-methyl-piperazin-1-ylmethyl)-phenyl]-3-oxo-propenyl}-pyridin-2-yl)-acrylic acid tris-trifluoroacetate (crude compound from STEP A, 194 mg), HOBT (83 mg, 0.616 mmol), EDC (118 mg, 0.616 mmol), TEA (0.127 ml, 0.92 mmol) and NH₂OTHP (44 mg, 0.376 mmol) in DMF (10 ml) was stirred at room temperature for 5 h. The resulting solution was diluted with water and extracted with AcOEt and DCM. The collected organic phases were washed with brine and then dried over Na₂SO₄ and evaporated in vacuo. The crude mixture was purified by column chromatography (eluent: DCM/MeOH/NH₄OH from 97:3:0.1 to 95:5:0.2) and the resulting product was dissolved in DCM and treated with HCl/Et₂O for 3 h. The precipitate was filtered and purified by preparative LC-MS to give 9 mg of (E)-N-hydroxy-3-(5-{(E)-3-[3-(4-methyl-piperazin-1-ylmethyl)-phenyl]-3-oxo-propenyl}-pyridin-2-yl)-acrylamide as its tris-trifluoroacetate salt.

LC-MS: Waters Acquity UPLC, Micromass ZQ Single quadrupole (Waters).

Column Acquity UPLC HSS T3, 2.1×100 mm, 1.8 μm;
flow rate: 0.6 ml/min splitting ratio MS:waste/1:4;
mobile phase: A phase=water/CH₃CN 95/5+0.1% TFA; B phase=water/CH₃CN 5/95+0.1% TFA. 0-0.5 min (A: 95%, B: 5%), 0.5-6 min (A: 0%, B: 100%), 6.00-7.00 min (A: 0%, B: 100%), 7.00-7.10 min (A: 95%, B: 5%); 7.10-8.50 min (A: 95%, B: 5%) UV detection wavelength 254 nm or BPI; Injection volume: 5 μl rt=2.00; (ES+) MH⁺: 407.21

¹H NMR (DMSO-d₆ 353K+TFA) δ (ppm): 9.00 (d, 1H), 8.29 (dd, 1H), 8.08 (dt, 1 H), 8.04 (t, 1H), 7.94 (d, 1H), 7.75 (d, 1H), 7.62-7.69 (m, 2H), 7.58 (t, 1 H), 7.52 (d, 1H), 7.05 (d, 1H), 3.79 (s, 2H), 3.23 (bs, 4H), 2.80 (s, 3H), 2.68-2.85 (m, 4H).

2. Biological Testing
Methods and Results
2.1 Histone Acetylation Assay

In order to assess the ability of the compounds to modify histone acetylation levels, a dose-response study was carried out using the cell line K562 (derived from human lymphoma). Briefly, the cells were incubated with the compound for 3 hours, then fixed with 1% formaldehyde in PBS and permeabilized with a solution containing 0.1% Triton X-100 in PBS. After washing, the cells were pre-incubated with 10% goat serum in PBS for 30 minutes at 4° C., exposed for 1 hour at room temperature to a monoclonal antibody against acetylated histones and then incubated for one hour with a secondary antibody conjugated with FITC. Histone acetylation levels were measured by cytofluorometry (FACS) (Ronzoni, S. et al. *Cytometry A*. 2005, 66, 52-61).

The compounds of the present invention showed a remarkable histone deacetylase inhibitory activity (calculated on increase in acetylation) at low micromolar concentrations or even below.

2.2 Assay of Enzyme Inhibition of HDAC

The in-vitro activity of HDAC inhibitors was assayed by means of a biochemical assay using a BIOMOL Kit, according to the recommended experimental conditions. In a first step, 5 μg of a nuclear extract of HeLa cells were added to a solution containing the HDAC inhibitor and the substrate (lysine with acetylated amino on the side chain) at a concentration of 116 μM. The samples were incubated for 10 minutes at room temperature and then exposed to a developer (15 minutes at room temperature). In this last step a fluorophore was produced, whose fluorescence was measured using an excitation wavelength of 355 nm and an emission at 460 nm.

The obtained results are illustrated in the following tables 4-6, wherein the compounds of the invention are grouped together depending on their belonging to formula (Ia), (Ib) or (Ic). In tables 4-6, the reference HDAC inhibitors marked with (*) are those disclosed in the patent application PCT/EP2005/054949.

As evident from comparison with the reference HDAC inhibitors of the prior art, the compounds of the invention showed a significant enhancement of activity.

TABLE 4

Compounds of formula (Ia)

| Example no. | Mol. structure | Activity IC$_{50}$ [μM] |
|---|---|---|
| 26 | (structure) | 0.0267 |
| 30 | (structure) | 0.025 |
| Ref (*) 48 | (structure) | 0.0733 |

TABLE 5

Compounds of formula (Ib)

| Example no. | Mol. structure | Activity IC$_{50}$ [μM] |
|---|---|---|
| 25 | (structure) | 0.035 |
| Ref (*) 29 | (structure) | 0.2825 |

TABLE 5-continued

Compounds of formula (Ib)

| Example no. | Mol. structure | Activity IC$_{50}$ [μM] |
|---|---|---|
| Ref (*) 41 | | 0.2375 |
| Ref (*) 59 | | 1.995 |

TABLE 6

Compounds of formula (Ic)

| Example no. | Mol. structure | Activity IC$_{50}$ [μM] |
|---|---|---|
| 39 | | 0.0061 |
| 42 | | 0.0048 |
| 43 | | 0.0040 |

TABLE 6-continued

Compounds of formula (Ic)

| Example no. | Mol. structure | Activity IC$_{50}$ [μM] |
|---|---|---|
| 44 | | 0.0013 |
| 45 | | 0.0007 |
| 47 | | 0.0118 |
| Ref (*) 69 | | 0.0225 |
| Ref (*) 71 | | 0.0675 |
| Ref (*) 72 | | 0.0200 |

2.3 Cell Growth: MTT Assay

The MTT [3-(4,5-dimethylthiazolyl)-2,5-diphenyltetrazolium bromide] test is a colorimetric test able to measure cell viability and proliferation, based on the capacity of cells to metabolise tetrazolium salt to form formazan crystals, by means of a mitochondrial dehydrogenase. The cells in exponential growth phase are exposed to the inhibitors. The activity of the mitochondrial dehydrogenase and the quantity of formazan salts produced are proportional to the number of survived cells. The quantity of formazan produced is detected by UV-VIS spectrophotometry.

K562 cells were incubated for 72 hours with different concentrations of the inhibitors. 5 mg/ml of MTT in PBS were added at different time points and the solution was incubated for 3-4 hours at 37° C. The supernatant was then removed and the formazan crystals were dissolved in a mixture of DMSO and absolute ethanol (1:1, v:v) and the solution analysed with a spectrophotometer at a wavelength between 550 and 570 nm. The $IC_{50}$ is calculated using GraphPad Software.

2.4 Cell Cycle and Apoptosis

A suspension of K562 or HT29 cells was treated with increasing amounts of HDAC inhibitors in order to assess the biological response. In order to establish the effect of the HDAC inhibitors on the cell cycle and apoptosis the cells were fixed in 70% ethanol for 30 minutes, re-suspended in propidium iodide (PI: 50 µg/ml) with added RNAse (250 µg/ml) and incubated for 24 hours at room temperature. The samples were analysed using a FACScan Cytometer (Beckton Dickinson). The tested compounds were able to determine a clear cell cycle modification and to induce apoptosis evaluated as sub-G1 analysis.

2.5 Metabolic Stability in Hepatic Microsomes

Experimental Procedure

The test compound was dissolved in DMSO at the final concentration of 1 µM and pre-incubated for 10 min at 37° C. in potassium phosphate buffer pH 7.4 together with mouse or human hepatic microsomes (Xenotech) at the final concentration of 0.5 mg/ml.

After the pre-incubation the reaction was started by adding the cofactor mixture (NADP, G6P, G6P-DH); aliquots were taken at time 0 and 30 min, added to acetonitrile in order to stop the reaction. After centrifugation the supernatant was separated and analyzed by LC-MS/MS.

A control sample without cofactor was always studied in parallel in order to check the chemical stability of the test compound.

Two reference compounds of known metabolic stability 7-ethoxycoumarin and propranolol were present each time to access the validity of the experiment.

A fixed concentration of verapamil was added in each sample as internal standard for the LC-MS/MS analysis.

Data Analysis

The percentage of the compound remaining after 30 min incubation period was calculated according the following equation: [area at time 30 min]/[area at time 0 min]*100%.

Sample Analysis

HPLC Conditions

Samples were analyzed on an Acquity UPLC (Waters) coupled with a Sample Organizer and interfaced with a triple quadrupole Premiere XE (Waters).

Eluents were:

Phase A: 95% $H_2O$, 5% ACN+0.1% HCOOH

Phase B: 5% $H_2O$, 95% ACN+0.1% HCOOH

Column: Acquity BEH C18 50×2.1 mm 1.7 µm at 40° C. Flow 0.45 ml/min, alternatively Acquity BEH C18 50×1 mm 1.7 µm at 40° C. Flow 0.2 ml/min, Chromatographic method is reported below.

TABLE 7

| Chromatographic method | | |
|---|---|---|
| Time (min) | % A | % B |
| 0 | 98 | 2 |
| 0.2 | 98 | 2 |
| 0.21 | 0 | 100 |
| 1.5 | 0 | 100 |
| 1.6 | 98 | 2 |
| 2 | 98 | 2 |

MS Method

Samples were analyzed in MRM (Multiple Reaction Monitoring) ESI Pos mode.

MS Conditions: Capillary Voltage 3.4 kV, Source Temp. 115° C., Desolvation Temp. 450° C., Desolvation gas 900 l/h, Cell Pressure 3.3 $10^{-3}$ mbar.

Cone Voltage and Collision Energy were optimized for each compound. The acquisition of each compound was performed together with the internal standard verapamil.

The obtained results are illustrated in the following tables 8-10, wherein the compounds of the invention are grouped together depending on their belonging to formula (Ia), (Ib) or (Ic). The reference HDAC inhibitors marked with (*) are those disclosed in the patent application PCT/EP2005/054949.

As evident from comparison with the reference HDAC inhibitors of the prior art, the compounds of the invention showed a significant enhancement in metabolic stability.

TABLE 8

| | Compounds of formula (Ia) | | |
|---|---|---|---|
| Example no. | Mol. structure | Met. mouse | Met. human |
| 7 | | 16.75 | 61.16 |

TABLE 8-continued
Compounds of formula (Ia)
| Example no. | Mol. structure | Met. mouse | Met. human |
|---|---|---|---|
| 26 | 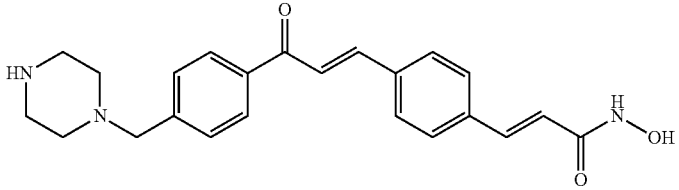 | 42.41 | 50.84 |
| Ref (*) 48 | 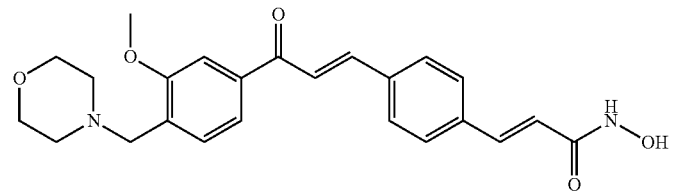 | 2.8 | 35.28 |
TABLE 9
Compounds of formula (Ib)
| Example no. | Mol. structure | Met. mouse | Met. human |
|---|---|---|---|
| 1 | 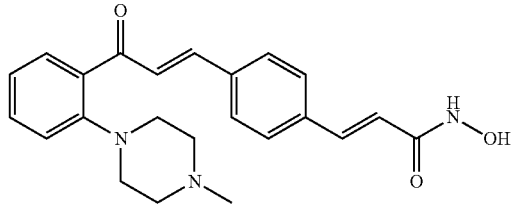 | 33.81 | 38.16 |
| 4 | 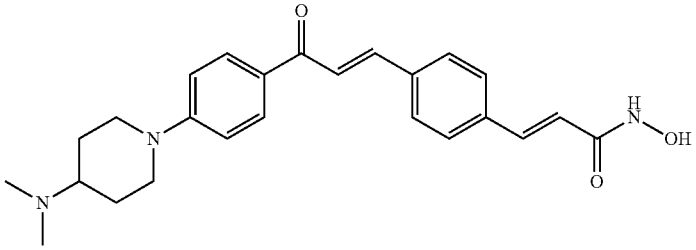 | 14.00 | 41.88 |
| 15 | 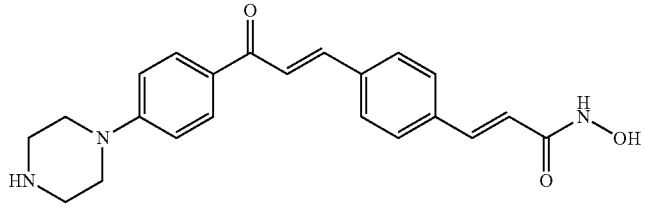 | 30.5 | 42.58 |

TABLE 9-continued

| Compounds of formula (Ib) | | | |
|---|---|---|---|
| Example no. | Mol. structure | Met. mouse | Met. human |
| 25 | (3-chloro-5-(4-methylpiperazin-1-yl)phenyl ketone linked via enone to phenyl-acrylohydroxamic acid) | 84.89 | 57.28 |
| Ref (*) 29 | (4-morpholinophenyl ketone linked via enone to 2-fluorophenyl-acrylohydroxamic acid) | 11.17 | 20.86 |
| Ref (*) 41 | (4-morpholinophenyl ketone linked via enone to phenyl-acrylohydroxamic acid) | 2.76 | 8.66 |
| Ref (*) 59 | (4-(4-methylpiperazin-1-yl)phenyl ketone linked via enone to phenyl-acrylohydroxamic acid) | 9.12 | 33.29 |

TABLE 10

| Compounds of formula (Ic) | | | |
|---|---|---|---|
| Example no. | Mol. structure | Met. mouse | Met. human |
| 39 | (4-((2S,5R)-2,5-dimethyl-4-methylpiperazin-1-yl)phenyl ketone linked via enone to pyridyl-acrylohydroxamic acid) | 20.29 | 44.35 |

TABLE 10-continued
Compounds of formula (Ic)
| Example no. | Mol. structure | Met. mouse | Met. human |
|---|---|---|---|
| 42 | 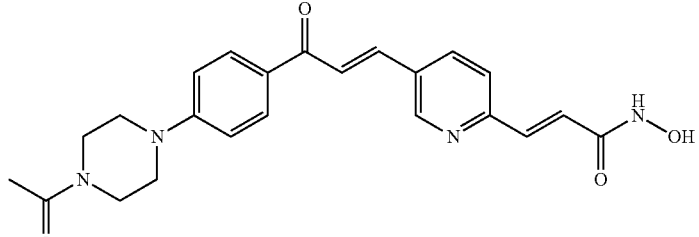 | 50.47 | 35.27 |
| 43 | 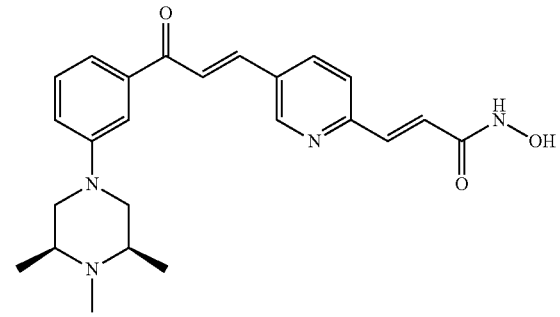 | 42.45 | 37.29 |
| 44 | 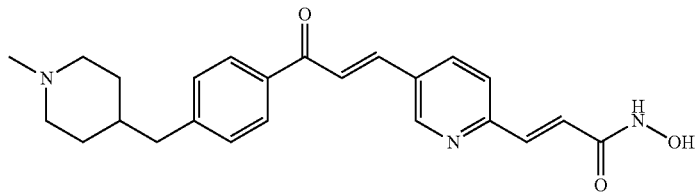 | 54.56 | 34.38 |
| 45 | 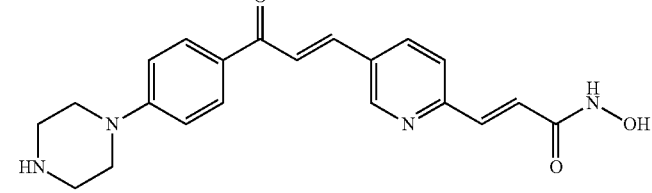 | 43.41 | 53.65 |
| 47 | 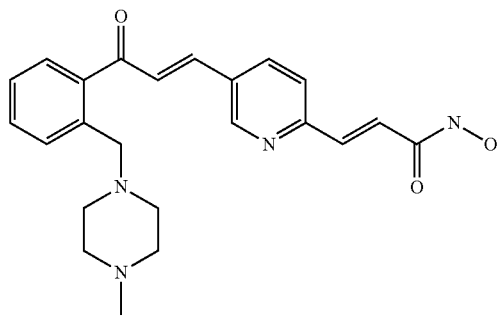 | 52.66 | 93.48 |
| Ref (*) 69 | 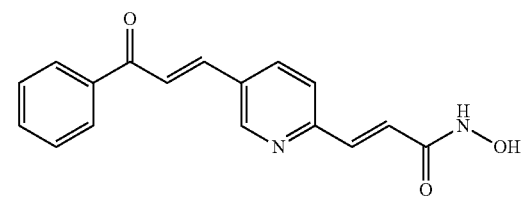 | 5.65 | 13.74 |

TABLE 10-continued

Compounds of formula (Ic)

| Example no. | Mol. structure | Met. mouse | Met. human |
|---|---|---|---|
| Ref (*) 71 | | 6.04 | 21.82 |
| Ref (*) 72 | | 10.83 | 15.32 |

The invention claimed is:

1. A compound of formula (I)

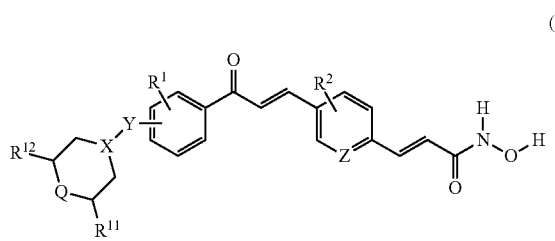

(I)

wherein:
Q is a bond, $CH_2$, $CH-NR^3R^4$, $NR^5$ or oxygen;
X is CH or nitrogen;
Y is a bond, $CH_2$, oxygen or $NR^6$;
Z is CH or nitrogen;
$R^1$, $R^2$ are, independently, hydrogen, halogen, $C_1$-$C_6$alkyl, or $C_1$-$C_6$haloalkyl:
$R^3$, $R^4$ are, independently, hydrogen, $C_1$-$C_6$alkyl, phenyl or benzyl;
$R^5$ is hydrogen, $C_1$-$C_6$ alkyl, $(CO)R^7$, $SO_2$—$C_1$-$C_6$ alkyl, phenyl or benzyl;
$R^6$ is hydrogen, $C_1$-$C_6$ alkyl or benzyl;
$R^7$ is hydrogen, $C_1$-$C_6$ alkyl, phenyl, benzyl, $OR^8$ or $NR^9R^{10}$;
$R^8$ is $C_1$-$C_6$ alkyl;
$R^9$ is hydrogen, $C_1$-$C_6$ alkyl, phenyl or benzyl;
$R^{10}$ is hydrogen, $C_1$-$C_6$ alkyl or benzyl;
$R^{11}$, $R^{12}$ are, independently, hydrogen or $C_1$-$C_6$ alkyl;
and the pharmaceutically acceptable salts thereof;
with the proviso that when X is nitrogen, Y cannot be oxygen or $NR^6$;
and with the exclusion of the following compounds:
(E)-N-Hydroxy-3-(4-{(E)-3-[4-(4-methyl-piperazin-1-yl)-phenyl]-3-oxo-propenyl}-phenyl)-acrylamide;
(E)-N-Hydroxy-3-{4-[(E)-3-(4-morpholin-4-yl-phenyl)-3-oxo-propenyl]-phenyl}-acrylamide;
(E)-3-{3-Fluoro-4-[(E)-3-(4-morpholin-4-yl-phenyl)-3-oxo-propenyl]-phenyl}-N-hydroxy-acrylamide.

2. Compound according to claim 1, wherein one or more of the aforesaid alkyls is a $C_1$-$C_4$ alkyl group.

3. Compound according to claim 1, wherein:
$R^1$, $R^2$ are, independently, hydrogen, fluorine, chlorine, $C_1$-$C_2$ alkyl, or $CF_3$;
$R^3$, $R^4$ are, independently, hydrogen, $C_1$-$C_2$alkyl, phenyl or benzyl;
$R^5$ is hydrogen, $C_1$-$C_2$ alkyl, $(CO)R^7$, $SO_2$—$C_1$-$C_2$alkyl, phenyl or benzyl;
$R^6$ is hydrogen, $C_1$-$C_2$ alkyl or benzyl;
$R^7$ is hydrogen, $C_1$-$C_2$ alkyl, phenyl, benzyl, $OR^8$ or $NR^9R^{10}$;
$R^8$ is $C_1$-$C_2$ alkyl;
$R^9$ is hydrogen, $C_1$-$C_2$ alkyl, phenyl or benzyl;
$R^{10}$ is hydrogen, $C_1$-$C_2$ alkyl or benzyl;
$R^{11}$, $R^{12}$ are, independently, hydrogen or $C_1$-$C_2$ alkyl.

4. Compound according to claim 1, having formula (Ia),

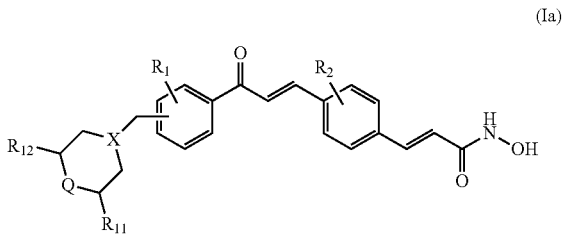

(Ia)

wherein:
Q is $CH_2$, $CH-NR^3R^4$, or $NR^5$;
X is CH or nitrogen;
$R^1$, $R^2$ are, independently, hydrogen, halogen, $C_1$-$C_4$alkyl, or $C_1$-$C_4$ haloalkyl;
$R^3$, $R^4$ are, independently, hydrogen or $C_1$-$C_4$ alkyl;
$R^5$ is hydrogen, $C_1$-$C_4$ alkyl, $(CO)R^7$, phenyl or benzyl;
$R^7$ is hydrogen, $C_1$-$C_6$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_4$ alkyl;
$R^{11}$, $R^{12}$ are, independently, hydrogen or $C_1$-$C_4$ alkyl.

5. Compound according to claim 4, wherein:
Q is $CH_2$, CH—$NR^3R^4$, or $NR^5$;
X is CH or nitrogen;
$R^1$, $R^2$ are, independently, hydrogen, fluoro, chloro, or $CF_3$;
$R^3$, $R^4$ are, independently, hydrogen or $C_1$-$C_2$ alkyl;
$R^5$ is hydrogen, $C_1$-$C_4$ alkyl, (CO)$R^7$, phenyl or benzyl;
$R^7$ is hydrogen, $C_1$-$C_4$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_2$ alkyl;
$R^{11}$, $R^{12}$ are, independently, hydrogen or $C_1$-$C_2$ alkyl.

6. Compound according to claim 4, wherein:
Q is $NR^5$;
X is nitrogen;
$R^1$, $R^2$ are, independently, hydrogen, fluoro, chloro or $CF_3$;
$R^5$ is hydrogen, $C_1$-$C_4$ alkyl, (CO)$R^7$, phenyl or benzyl;
$R^7$ is hydrogen, $C_1$-$C_4$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_2$ alkyl;
$R^{11}$, $R^{12}$ are, independently, hydrogen or $C_1$-$C_2$ alkyl.

7. Compound according to claim 4, selected from:
(E)-N-Hydroxy-3-(4-{(E)-3-[4-(4-methyl-piperazin-1-ylmethyl)-phenyl]-3-oxo-propenyl}-phenyl)-acrylamide;
(E)-3-(4-{(E)-3-[4-(4-Dimethylamino-piperidin-1-yl-methyl)-phenyl]-3-oxo-propenyl}-phenyl)-N-hydroxy-acrylamide;
(E)-N-Hydroxy-3-(4-{(E)-3-[4-(1-methyl-piperidin-4-yl-methyl)-phenyl]-3-oxo-propenyl}-phenyl)-acrylamide;
(E)-N-Hydroxy-3-{4-[(E)-3-oxo-3-(4-piperazin-1-ylmethyl-phenyl)-propenyl]-phenyl}-acrylamide;
(E)-3-(4-{(E)-3-[4-(4-Benzyl-piperazin-1-ylmethyl)-phenyl]-3-oxo-propenyl}-phenyl)-N-hydroxy-acrylamide;
(E)-3-(4-{(E)-3-[4-((3R,5S)-3,5-Dimethyl-piperazin-1-ylmethyl)-phenyl]-3-oxo-propenyl}-phenyl)-N-hydroxy-acrylamide;
(E)-3-(4-{(E)-3-[4-(4-Acetyl-piperazin-1-ylmethyl)-phenyl]-3-oxo-propenyl}-phenyl)-N-hydroxy-acrylamide;
(E)-3-(4-{(E)-3-[4-((3R,5S)-4-Acetyl-3,5-dimethyl-piperazin-1-ylmethyl)-phenyl]-3-oxo-propenyl}-phenyl)-N-hydroxy-acrylamide;
(E)-3-(4-{(E)-3-[4-(4-Ethyl-piperazin-1-ylmethyl)-phenyl]-3-oxo-propenyl}-phenyl)-N-hydroxy-acrylamide;
(E)-N-Hydroxy-3-(4-{(E)-3-[3-(4-methyl-piperazin-1-ylmethyl)-phenyl]-3-oxo-propenyl}-phenyl)-acrylamide;
(E)-N-Hydroxy-3-(4-{(E)-3-[2-(4-methyl-piperazin-1-ylmethyl)-phenyl]-3-oxo-propenyl}-phenyl)-acrylamide.

8. Compound according to claim 1, having formula (Ib)

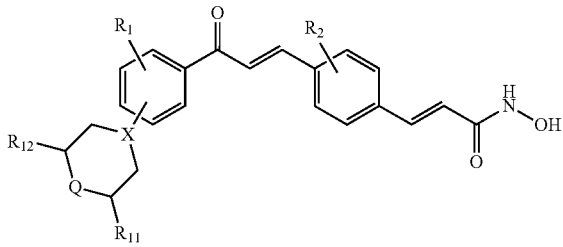

(Ib)

wherein:
Q is $CH_2$, CH—$NR^3R^4$, or $NR^5$;
X is CH or nitrogen;
$R^1$, $R^2$ are, independently, hydrogen, halogen, $C_1$-$C_4$ alkyl or $C_1$-$C_4$ haloalkyl;
$R^3$, $R^4$ are, independently, hydrogen or $C_1$-$C_4$ alkyl;
$R^5$ is hydrogen, $C_1$-$C_4$ alkyl, (CO)$R^7$, $SO_2$—$C_1$-$C_4$ alkyl, phenyl or benzyl;
$R^7$ is hydrogen, $C_1$-$C_6$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_4$ alkyl;
$R^{11}$, $R^{12}$ are, independently, hydrogen or $C_1$-$C_4$ alkyl;
with the exclusion of the following compound:
(E)-N-Hydroxy-3-(4-{(E)-3-[4-(4-methyl-piperazin-1-yl)-phenyl]-3-oxo-propenyl}-phenyl)-acrylamide.

9. Compound according to claim 8, wherein, within said formula (Ib), the group:

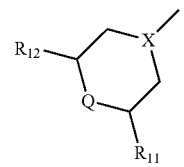

is in ortho or meta position with respect to the 3-oxo-propenyl moiety, and:
Q is $CH_2$ or $NR^5$;
X is CH or nitrogen;
$R^1$, $R^2$ are, independently, hydrogen, fluoro, chloro or $CF_3$;
$R^5$ is hydrogen, $C_1$-$C_4$ alkyl, (CO)$R^7$, phenyl or benzyl;
$R^7$ is hydrogen, $C_1$-$C_4$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_2$ alkyl;
$R^{11}$, $R^{12}$ are, independently, hydrogen or $C_1$-$C_2$ alkyl.

10. Compound according to claim 8, selected from:
(E)-3-(4-{(E)-3-[5-Chloro-2-(4-methyl-piperazin-1-yl)-phenyl]-3-oxo-propenyl}-phenyl)-N-hydroxy-acrylamide;
(E)-N-Hydroxy-3-(4-{(E)-3-[2-(4-methyl-piperazin-1-yl)-phenyl]-3-oxo-propenyl}-phenyl)-acrylamide;
(E)-N-Hydroxy-3-(4-{(E)-3-[3-(4-methyl-piperazin-1-yl)-phenyl]-3-oxo-propenyl}-phenyl)-acrylamide;
(E)-N-Hydroxy-3-(4-{(E)-3-[4-(4-methylamino-piperidin-1-yl)-phenyl]-3-oxo-propenyl}-phenyl)-acrylamide;
(E)-3-(4-{(E)-3-[4-(4-Dimethylamino-piperidin-1-yl)-phenyl]-3-oxo-propenyl}-phenyl)-N-hydroxy-acrylamide;
(E)-N-Hydroxy-3-(4-{(E)-3-[4-(1-methyl-piperidin-4-yl)-phenyl]-3-oxo-propenyl}-phenyl)-acrylamide;
(E)-N-Hydroxy-3-(4-{(E)-3-[4-(4-isobutyl-piperazin-1-yl)-phenyl]-3-oxo-propenyl}-phenyl)-acrylamide;
(E)-3-(4-{(E)-3-[4-(4-Ethyl-piperazin-1-yl)-phenyl]-3-oxo-propenyl}-phenyl)-N-hydroxy-acrylamide;
(E)-3-(4-{(E)-3-[4-(4-Benzyl-piperazin-1-yl)-phenyl]-3-oxo-propenyl}-phenyl)-N-hydroxy-acrylamide;
(E)-N-Hydroxy-3-{4-[(E)-3-(4-piperazin-1-yl-phenyl)-3-oxo-propenyl]-phenyl}-acrylamide;
(E)-3-(4-{(E)-3-[4-(4-Benzoyl-piperazin-1-yl)-phenyl]-3-oxo-propenyl}-phenyl)-N-hydroxy-acrylamide;
(E)-3-(4-{(E)-3-[4-(4-Acetyl-piperazin-1-yl)-phenyl]-3-oxo-propenyl}-phenyl)-N-hydroxy-acrylamide;
(E)-N-Hydroxy-3-(4-{(E)-3-[4-(4-methanesulfonyl-piperazin-1-yl)-phenyl]-3-oxo-propenyl}-phenyl)-acrylamide;

4-(4-{(E)-3-[4-((E)-2-Hydroxycarbamoyl-vinyl)-phenyl]-acryloyl}-phenyl)-piperazine-1-carboxylic acid dimethylamide;
4-(4-{(E)-3-[4-((E)-2-Hydroxycarbamoyl-vinyl)-phenyl]-acryloyl}-phenyl)-piperazine-1-carboxylic acid amide;
4-(4-{(E)-3-[4-((E)-2-Hydroxycarbamoyl-vinyl)-phenyl]-acryloyl}-phenyl)-piperazine carboxylic acid ethyl ester;
(E)-N-Hydroxy-3-(4-{(E)-3-oxo-3-[4-((3R,5S)-3,4,5-trimethyl-piperazin-1-yl)-phenyl]-propenyl}-phenyl)-acrylamide;
(E)-3-(4-{(E)-3-[3-Chloro-5-(4-methyl-piperazin-1-yl)-phenyl]-3-oxo-propenyl}-phenyl)-N-hydroxy-acrylamide;
(E)-3-(4-{(E)-3-[2-Chloro-5-(4-methyl-piperazin-1-yl)-phenyl]-3-oxo-propenyl}-phenyl)-N-hydroxy-acrylamide.

11. Compound according to claim 1, having formula (Ic)

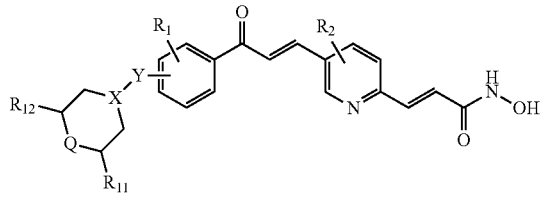

wherein:
Q is $CH_2$, CH—$NR^3R^4$, $NR^5$ or oxygen;
X is CH or nitrogen;
Y is a bond, $CH_2$, oxygen or $NR^6$;
$R^1$, $R^2$ are, independently, hydrogen, halogen, $C_1$-$C_4$ alkyl, or $C_1$-$C_4$ haloalkyl;
$R^3$, $R^4$ are, independently, hydrogen or $C_1$-$C_4$ alkyl;
$R^5$ is hydrogen, $C_1$-$C_4$ alkyl, (CO)$R^7$, phenyl or benzyl;
$R^6$ is hydrogen or $C_1$-$C_4$ alkyl;
$R^7$ is hydrogen, $C_1$-$C_6$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_4$ alkyl;
$R^{11}$, $R^{12}$ are, independently, hydrogen or $C_1$-$C_4$ alkyl;
provided that when X is nitrogen, Y cannot be oxygen or $NR^6$.

12. Compound according to claim 11, wherein:
Q is $CH_2$, $NR^5$ or oxygen;
X is CH or nitrogen;
Y is a bond or $CH_2$;
$R^1$, $R^2$ are, independently, hydrogen, fluoro, chloro or $CF_3$;
$R^5$ is hydrogen, $C_1$-$C_2$ alkyl, (CO)$R^7$, phenyl or benzyl;
$R^7$ is hydrogen, $C_1$-$C_4$ alkyl, phenyl, benzyl, $OR^8$ or $NR^9R^{10}$;
$R^8$ is $C_1$-$C_4$ alkyl;
$R^9$, $R^{10}$ are, independently, hydrogen or $C_1$-$C_2$ alkyl;
$R^{11}$, $R^{12}$ are, independently, hydrogen or $C_1$-$C_2$ alkyl.

13. Compound according to claim 11, selected from:
(E)-N-Hydroxy-3-(5-{(E)-3-[4-(4-methyl-piperazin-1-yl)-phenyl]-3-oxo-propenyl}-pyridin-2-yl)-acrylamide;
(E)-N-Hydroxy-3-(5-{(E)-3-[2-(4-methyl-piperazin-1-yl)-phenyl]-3-oxo-propenyl}-pyridin-2-yl)-acrylamide;
(E)-N-Hydroxy-3-(5-{(E)-3-[3-(4-methyl-piperazin-1-yl)-phenyl]-3-oxo-propenyl}-pyridin-2-yl)-acrylamide;
(E)-3-(5-{(E)-3-[4-(4-Benzyl-piperazin-1-yl)-phenyl]-3-oxo-propenyl}-pyridin-2-yl)-N-hydroxy-acrylamide;
(E)-N-Hydroxy-3-(5-{(E)-3-oxo-3-[4-((3R,5S)-3,4,5-trimethyl-piperazin-1-yl)-phenyl]-propenyl}-pyridin-2-yl)-acrylamide;
(E)-N-Hydroxy-3-{5-[(E)-3-(4-morpholin-4-ylmethyl-phenyl)-3-oxo-propenyl]-pyridin-2-yl}-acrylamide;
(E)-3-(5-{(E)-3-[4-(4-Ethyl-piperazin-1-yl)-phenyl]-3-oxo-propenyl}-pyridin-2-yl)-N-hydroxy-acrylamide;
(E)-3-(5-{(E)-3-[4-(4-Acetyl-piperazin-1-yl)-phenyl]-3-oxo-propenyl}-pyridin-2-yl)-N-hydroxy-acrylamide;
(E)-N-Hydroxy-3-(5-{(E)-3-oxo-3-[3-((3R,5S)-3,4,5-trimethyl-piperazin-1-yl)-phenyl]-propenyl}-pyridin-2-yl)-acrylamide;
(E)-N-Hydroxy-3-(5-{(E)-3-[4-(1-methyl-piperidin-4-ylmethyl)-phenyl]-3-oxo-propenyl}-pyridin-2-yl)-acrylamide;
(E)-N-Hydroxy-3-{5-[(E)-3-oxo-3-(4-piperazin-1-yl-phenyl)-propenyl]-pyridin-2-yl}-acrylamide;
(E)-N-Hydroxy-3-(5-{(E)-3-[2-(4-methyl-piperazin-1-ylmethyl)-phenyl]-3-oxo-propenyl}-pyridin-2-yl)-acrylamide;
(E)-N-Hydroxy-3-{5-[(E)-3-oxo-3-(4-piperazin-1-ylmethyl-phenyl)-propenyl]-pyridin-2-yl}-acrylamide;
(E)-3-(5-{(E)-3-[4-(4-Acetyl-piperazin-1-ylmethyl)-phenyl]-3-oxo-propenyl}-pyridin-2-yl)-N-hydroxy-acrylamide;
(E)-N-Hydroxy-3-(5-{(E)-3-[4-(4-methyl-piperazin-1-ylmethyl)-phenyl]-3-oxo-propenyl}-pyridin-2-yl)-acrylamide;
(E)-3-(5-{(E)-3-[3-Chloro-5-(4-methyl-piperazin-1-yl)-phenyl]-3-oxo-propenyl}-pyridin-2-yl)-N-hydroxy-acrylamide;
(E)-N-Hydroxy-3-(5-{(E)-3-[3-(4-methyl-piperazin-1-ylmethyl)-phenyl]-3-oxo-propenyl}-pyridin-2-yl)-acrylamide.

14. A pharmaceutical composition comprising one or more compounds of formula (I) as defined in claim 1, in association with pharmaceutically acceptable excipients.

15. A composition according to claim 14 in the form of a tablet, capsule, pill, oral preparation, powder, granular preparation, injectable or infusible solution or suspension, suppository, aqueous or oily suspension, solution, emulsion, syrup, elixir, cream, ointment, paste, gel, solution, oil or lotion, membrane or medicated patch.

* * * * *